United States Patent
Le Vezouet et al.

(10) Patent No.: US 9,029,639 B2
(45) Date of Patent: May 12, 2015

(54) PYRIDAZINE COMPOUNDS FOR CONTROLLING INVERTEBRATE PESTS

(75) Inventors: Ronan Le Vezouet, Mannheim (DE); Sebastian Soergel, Ludwigshafen (DE); Christian Defieber, Mannheim (DE); Steffen Gross, Ludwigshafen (DE); Karsten Koerber, Eppelheim (DE); Deborah L. Culbertson, Fuquay Varina, NC (US); Douglas D. Anspaugh, Apex, NC (US)

(73) Assignee: BASF SE, Ludwigshsafen (DE)

( * ) Notice: Subject to any disclaimer, the term of this patent is extended or adjusted under 35 U.S.C. 154(b) by 0 days.

(21) Appl. No.: 13/382,225

(22) PCT Filed: Jul. 1, 2010

(86) PCT No.: PCT/EP2010/059333
§ 371 (c)(1),
(2), (4) Date: Jan. 4, 2012

(87) PCT Pub. No.: WO2011/003796
PCT Pub. Date: Jan. 13, 2011

(65) Prior Publication Data
US 2012/0110704 A1    May 3, 2012

Related U.S. Application Data

(60) Provisional application No. 61/223,100, filed on Jul. 6, 2009.

(51) Int. Cl.
*A01H 5/00* (2006.01)
*C07D 417/12* (2006.01)
(Continued)

(52) U.S. Cl.
CPC .............. *C07D 417/12* (2013.01); *A01N 43/58* (2013.01); *A01N 43/76* (2013.01); *A01N 43/78* (2013.01); *C07D 403/12* (2013.01); *C07D 413/12* (2013.01)

(58) Field of Classification Search
CPC .............. C07D 417/122; C07D 403/12; C07D 413/12; A01N 43/58; A01N 43/78; A01N 43/76
USPC ........................ 800/298; 514/252.05; 544/238
See application file for complete search history.

(56) References Cited

U.S. PATENT DOCUMENTS 5,360,799 A    11/1994  Bachy et al.
6,747,041 B1   6/2004   Katsuhira et al.

(Continued)

FOREIGN PATENT DOCUMENTS

CA    2 026 131    3/1991
CN    1711255      12/2005
(Continued)

OTHER PUBLICATIONS

International Preliminary Report on Patentability issued Jan. 10, 2012, from corresponding International Application No. PCT/EP2010/059333, filed Jul. 1, 2010.
International Search Report completed Aug. 25, 2010, in International Application No. PCT/EP2010/059333, filed Jul. 1, 2010.
Milyutin, A.V., et al. "Synthesis properties and biological activity of 3-pyridylamides of 4-aryl-2-hydroxy-4-oxo-2-butenic (Aroylpyruvic) acids", Pharmaceutical Chemistry Journal, 1997, p. 30-33, vol. 31, No. 1.
(Continued)

*Primary Examiner* — Jason Sims
*Assistant Examiner* — Ibrahim D Bori
(74) *Attorney, Agent, or Firm* — Brinks Gilson & Lione

(57) ABSTRACT

The present invention relates to pyridazine compounds of formulae I or II and the salts and N-oxides thereof,

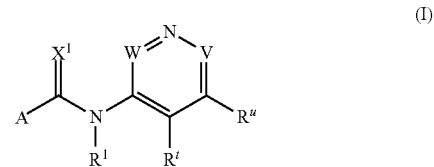

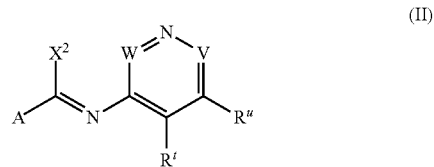

wherein
A is a substituted or unsubstituted oxazole or thiazole or imidazole radical;
V is C(R$^v$) or N; W is C(R$^w$) or N; with the proviso that either V or W is N; R$^t$, R$^u$, R$^v$, R$^w$ are H, halogen, C$_1$-C$_4$-alkyl and the like; X$^1$ is S, O or NR$^{1a}$, wherein R$^{1a}$ is selected H, C$_1$-C$_{10}$-alkyl and the like; X$^2$ is OR$^{2a}$, NR$^{2b}$R$^{2c}$, S(O)$_m$R$^{2d}$, wherein m is 0, 1 or 2, R$^{2a}$ is C$_1$-C$_4$-alkyl, C$_1$-C$_4$-haloalkyl and the like, R$^{2b}$, R$^{2c}$ are H, C$_1$-C$_4$-alkyl, C$_1$-C$_4$-haloalkyl and the like, or R$^{2b}$ and R$^{2c}$ together with the nitrogen atom to which they are bound form a heterocycle, and R$^{2d}$ is C$_1$-C$_4$-alkyl, C$_1$-C$_4$-haloalkyl, C$_3$-C$_6$-cycloalkyl and the like; and R$^1$ is H, CN, C$_1$-C$_{10}$-alkyl and the like.
The present invention further relates to a method for controlling invertebrate pests, to a method for protecting plant propagation material and/or the plants which grow therefrom, to plant propagation material, comprising at least one compound according to the present invention, to a method for treating or protecting an animal from infestation or infection by parasites and to an agricultural composition containing at least one compound according to the present invention.

23 Claims, No Drawings

(51) Int. Cl.
| | | |
|---|---|---|
| A01N 43/58 | (2006.01) | |
| A01N 43/76 | (2006.01) | |
| A01N 43/78 | (2006.01) | |
| C07D 403/12 | (2006.01) | |
| C07D 413/12 | (2006.01) | |

(56) References Cited

U.S. PATENT DOCUMENTS

| | | |
|---|---|---|
| 2006/0069132 A1 | 3/2006 | Armel et al. |
| 2007/0203148 A1 | 8/2007 | Dunkel et al. |
| 2007/0275980 A1 | 11/2007 | Yoshida et al. |
| 2008/0033513 A1 | 2/2008 | Man et al. |
| 2008/0058389 A1 | 3/2008 | Dunkel et al. |
| 2009/0163516 A1 | 6/2009 | Dunkel et al. |
| 2009/0176844 A1 | 7/2009 | Dunkel et al. |
| 2009/0247586 A1 | 10/2009 | Dunkel et al. |
| 2009/0286800 A1 | 11/2009 | Cheruvallath et al. |

FOREIGN PATENT DOCUMENTS

| | | |
|---|---|---|
| CN | 1927838 | 3/2007 |
| CN | 101062916 | 10/2007 |
| CN | 101062919 | 10/2007 |
| EP | 0 419 944 | 4/1991 |
| EP | 0573883 | 12/1993 |
| EP | 0606175 | 7/1994 |
| EP | 0 891 975 | 1/1999 |
| EP | 1 188 745 | 3/2002 |
| EP | 2 263 455 | 12/2010 |
| JP | 10195072 | 7/1998 |
| JP | 2001159610 | 6/2001 |
| JP | 2001348378 | 12/2001 |
| JP | 2004-269515 | 9/2004 |
| JP | 2004331541 | 11/2004 |
| JP | 2005-532367 | 10/2005 |
| JP | 2006/520373 | 9/2006 |
| JP | 2007/77106 | 3/2007 |
| JP | 2008-285482 | 11/2008 |
| WO | WO 98/54154 | 12/1998 |
| WO | WO 99/48868 | 9/1999 |
| WO | WO 00/29398 | 5/2000 |
| WO | WO 01/00575 | 1/2001 |
| WO | WO 02/070483 | 9/2002 |
| WO | WO 02/094791 | 11/2002 |
| WO | WO 03/037900 | 5/2003 |
| WO | WO 03/106427 | 12/2003 |
| WO | WO 2004/017908 | 3/2004 |
| WO | WO 2004/035545 | 4/2004 |
| WO | WO 2004/046129 | 6/2004 |
| WO | WO 2004/076458 | 9/2004 |
| WO | WO 2004/080999 | 9/2004 |
| WO | WO 2004/106324 | 12/2004 |
| WO | WO 2005/040152 | 5/2005 |
| WO | WO 2005/073165 | 5/2005 |
| WO | WO 2005/074686 | 8/2005 |
| WO | WO 2005/075411 | 8/2005 |
| WO | WO 2006/015860 | 2/2006 |
| WO | WO 2006/045522 | 5/2006 |
| WO | WO 2006/074445 | 7/2006 |
| WO | WO 2006/133926 | 12/2006 |
| WO | WO 2007/046548 | 4/2007 |
| WO | WO 2007/046550 | 4/2007 |
| WO | WO 2007/065664 | 6/2007 |
| WO | WO 2007/068373 | 6/2007 |
| WO | WO 2007/068375 | 6/2007 |
| WO | WO 2007/068377 | 6/2007 |
| WO | WO 2007/085188 | 8/2007 |
| WO | WO 2007/121687 | 11/2007 |
| WO | WO 2007/139856 | 12/2007 |
| WO | WO 2007/139860 | 12/2007 |
| WO | WO 2008/116898 | 10/2008 |
| WO | WO 2009/027393 | 3/2009 |
| WO | WO 2009/086303 | 7/2009 |
| WO | WO 2010/017047 | 2/2010 |
| WO | WO 2010/023277 | 3/2010 |
| WO | WO 2010/034737 | 4/2010 |
| WO | WO 2010/034738 | 4/2010 |
| WO | WO 2011/003793 | 1/2011 |
| WO | WO 2011/009804 | 1/2011 |

OTHER PUBLICATIONS

Persson, Tobias, et al., "Pyrazole carboxamides and carboxylic acids as protein kinase inhibitors in aberrant eukaryotic signal transduction: induction of growth arrest in MCF-7 cancer cells", Organic & Biomolecular Chemistry, 2007, pp. 3963-3970, vol. 5.

Sharlow et al., "Development and Implementation of a Miniaturized High-Throughput Time-Resolved Fluorescence Energy Transfer Assay to Identify Small Molecule Inhibitors of Polo-Like Kinase 1," ASSAY and Drug Development Technologies, vol. 5, No. 6, (2007), pp. 723-735.

Office Action dated Jan. 16, 2013, from U.S. Appl. No. 13/120,052, filed Jul. 20, 2011.

Office Action dated May 21, 2013, from U.S. Appl. No. 13/382,229, filed Jan. 4, 2012.

Office Action dated Nov. 21, 2012, from U.S. Appl. No. 16/674,991, filed Feb. 24, 2010.

Office Action dated May 8, 2013, from U.S. Appl. No. 13/386,473, filed Jan. 23, 2012.

U.S. Environmental Protection Agency, "Insect Repellents: Use and Effectiveness", <http://cfpub.epa.gov/oppref/insect/>, Updated Apr. 10, 2013, p. 1-2.

Merriam-Webster, "Pest", <http://www.merriam-webster.com/dictionary/pest>, © 2013, p. 1-4.

National Wildlife Federation, "Invertebrates", <http://www.nwf.org/wildlife/wildlife-library/invertebrates.aspx>, © 1996-2012, p. 1-2.

Pest Control Methods, "Pest control methods: Natural vs. Chemical", <http://www.pestcontrolmethods.org/>, © 2012, p. 1-4.

Britannica Online Encyclopedia, "Arthropod", <http://www.britannica.com/EBchecked/topic/36943/arthropod>, 2013, p. 1-5.

Texas A&M Agrilife Extension, "Order Homoptera", <https://insects.tamu.edu/fieldguide/orders/homoptera.html>, 1999, p. 1.

Cranshaw et al., "Spider Mites", Colorado State University Extension, Fact Sheet No. 5.507, Insect Series: Home and Garden, Nov. 2006, p. 1-3.

Technicide, "Pest Control", <http://technicide.com/Pest-Control>, © 2006, p. 1-2.

Buzzle, "Wasp Insect Control: Wasp Traps and Repellent", <http://www.buzzle.com/articles/wasp-insect-control-wasp-traps-and-repellent.htrnb-, Dec. 8, 2007, p. 1-2.

Bayhan, E., et al., "Effect of temperature on development, morality fecundity and reproduction of *Aphis rumicis* L. (Homoprtera: Aphididae) on broadleaf dock (*Rumex obtusifolius*) and Swiss chad (*Beta vulgaris vulgaris* var. cida)", J. Pest Sci., 2006, p. 57-61 vol. 79.

Bayhan, E, et al., "Effect of temperature on development, morality fecundity and reproduction of *Aphis rumicis* L. (Homoprtera: Aphididae) on broadleaf dock (*Rumex obtusifolius*) and Swiss chad (*Beta vulgaris vulgaris* var. cida)", J. Pest Sci., 2006, p. 57-61 vol. 79.

Office Action dated Dec. 23, 2013, from U.S. Appl. No. 13/386,473, filed Jan. 23, 2012.

Shelton, M.D., et al., "Effects of Weeds on the Diversity and Abundance of Insects in Soybeans", Environmental Entomology, Apr. 1983, pp. 296-298, vol. 12, No. 2.

Final Office Action dated Dec. 9, 2014, from U.S. Appl. No. 13/386,473.

PYRIDAZINE COMPOUNDS FOR CONTROLLING INVERTEBRATE PESTS

This application is a National Stage application of International Application No. PCT/EP2010/059333, filed Jul. 1, 2010, which claims the benefit of U.S. Provisional Application No. 61/223,100 filed Jul. 9, 2009, the entire contents of which are hereby incorporated herein by reference.

The present invention relates to pyridazine compounds which are useful for combating or controlling invertebrate pests, in particular arthropod pests. The invention further relates to a method for controlling invertebrate pests by using these compounds. The invention further relates to a method for protecting plant propagation material and/or the plants which grow therefrom by using these compounds. The present invention further relates to plant propagation material and to an agricultural or veterinary composition comprising said compounds.

BACKGROUND OF THE INVENTION

Invertebrate pests and in particular arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

EP 0419944 describes oxazole- and thioxazolescarboxilic acides derivatives and their use as herbicide is mentioned.

WO 2007/068373, WO 2007/068375 and WO 2007/068377 describe derivatives of N-aryl- and N-hetarylamides, derived from carboxylic acids comprising a 5- or 6-membered carbocycle or heterocycle. These compounds are mentioned to be useful for controlling micro-organisms.

WO 2005/074686 and WO 2005/075411 describe derivatives of N-arylamides which are mentioned to be useful in control of micro-organismus such as fungi, bacteria in the phyto-protection.

WO 2004/106324, WO 2004/035545 and WO 2005/040152 describe derivatives of N-aryl- and N-hetarylamides, derived from carboxylic acids comprising a 5-membered heterocycle. These compounds are mentioned to be useful as herbicides.

WO 2006/074445 describes biologically active hetero pyrrole analogs such as imidazoles, thiazoles, oxazoles, and pyrazoles; their pharmaceutical preparation and their therapeutically administration methods are mentioned.

WO 2003/106427, WO 2004/046129 and JP 2007-77106 describe derivatives of N-arylamides, derived from Pyridazine carboxylic acids. These compounds are mentioned to be useful for combating invertebrate pests.

WO 2001/00575 describes derivatives of N-aryl- and N-hetarylamides, derived from carboxylic acids comprising a 5- or 6-membered heterocycle carrying a further amide-derived function in ortho-position. These compounds are mentioned to be useful as insecticides.

WO 2005/073165 describes derivatives of N-aryl- or N-hetarylamides, derived from carboxylic acids comprising phenyl or a heterocycle, wherein the N-bound cycle carries a further amide-derived function in meta-position. These compounds are mentioned to be useful as insecticides.

It is an object of the present invention to provide compounds that have a good pesticidal activity, in particular insecticidal activity, and show a broad activity spectrum against a large number of different invertebrate pests, especially against difficult to control insects.

It has been found that these objectives can be achieved by compounds of the formulae I and II, as defined below, and by their salts and N-oxides, in particular their agriculturally or veterinarily acceptable salts.

In a first aspect the present invention relates to Pyridazine compounds of formulae I or II and the salts and N-oxides thereof,

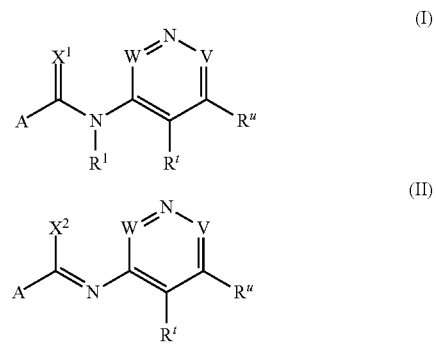

wherein
A is an oxazole or thiazole or imidazole radical of formulae A1, A2 or A3 oxazole,

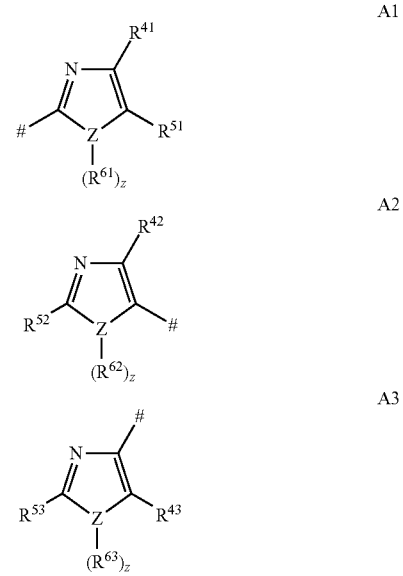

wherein
# denotes the binding site to the remainder of formulae I or II, and wherein
$R^{41}$, $R^{42}$, $R^{43}$ ands $R^{51}$ are independently of each other selected from hydrogen, halogen, CN, $NO_2$, $C_2$-$C_{10}$-alkenyl and $C_2$-$C_{10}$-alkynyl, wherein the 3 last mentioned radicals may be unsubstituted, may be partially or fully halogenated or may carry 1, 2 or 3 identical or different substituents $R^x$, or wherein $R^{41}$, $R^{42}$, $R^{43}$ and $R^{51}$ are further selected from $OR^a$, $C(Y)R^b$, $C(Y)OR^c$, $S(O)_mR^d$, $NR^eR^f$, heterocyclyl, heteroaryl, $C_3$-$C_{10}$-cycloalkyl, $C_5$-$C_{10}$-cycloalkenyl and phenyl, wherein the five last mentioned radicals may be unsubstituted or may carry 1, 2, 3, 4 or 5 identical or different substituents $R^x$, wherein m is 0, 1, 2 and wherein $R^{52}$, $R^{53}$ are selected from hydrogen, halogen, CN, $NO_2$, $C_1$-$C_{10}$-alkyl, $C_2$-$C_{10}$-alkenyl and $C_2$-$C_{10}$-alkynyl, wherein the 3 last mentioned radicals may be unsubstituted, may be partially or fully halogenated or may carry 1, 2 or 3 identical or different substituents $R^x$, or wherein $R^{52}$, $R^{53}$ are further selected from $OR^a$, $C(Y)R^b$, $C(Y)OR^c$, $S(O)_mR^d$, $NR^eR^f$, heterocyclyl, heteroaryl, $C_3$-$C_{10}$-cycloalkyl, $C_5$-$C_{10}$-cycloalkenyl and phenyl, wherein the five last mentioned radicals may be unsubstituted or may carry 1, 2, 3, 4 or 5 identical or different substituents $R^x$, wherein m is 0, 1 or 2, and wherein $R^{61}$, $R^{62}$, $R^{63}$ if present are selected from hydrogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^{61}$, $R^{62}$, $R^{63}$ if present are further selected from $OR^a$, $C(Y)R^b$, $C(Y)OR^b$, $S(O_m)R^d$, $NR^eR^f$, $C(Y)NR^gR^h$, $S(O)_mNR^eR^f$, $C(Y)NR^iNR^eR^f$, heterocyclyl, heterocyclyl-$C_1$-$C_5$-alkyl, heteroaryl, heteroaryl-$C_1$-$C_5$-alkyl, $C_3$-$C_{10}$-cycloalkyl, $C_3$-$C_{10}$-cycloalkenyl, $C_5$-$C_{10}$-cycloalkenyl-$C_1$-$C_5$-alkyl, phenyl, phenyl-$C_1$-$C_5$-alkyl, $C_1$-$C_5$-alkylen-$OR^a$, $C_1$-$C_5$-alkylen-CN, $C_1$-$C_5$-alkylen-$C(Y)R^b$, $C_1$-$C_6$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen$S(O)_mR^d$, $C_1$-$C_5$-alkylen-$S(O)_mNR^aR^f$, $C_1$-$C_5$-alkylen-$C(Y)NR^iNR^eR^f$, wherein the last nineteen mentioned radicals may be unsubstituted or may carry 1, 2, 3, 4 or 5 identical or different substituents $R^x$ or $R^y$ and wherein m is 0, 1 or 2;

Z is O or S for z=0 or Z is N for z=1;
V is $C(R^v)$ or N;
W is $C(R^w)$ or N;
with the proviso that either V or W is N;
$R^t$, $R^u$, $R^v$ and $R^w$ are independently of each other selected from hydrogen, halogen, $C_1$-$C_4$-alkyl, $C_1$-$C_3$-haloalkyl, $C_1$-$C_4$-alkoxy, $C_1$-$C_3$-haloalkoxy, $C_1$-$C_3$-haloalkylthio, $C_1$-$C_4$-alkylsulfinyl, $C_1$-$C_3$-haloalkylsulfinyl, $C_1$-$C_4$-alkylsulfonyl, $C_1$-$C_3$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

$X^1$ is S, O or $NR^{1a}$, wherein $R^{1a}$ is selected from hydrogen, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, phenyl, hetaryl, heterocyclyl, phenyl-$C_1$-$C_4$-alkyl, hetaryl-$C_1$-$C_4$-alkyl, heterocyclyl-$C_1$-$C_4$-alkyl, wherein the ring in, the six last mentioned, radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$X^2$ is $OR^{2a}$, $NR^{2b}R^{2c}$, $S(O)_mR^{2d}$, wherein, m is 0, 1 or 2, wherein $R^{2a}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl, heterocyclyl-$C_1$-$C_4$-alkyl, wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy, and wherein $R^{2b}$, $R^{2u}$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, hetaryl-$C_1$-$C_4$-alkyl and heterocyclyl-$C_1$-$C_4$-alkyl, wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-alkoxy and $C_1$-$C_4$-haloalkoxy, or $R^{2b}$ and $R^{2c}$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from halogen, cyano, nitro, $C_1$-$C_4$-haloalkyl, $C_1$-$C_4$-alkoxy and $C_1$-$C_4$-haloalkoxy and wherein $R^{2d}$ is selected from $C_1$-$C_4$-alkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^1$ is hydrogen, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_2$-$C_{10}$-alkenyl, $C_2$-$C_{13}$-haloalkenyl, $C_2$-$C_{10}$-alkynyl, $C_3$-$C_{10}$-haloalkynyl, $OR^a$, $C(Y)R^b$, $C(Y)OR^g$, $S(O)_2R^d$, $NR^eR^f$, $C(Y)NR^gR^h$, $S(O)_mNR^eR^f$, $C(Y)NR^iNR^eR^f$, phenyl, hetaryl, heterocyclyl, $C_1$-$C_6$-alkylen-$OR^a$, $C_1$-$C_6$-alkylen-CN, hetaryl-$C_1$-$C_6$-alkyl, heterocyclyl-$C_1$-$C_6$-alkyl, $C_3$-$C_{10}$-cycloalkyl-$C_1$-$C_6$-alkyl, $C_1$-$C_6$-alkylen-$C(Y)R^b$, $C_1$-$C_6$-alkylen-$C(Y)OR^g$, $C_1$-$C_5$-alkylen-$NR^eR^f$, $C_1$-$C_6$-alkylen-$C(Y)NR^gR^h$, $C_1$-$C_6$-alkylen-$S(O)_2R^d$, $C_1$-$C_6$-alkylen$S(O)$—, $NR^eR^f$, $C_1$-$C_6$-alkylen-$C(Y)NR^iNR^eR^f$, wherein the last sixteen mentioned radicals may be unsubstituted or may carry 1, 2, 3, 4 or 5 identical or different substituents $R^x$ or $R^y$ and wherein m is 0, 1 or 2;

Y is O or S;

$R^a$, $R^b$, $R^c$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkyl methyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkyl methyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl, wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$, $R^h$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl and hetaryl-$C_1$-$C_4$-alkyl, heterocyclyl-$C_1$-$C_4$-alkyl, wherein the ring in the six last mentioned radicals may be unsubstituted or may carry 1, 2, 3, 4 or substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^i$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^x$ are independently of each other selected from cyano, nitro, $C_1$-$C_4$-alkoxy, $C_1$-$C_4$-haloalkoxy, $C_1$-$C_4$-haloalkylthio, $C_1$-$C_4$-haloalkylsulfinyl, $C_1$-$C_4$-alkylsulfonyl, $C_1$-$C_4$-haloalkylsulfonyl, $C_1$-$C_{10}$-alkylcarbonyl, $C_3$-$C_6$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicats $R^y$; and wherein $R^y$ is selected from halogen, cyano, nitro, $C_1$-$C_4$-alkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl.

A further aspect of the present invention relates to a method for controlling invertebrate pests which method comprises treating the pests, their food supply, their habitat or their breeding ground or a plant, seed, soil, area, material or environment in which the pests are growing or may grow, or the materials, plants, seeds, soils, surfaces or spaces, to be protected from pest attack or infestation with a pesticidally effective amount of a pyridazine compound of formulae I or II according to the present invention or a salt or an N-oxide thereof.

A further aspect of the present invention relates to a method for protecting plant propagation material and/or the plants which grow therefrom, which method comprises treating the plant propagation material with a pesticidally effective amount of a pyridazine compound of the formulae I or II according to the present invention or an agriculturally acceptable salt or an N-oxide thereof.

A further aspect of the present invention relates to plant propagation material, comprising at least one compound of formulae I or II according to the present invention and/or an agriculturally acceptable salt or an N-oxide thereof.

A further aspect of the present invention relates to a method for treating or protecting an animal from infestation or infection by parasites which comprises bringing the animal in contact with a parasiticidally effective amount of a compound of the formulae I or II according to the present invention or a veterinarily acceptable salt or an N-oxide thereof. Bringing the animal in contact with the compound I or II, its salt or the veterinary composition of the invention means applying or administering it to the animal.

A further aspect of the present invention relates to an agricultural composition containing at least one compound of formulae I or II according to the present invention and/or an agriculturally acceptable salt or an N-oxide thereof and at least one liquid or solid carrier.

The radicals attached to the backbone of the compounds of formulae I or II may contain one or more centers of chirality. In this case the compounds of the formulae I or II are present in the form of different enantiomers or diastereomers, depending on the substituents. Compounds of formula II additionally exist as cis- or trans-isomers with respect to the N=C axis. The present invention relates to every possible stereoisomer of the compounds of formulae I or II, i.e. to single enantiomers or diastereomers, as well as to mixtures thereof.

The compounds of formulae I or II may be amorphous or may exist in one or more different crystalline states (polymorphs) which may have different macroscopic properties such as stability or show different biological properties such as activities. The present invention relates to amorphous and crystalline compounds of formulae I or II, mixtures of different crystalline states of the respective compound I or II, as well as amorphous or crystalline salts thereof.

Salts of the compounds of the formulae I or II are preferably agriculturally and veterinarily acceptable salts. They can be formed in a customary manner, e.g. by reacting the compound with an acid of the anion in question if the compound of formulae I or II has a basic functionality.

Agriculturally useful salts of the compounds of formulae I and II encompass especially the acid addition salts of those acids whose cations and anions, respectively, have no adverse effect on the pesticidal action of the compounds of formulae I or II.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formulae I and II with an acid of the corresponding anion, preferably of hydrochloric acid, hydrobromic acid, sulfuric acid, phosphoric acid or nitric acid.

Veterinarily acceptable salts of the compounds of formulae I and II encompass especially the acid addition salts which are known and accepted in the art for the formation of salts for veterinary use. Suitable acid addition salts, e.g. formed by compounds of formulae I or II containing a basic nitrogen atom, e.g. an amino group, include salts with inorganic acids, for example hydrochlorids, sulphates, phosphates, and nitrates and salts of organic acids for example acetic acid, maleic acid, e.g. the monoacid salts or diacid salts of maleic acid, dimaleic acid, fumaric acid, e.g. the monoacid salts or diacid salts of fumaric acid, difumaric acid, methane sulfenic acid, methane sulfonic acid, and succinic acid.

The term "N-oxide" includes any compound of formulae I or II which has at least one tertiary nitrogen atom that is oxidized to an N-oxide moiety.

The term "invertebrate pest" as used herein encompasses animal populations, such as insects, arachnids and nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat. Protoc. 2007; 2(5):1225-35, Curr. Opin. Chem. Biol. 2006 October; 10(5):487-91. Epub 2006 Aug. 28, Biomaterials. 2001 March; 22(5):405-17, Bioconjug. Chem. 2005 January-February; 16(1):113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under, the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally, known to the person skilled in the art and are described, for example, in the publications mentioned above.

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of an alkyl group are methyl, ethyl, n-propyl, isopropyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dinnethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylpentyl, n-octyl, 1-methyloctyl, 2-methylheptyl, 1-ethylhexyl, 2-ethylhexyl, 1,2-dimethylhexyl, 1-propylpentyl and 2-propylpentyl.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "haloalkyl" as used herein and in the haloalkyl moieties of haloalkoxy, haloalkylthio, haloalkylcarbonyl, haloalkylsulfonyl and haloalkylsulfinyl, denotes in each case a straight-chain or branched alkyl group having usually from 1 to 10 carbon atoms, frequently from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bound via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group having from 1 to 10 carbon atoms, frequently from 1 to 4 carbon atoms, preferably 1 to 3 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and the like.

The term "cycloalkyl" as used herein and in the cycloalkyl moieties of cycloalkoxy and cycloalkylmethyl denotes in each case a mono- or bicyclic cycloaliphatic radical having usually from 3 to 10 carbon atoms or 3 to 6 carbon atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "halocycloalkyl" as used herein and in the halocycloalkyl moieties of halocycloalkylmethyl denotes in each case a mono- or bicyclic cycloaliphatic radical having usually from 3 to 10 carbon atoms or 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "alkenyl" as used herein denotes in each case a singly unsaturated hydrocarbon radical having usually 2 to 10, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkynyl" as used herein denotes in each case a singly unsaturated hydrocarbon radical having usually 2 to 10, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "alkoxyalkyl" as used herein refers to alkyl usually comprising 1 to 4 carbon atoms, wherein 1 carbon atom carries an alkoxy radical usually comprising 1 to 10, in particular 1 to 4, carbon atoms as defined above. Examples are $CH_2OCH_3$, $CH_2$—$OC_2H_5$, n-propoxymethyl, $CH_2$—OCH($CH_3$)$_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methylpropoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "alkylcarbonyl" (alkyl-C(=O)—), as used herein refers to a straight-chain or branched saturated alkyl group as define above comprising 1 to 10 carbon atoms (=$C_1$-$C_{10}$-alkylcarbonyl), preferably 1 to 4 carbon atoms (=$C_1$-$C_4$-alkylcarbonyl) attached through the carbon atom of the carbonnyl group at any position in the alkyl group.

The term "haloalkylcarbonyl" as used herein refers to, an alkylcarbonyl group as defined above wherein the hydrogen atoms are partially or fully substituted by fluorine, chlorine, bromine and/or iodine.

The term "alkylthio "(also alkylsulfanyl or alkyl-S—)" as used herein refers to a straight-chain or branched saturated alkyl group comprising 1 to 10 carbon atoms (=$C_1$-$C_{10}$-alkylthio), preferably 1 to 4 carbon atoms (=$C_1$-$C_4$-alkylthio) as defined above, which is attached via a sulfur atom at any position in the alkyl group.

The term "haloalkylthio" as used herein refers to an alkylthio group as defined above wherein the hydrogen atoms are partially or fully substituted by fluorine, chlorine, bromine and/or iodine.

The term "alkylsulfinyl" (also alkylsulfoxyl or alkyl-S(=O)—), as used herein refers to a straight-chain or branched saturated alkyl group as define above comprising 1 to 10 carbon atoms (=$C_1$-$C_{10}$-alkylsulfinyl), preferably 1 to 4 carbon atoms (=$C_1$-$C_4$-alkylsulfinyl) attached through the sulfur atom of the sulfinyl group at any position in the alkyl group.

The term "haloalkylsulfinyl" as used herein refers to an alkylsulfinyl group as defined above wherein the hydrogen atoms are partially or fully substituted by fluorine, chlorine, bromine and/or iodine.

The term "alkylsulfonyl" (also alkyl-S(=O)$_2$—) as used herein refers to a straight-chain or branched saturated alkyl group comprising 1 to 10 carbon atoms (=$C_1$-$C_{10}$-alkylsulfonyl), preferably 1 to 4 carbon atoms (=$C_1$-$C_4$-alkylsulfonyl), as defined above, which is attached via the sulfur atom of the sulfonyl group at any position in the alkyl group.

The term "haloalkylsulfonyl" as used herein refers to an alkylsulfonyl group as defined above wherein the hydrogen atoms are partially or fully substituted by fluorine, chlorine, bromine and/or iodine.

The term "heterocyclyl" includes in general 5-, 6-, 7- or 8-membered monocyclic heterocyclic radicals and 8 to 10 membered bicyclic heterocyclic radicals, the mono- and bicyclic radicals may be saturated, partially unsaturated or unsaturated. The mono- and bicyclic heterocyclic radicals usually comprise 1, 2, 3 or 4 heteroatoms selected from N, O and S as ring members.

Examples of saturated or unsaturated 5- or 6-membered heterocyclic radicals comprise saturated or unsaturated, non-aromatic heterocyclic rings, such as pyrrolidinyl, pyrazolinyl, pyrazolidinyl, imidazolinyl, pyrrolinyl, pyrazolidinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, dihydrothiopyranyl, tetrahydrothiopyranyl, morpholinyl, thiazinyl and the like. Examples for heterocyclic ring also comprising 1 or 2 carbonyl groups as ring members comprise pyrrolidin-2-only, pyrrolidin-2,5-dionyl, imidazolidin-2-only, oxazolidin-2-only, thiazolidin-2-only and the like.

The term "hetaryl" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2, 4-triazolyl and tetrazolyl, i.e. 1H- or 2H-tetrazolyl.

The term "hetaryl" also includes bicyclic 8- to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "phenylalkyl" and "phenoxyalkyl" refers to phenyl or phenoxy, respectively, which are bound via an alkyl group, in particular a methyl group (=hetarylmethyl), to the remainder of the molecule, examples including benzyl, 1-phenylethyl, 2-phenylethyl, 2-phenoxyethyl and the like.

The terms "heterocyclylalkyl" and "hetarylalkyl" refers to heterocyclyl or hetaryl, respectively, as defined above which are bound via an alkyl group, in particular a methyl group (=heterocyclylmethyl or hetarylmethyl, respectively), to the remainder of the molecule.

The remarks made below as to preferred embodiments of the variables of the compounds of formulae I or II are valid on their own as well as—preferably—in combination with each other. The remarks made below concerning preferred embodiments of the variables further are valid concerning the compounds of formulae I or II as well as concerning the uses and methods according to the invention and the composition according to the present invention.

A first preferred embodiment of the invention relates to the pyridazine compounds of the formula I, to their salts and to their N-oxides.

Among the compounds of the formula I, preference is given to those compounds, wherein $X^1$ is oxygen. These compounds are hereinafter also referred to as compounds of formula I'.

Among the compounds of the formula I, preference is further given to those compounds, wherein $R^1$ is hydrogen, CN, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $C_1$-$C_4$-alkylene-CN, $OR^a$, $C(Y)R^b$, $C(Y)OR^c$ or $S(O)_2R^d$. Preferably, $R^1$ is hydrogen, $C_1$-$C_{10}$-alkyl, $C_1$-$C_{10}$-haloalkyl, $C_1$-$C_4$-alkylene-CN, heterocyclyl-$C_1$-$C_5$-alkyl, hetaryl-$C_1$-$C_5$-alkyl, $C_1$-$C_5$-alkylen-$OR^a$ or $C_3$-$C_{10}$-cycloalkyl-$C_1$-$C_5$-alkyl. More preferably $R^1$ is hydrogen, $C_1$-$C_4$-alkyl, $C_1$-$C_4$-haloalkyl or $C_1$-$C_4$-alkoxy-$C_1$-$C_4$-alkyl. In particular $R^1$ is hydrogen or $C_1$-$C_3$-alkyl.

Another embodiment of the invention relates to pyridazine compounds of the formula II, to the salts and N-oxides thereof and to the methods and uses of such compounds. In the compounds of the formula II, preference is given to those compounds, wherein $X^2$ in formula II is $OR^{2a}$ or $SR^{2a}$. In these compounds $R^{2a}$ is preferably $C_1$-$C_6$-alkyl, $C_3$-$C_6$-alkenyl, $C_3$-$C_8$-alkynyl, $C_3$-$C_8$-cycloalkylmethyl or $C_1$-$C_4$-alkoxy-$C_1$-$C_{10}$-alkyl. Another embodiment of the invention relates to compounds of the formula II, wherein $X^2$ is $NR^{2b}R^{2c}$. In these compounds $R^{2b}$ and $R^c$ are preferably selected, independently of each other, from $C_1$-$C_6$-alkyl, $C_3$-$C_6$-cycloalkylmethyl or $C_1$-$C_4$-alkoxy-$C_1$-$C_{10}$-alkyl or $R^{2b}$ and $R^{2c}$, together with the nitrogen atom to which they are attached, form a saturated, nitrogen-bound 5- or 6-membered heterocycle which may comprise a further heteroatom selected from O, S and N, e.g. $NR^{2b}R^{2e}$ being 1-pyrrolidinyl, 1-piperidinyl, 1-piperazinyl, 4-morpholinyl or 4-thiomorpholinyl.

Among the compounds of formulae I and II preference is given to those compounds, wherein $R^u$ is selected from hydrogen, halogen, $C_1$-$C_4$-alkyl, $C_1$-$C_3$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl.

Among the compounds of formulae I and II preference is given to those compounds, wherein $R^t$ is selected from hydrogen, halogen, $C_1$-$C_4$-alkyl; $C_1$-$C_3$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl.

Among the compounds of formulae I and II preference is further given to those compounds selected from 4-pyridazine substituted compounds of formulae I.A or II.A

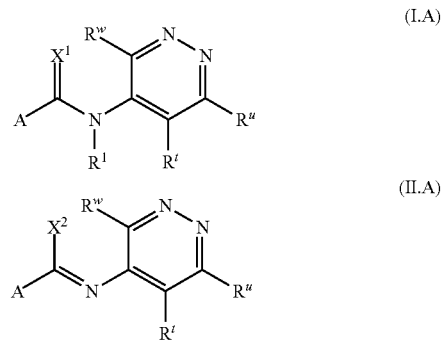

wherein A, $X^1$, $X^2$, $R^1$, $R^t$, $R^u$ and $R^w$ independently from each are as defined herein.

Among the compounds of formulae I and II preference is further given to those compounds, wherein W is $CR^w$ with $R^w$ being hydrogen, i.e. W is CH.

Among the compounds of formulae I and II preference is further given to those compounds selected from 4-pyridazine substituted compounds of formulae I.B or II.B

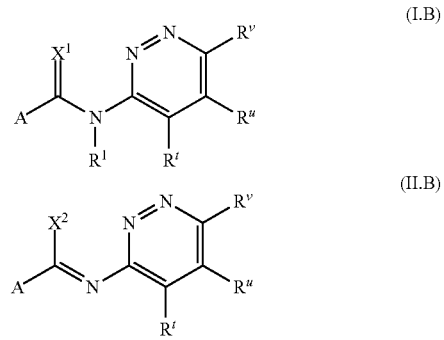

wherein A, $X^1$, $X^2$, $R^1$, $R^t$, $R^u$ and $R^w$ independently from each are as defined herein.

Among the compounds of formulae I and II preference is further given to those compounds, wherein V is $CR^v$ with $R^v$ being hydrogen, i.e. V is CH.

Among the compounds of formulae I and II preference is further given to those compounds, wherein $R^t$, $R^u$ and $R^w$, if present, are selected independently of each other from hydrogen, methyl, difluoromethyl, trifluoromethyl, methoxy, difluoromethoxy or trifluoromethoxy. More preferably, preference is given to those compounds, wherein at least two of the radicals $R^t$, $R^u$, $R^v$ or $R^w$, if present, are hydrogen.

Most particularly, preference is given to those compounds, wherein $R^t$, $R^u$, $R^v$ and $R^w$, if present, are hydrogen.

Another preferred embodiment of the invention relates to pyridazine compounds of formulae I and II, to the salts and N-oxides thereof and to the methods and uses of such compounds, wherein A is a radical A1. Among the compounds, wherein A is A1, preference is given to compounds of the formula I, wherein $X^1$, $R^1$, $R^t$, $R^u$, $R^v$ and $R^w$ are as defined above and in particular have one of the preferred meanings.

Among the compounds of formulae I and II, wherein A is A1, preference is given to those compounds, wherein $R^{41}$ is selected from hydrogen, halogen, CN, $C_1$-$C_4$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{41}$ is further selected from $C_3$-$C_8$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably $R^{41}$ is selected from hydrogen, halogen, CN, $C_1$-$C_4$-alkyl, $C_1$-$C_4$-haloalkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-alkoxy and $C_1$-$C_4$-haloalkoxy. Preferably $R^{41}$ is selected from hydrogen, halogen, CN, $C_1$-$C_4$-haloalkyl, $C_3$-$C_6$-cycloalkyl and $C_3$-$C_6$-halocycloalkyl. More preferably, $R^{41}$ is selected from hydrogen, halogen, $C_1$-$C_4$-alkyl, $C_1$-$C_4$-haloalkyl, $C_3$-$C_6$-cycloalkyl and $C_3$-$C_6$-halocycloalkyl. Most preferably $R^{41}$ is selected from hydrogen, $C_1$-$C_3$-alkyl, $C_1$-$C_3$-haloalkyl and $C_3$-$C_5$-cycloalkyl. Even more preferably $R^{41}$ is hydrogen or $C_1$-$C_3$-alkyl. In particular $R^{41}$ is hydrogen.

Among the compounds of formulae I and II, wherein A is A1, preference is further given to those compounds, wherein $R^{51}$ is selected from hydrogen, halogen, CN, $C_1$-$C_{10}$-alkyl and $C_2$-$C_{13}$-alkenyl, wherein the 2 last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{51}$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably $R^{51}$ is selected from hydrogen, halogen, CN, $C_1$-$C_4$-alkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. Preferably $R^{51}$ is selected from hydrogen, halogen, CN, $C_1$-$C_4$-haloalkyl, $C_3$-$C_5$-cycloalkyl and $C_3$-$C_6$-halocycloalkyl. More preferably, $R^{51}$ is selected from hydrogen, halogen, $C_1$-$C_4$-alkyl, $C_1$-$C_4$-haloalkyl, $C_3$-$C_6$-cycloalkyl and $C_3$-$C_6$-halocycloalkyl. Most preferably $R^{51}$ is selected from hydrogen, $C_1$-$C_3$-alkyl, $C_1$-$C_3$-haloalkyl and $C_3$-$C_5$-cycloalkyl. Even more preferably $R^{51}$ is hydrogen or $C_1$-$C_3$-alkyl. In particular $R^{51}$ is hydrogen.

Among the compounds of formulae I and II, wherein A is A1, preference is further given to those compounds, wherein n $R^{61}$ if present is selected from hydrogen, $C_1$-$C_{10}$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{61}$ if present is further selected from $C_3$-$C_6$-cycloalkyl, $C_3$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably, $R^{61}$ is selected from hydrogen, $C_1$-$C_4$-alkyl, $C_3$-$C_6$-cycloalkyl-$C_1$-$C_4$-alkyl, heterocyclyl-$C_1$-$C_4$-alkyl, $C_1$-$C_4$-alkoxy-$C_1$-$C_4$-alkyl and $C_1$-$C_4$-alkyl-CN. Preferably $R^{61}$ is selected from hydrogen, $C_1$-$C_4$-alkyl, $C_1$-$C_4$-haloalkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably $R^{61}$ if present is hydrogen, $C_1$-$C_4$-alkyl or $C_1$-$C_4$-haloalkyl. In particular $R^{61}$ if present is hydrogen or $C_1$-$C_3$-alkyl.

Examples of suitable radicals A1 are the radicals of formulae A1.a, A1.b, A1.c, A1.d, A1.e, A1.f, A1.g, A1.h, A1.i, A1.k, A1.l, A1.m, A1.n, A1.o, A1.p, A1.q, A1.r, A1.s, A1.t, A1.u, A1.v, A1.w, A1.x, A1.y and A1.z, wherein Z is O and $R^{51}$, $R^{41}$ is a radical as defined in one line of table A. (radicals A1.a1-A1.a81 to A1.z1-A1.z81):

TABLE A

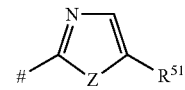

A1.a

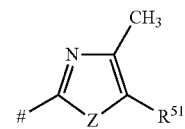

A1.b

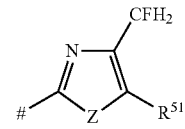

A1.c

A1.d

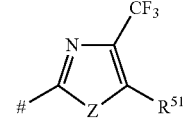

A1.e

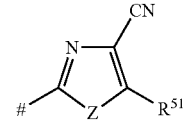

A1.f

TABLE A-continued
| | |
|---|---|
| 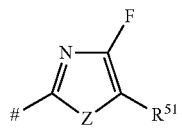 | A1.g |
| 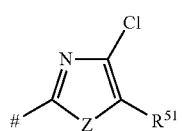 | A1.h |
| 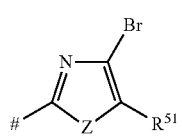 | A1.i |
| 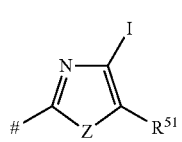 | A1.k |
| 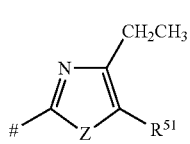 | A1.l |
| 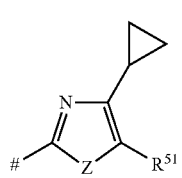 | A1.m |
| 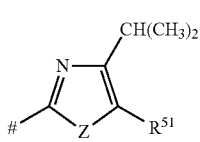 | A1.n |
| 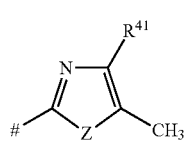 | A1.o |
| 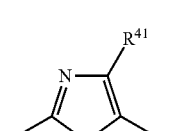 | A1.p |
| 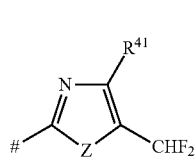 | A1.q |
TABLE A-continued
| | |
|---|---|
| 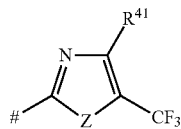 | A1.r |
| 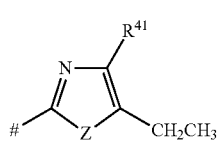 | A1.s |
| 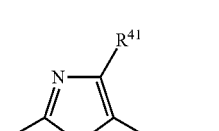 | A1.t |
| 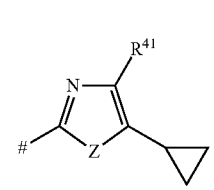 | A1.u |
| 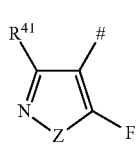 | A1.v |
| 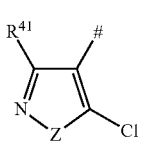 | A1.w |
| 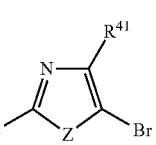 | A1.x |
| 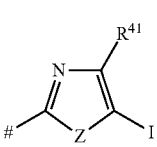 | A1.y |
| 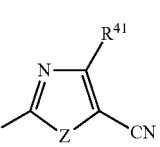 | A1.z |
| line | Radical $R^{61}/R^{51}/R^{41}/R^{62}/R^{52}/R^{53}/R^{63}$ |
|---|---|
| 1 | H |
| 2 | $CH_3$ |

TABLE A-continued

| | |
|---|---|
| 3 | $CH_2CH_3$ |
| 4 | $CH_2CH_2CH_3$ |
| 5 | $CH(CH_3)_2$ |
| 6 | $CH_2CF_3$ |
| 7 | $C(CH_3)_3$ |
| 8 | $C_6H_5$ |
| 9 | 4-Cl—$C_6H_4$ |
| 10 | 4-F—$C_6H_4$ |
| 11 | 2,4-$Cl_2$—$C_6H_3$ |
| 12 | 4-($CH_3O$)-$C_6H_4$ |
| 13 | 2-pyridyl |
| 14 | 5-chloro-2-pyridyl |
| 15 | $CH_2$—$C_6H_5$ |
| 16 | 4-($OCF_3$)—$C_6H_4$ |
| 17 | 4-($SCF_3$)—$C_6H_4$ |
| 18 | 4-($OCHF_2$)—$C_6H_4$ |
| 19 | 4-($CF(CF_3)_2$)—$C_6H_4$ |
| 20 | 4-($SO_2CH_3$)—$C_6H_4$ |
| 21 | 2,6-Cl-4-$CF_3$—$C_6H_2$ |
| 22 | 3-chloro-5-trifluoro-methylpyridine-2-yl |
| 23 | 3-pyridyl |
| 24 | 4-pyridyl |
| 25 | 2-thiazolyl |
| 26 | 4,5-dimethyl-thiazol-2-yl |
| 27 | 4-thiazolyl |
| 28 | 5-thiazolyl |
| 29 | 4-trifluormethyl-thiazol-2-yl |
| 30 | 4-methylthiazol-2-yl |
| 31 | 4-phenylthiazol-2-yl |
| 32 | 5-triazolyl |
| 33 | 3-methyl-triazol-5-yl |
| 34 | 4-chlorobenzyl |
| 35 | 4-nitro-1-pyrazolyl-methyl |
| 36 | 2-imidazolyl |
| 37 | 4-imidazolyl |
| 38 | 5-imidazolyl |
| 39 | 2-oxazolyl |
| 40 | 4-oxazolyl |
| 41 | 5-oxazolyl |
| 42 | 3-isoxazolyl |
| 43 | 4-isoxazolyl |
| 44 | 5-isoxazolyl |
| 45 | 3-methylisoxazol-5-yl |
| 46 | 5-methylisoxazol-3-yl |
| 47 | 3-pyrazolyl |
| 48 | [1,3,4]thiadiazol-2-yl |
| 49 | 5-tetrazolyl |
| 50 | 4-$NO_2$—$C_6H_4$ |
| 51 | 4-$CF_3$—$C_6H_4$ |
| 52 | 2,4-$F_2$—$C_6H_3$ |
| 53 | 3,5-$Cl_2$—$C_6H_3$ |
| 54 | 3,4-$Cl_2$—$C_6H_3$ |
| 55 | 4-$C(CH_3)_3$—$C_6H_4$ |
| 56 | 3-Cl—$C_6H_4$ |
| 57 | 3-F—$C_6H_4$ |
| 58 | 2-F—$C_6H_4$ |
| 59 | 2-$CF_3$—$C_6H_4$ |
| 60 | 2-$CH_3O$—$C_6H_4$ |
| 61 | 3-$CH_3O$—$C_6H_4$ |
| 62 | 3-Cl-4-F—$C_6H_3$ |
| 63 | 3-$NO_2$—$C_6H_4$ |
| 64 | 2-$CH_3$—$C_6H_4$ |
| 65 | 3-$CH_3$—$C_6H_4$ |
| 66 | 4-$CH_3$—$C_6H_4$ |
| 67 | 2-phenyl-$C_6H_4$ |
| 68 | 3-phenyl-$C_6H_4$ |
| 69 | 2-F-4-Cl—$C_6H_3$ |
| 70 | 2,4,6-$Cl_3$—$C_6H_2$ |
| 71 | 2,3,4-$Cl_3$—$C_6H_2$ |
| 72 | 2,6-$F_2$—$C_6H_3$ |
| 73 | $CH_2F$ |
| 74 | $CHF_2$ |
| 75 | $CF_3$ |
| 76 | $CH_2CHF_2$ |
| 77 | $CH_2Cl$ |
| 78 | $CHCl_2$ |
| 79 | $CCl_3$ |
| 80 | $CH_2CHCl_2$ |
| 81 | $CH_2CCl_3$ |
| 82 | Br |
| 83 | Cl |
| 84 | F |

Analogue to the above listed structures, examples of suitable radicals A1 are the radicals of formulae A1.a', A1.b', A1.c', A1.d', A1.e', A1.f', A1.g', A1.h', A1.i', A1.k', A1.l', A1.m', A1.n', A1.o', A1.p', A1.q', A1.r', A1.s', A1.t', A1.u', A1.v', A1.w', A1.x', A1.y' and A1.z', wherein Z is S and $R^{51}$, $R^{41}$ is a radical as defined in one line of table A (radicals A1.a' 1-A1.a' 81 to A1.z' 1-A1.z' 81).

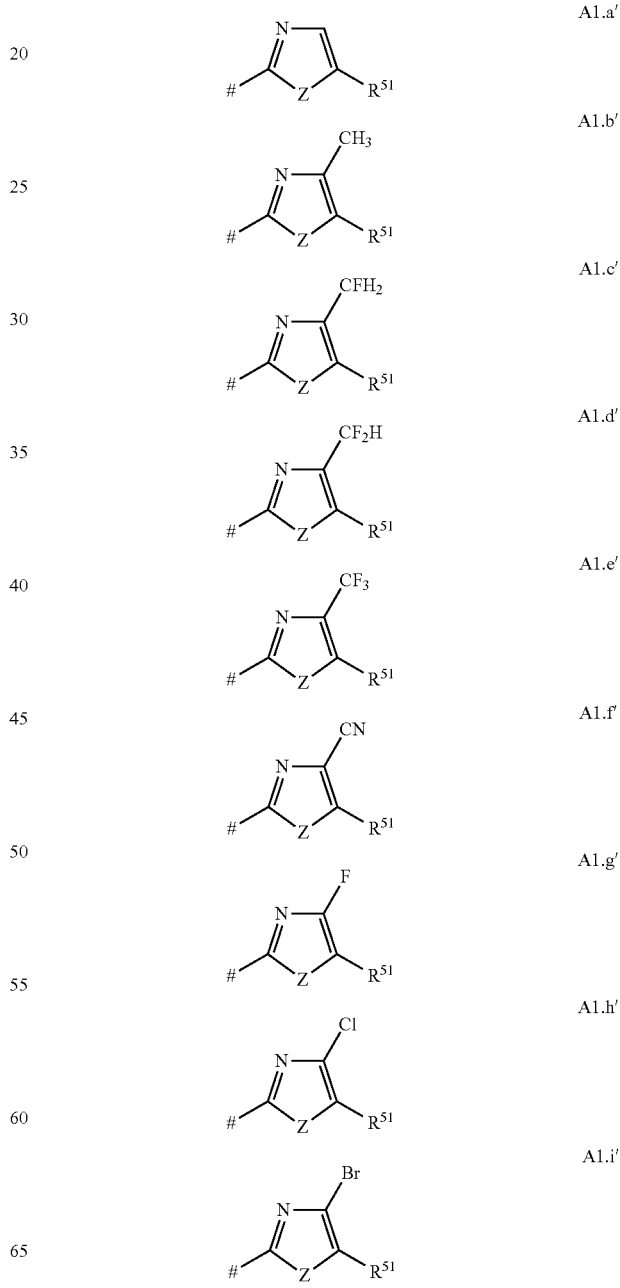

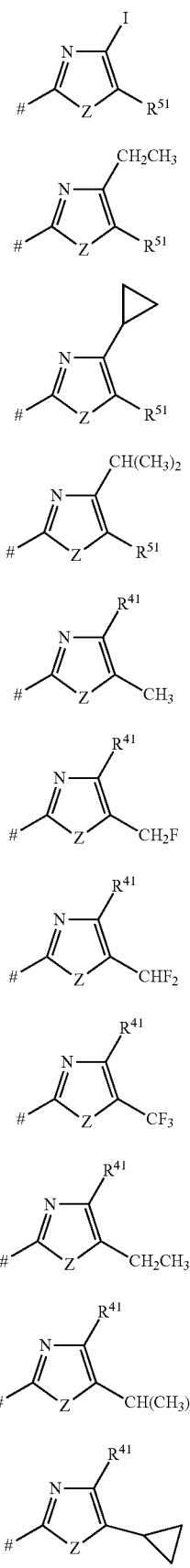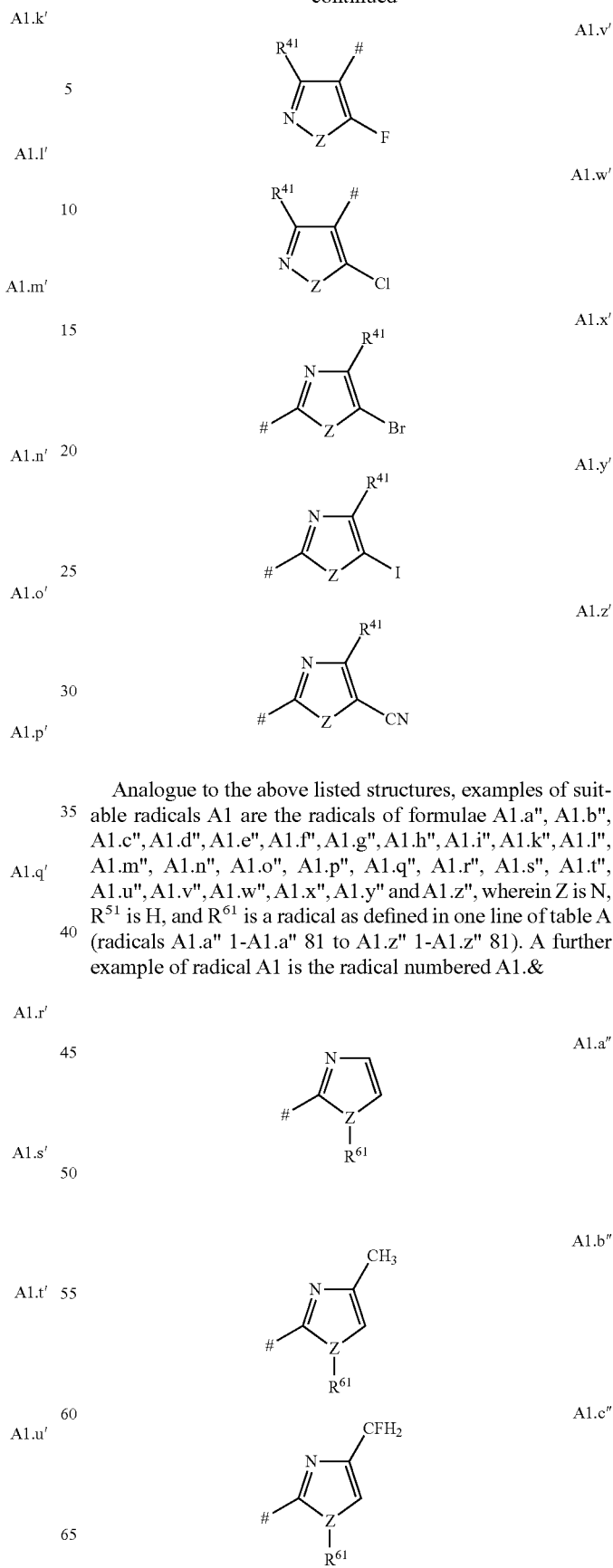
Analogue to the above listed structures, examples of suitable radicals A1 are the radicals of formulae A1.a″, A1.b″, A1.c″, A1.d″, A1.e″, A1.f″, A1.g″, A1.h″, A1.i″, A1.k″, A1.l″, A1.m″, A1.n″, A1.o″, A1.p″, A1.q″, A1.r″, A1.s″, A1.t″, A1.u″, A1.v″, A1.w″, A1.x″, A1.y″ and A1.z″, wherein Z is N, $R^{51}$ is H, and $R^{61}$ is a radical as defined in one line of table A (radicals A1.a″ 1-A1.a″ 81 to A1.z″ 1-A1.z″ 81). A further example of radical A1 is the radical numbered A1.&

| | | | |
|---|---|---|---|
| 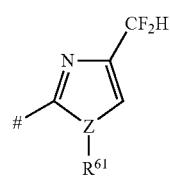 | A1.d″ | 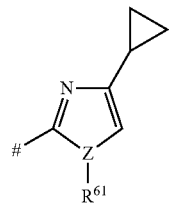 | A1.m″ |
| 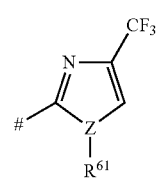 | A1′.e′ | 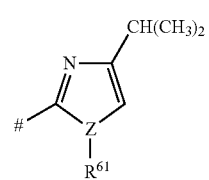 | A1.n″ |
| 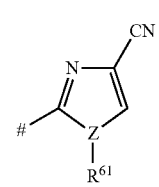 | A1.f″ | 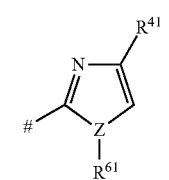 | A1.o″ |
|  | A1.g″ | 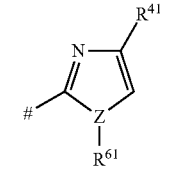 | A1.p″ |
| 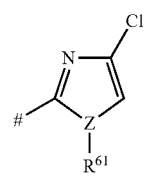 | A1.h″ | 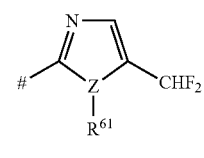 | A1.q″ |
| | | 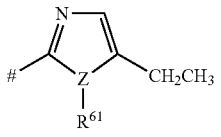 | A1.r″ |
| 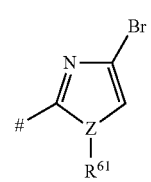 | A1.i″ | 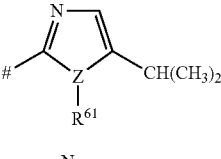 | A1.s″ |
| 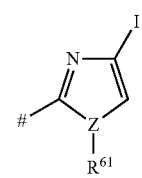 | A1.k″ | 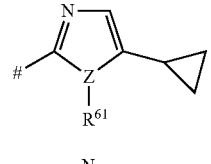 | A1.t″ |
| 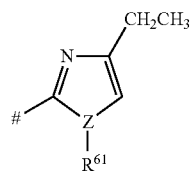 | A1.′l′ | 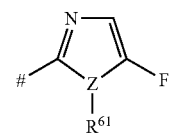 | A1.u″ |
| | | | A1.v″ |

A1.w" 

A1.x" 

A1.y" 

A1.z" 

A1.& 

A further embodiment of the invention relates to pyridazine compounds of formulae I and II, to the salts and N-oxides thereof and to the methods and uses of such compounds, wherein A is a radical A2. Among the compounds of formulae I and II, wherein A is a radical A2, preference is given to compounds of the formulae I or II, wherein $X^1$, $R^1$, $R^t$, $R^u$, $R^v$ and $R^w$ are as defined above and in particular have one of the preferred meanings.

Among the compounds of formulae I and II, wherein A is A2, preference is given to those compounds, wherein $R^{42}$ is selected from hydrogen, halogen, CN, and $C_2$-$C_{10}$-alkenyl, wherein the 2 last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetanjl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{42}$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Among the compounds of formulae I and II, wherein A is A2, preference is given to those compounds, wherein $R^{42}$ is selected from hydrogen, halogen, CN, $C_1$-$C_3$-alkyl and $C_2$-$C_3$-alkenyl, wherein the 2 last mentioned radicals may be unsubstituted, may be partially or fully halogenated or may carry 1, 2 or 3 identical or different substituents selected from $C_1$-$C_3$-alkoxy, $C_1$-$C_3$-haloalkoxy, $C_3$-$C_6$-cycloalkyl, $C_5$-$C_6$-heteroaryl, phenyl and phenoxy, wherein the last three mentioned radicals may be unsubstituted or may carry 1, 2, 3, 4 or 5 radicals selected from halogen, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylsulfonyl and $C_1$-$C_3$-haloalkylsulfonyl, or wherein $R^{42}$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_3$-alkyl, $C_1$-$C_3$-haloalkyl, $C_1$-$C_3$-alkoxy, $C_1$-$C_3$-haloalkoxy, $C_1$-$C_3$-alkylsulfonyl and $C_1$-$C_3$-haloalkylsulfonyl. Preferably $R^{42}$ is selected from hydrogen, halogen, CN, $C_1$-$C_3$-haloalkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_3$-alkyl, $C_1$-$C_3$-haloalkyl, $C_1$-$C_3$-alkoxy and $C_1$-$C_3$-haloalkoxy; in particular $R^{42}$ is selected from hydrogen, halogen, CN, $C_1$-$C_3$-alkyl, $C_1$-$C_3$-haloalkyl, $C_3$-$C_6$-cycloalkyl and $C_3$-$C_6$-halocycloalkyl.

Preferably $R^{42}$ is selected from hydrogen, halogen, CN, $C_1$-$C_4$-alkyl, $C_1$-$C_4$-haloalkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. Preferably $R^{42}$ is selected from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl. More preferably, $R^{42}$ is selected from hydrogen, halogen, $C_1$-$C_4$-alkyl, $C_1$-$C_4$-haloalkyl, $C_3$-$C_6$-cycloalkyl and $C_3$-$C_6$-halocycloalkyl. Most preferably $R^{42}$ is selected from hydrogen, $C_1$-$C_3$-alkyl, $C_1$-$C_3$-haloalkyl and $C_3$-$C_5$-cycloalkyl. Even more preferably $R^{42}$ is hydrogen or $C_1$-$C_3$-alkyl. In particular $R^{42}$ is hydrogen.

Among the compounds of formulae I and II, wherein A is A2, preference is further given to those compounds, wherein $R^{52}$ is selected from hydrogen, halogen, CN, $C_1$-$C_{10}$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{52}$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably $R^{52}$ is selected from hydrogen, halogen, CN, $C_1$-$C_4$-alkyl, $C_1$-$C_4$-haloalkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-alkoxy and $C_1$-$C_4$-haloalkoxy. Preferably, $R^{52}$ is selected from hydrogen, halogen, $C_1$-$C_4$-alkyl, $C_1$-$C_4$-haloalkyl, $C_3$-$C_6$-cycloalkyl and $C_3$-$C_6$-halocycloalkyl. Most preferably $R^{52}$ is selected from hydrogen, $C_1$-$C_3$-alkyl, $C_1$-$C_3$-haloalkyl and $C_3$-$C_5$-cycloalkyl. More preferably $R^{52}$ is hydrogen, $C_1$-$C_4$-alkyl or $C_1$-$C_4$-haloalkyl. Even more preferably $R^{52}$ is hydrogen or $C_1$-$C_3$-alkyl. In particular $R^{52}$ is hydrogen.

Among the compounds of formulae I and II, wherein A is A2, preference is further given to those compounds, wherein $R^{62}$ if present is selected from hydrogen, $C_1$-$C_{10}$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{62}$ if present is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably, $R^{62}$ is selected from hydrogen, $C_1$-$C_4$-alkyl, $C_1$-$C_4$-haloalkyl, $C_3$-$C_6$-cycloalkyl-$C_1$-$C_4$-alkyl, heterocyclyl-$C_1$-$C_4$-alkyl, $C_1$-$C_4$-alkoxy-$C_1$-$C_4$-alkyl and $C_1$-$C_4$-alkyl-CN. Preferably $R^{62}$ if present is selected from hydrogen, $C_1$-$C_4$-alkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably $R^{62}$ if present is selected from hydrogen, halogen, CN, $C_3$-$C_6$-cycloalkyl and $C_3$-$C_6$-halocycloalkyl. In particular $R^{62}$ if present is hydrogen.

Examples of suitable radicals A2 are the radicals of formulae A2.aa, A2.ab, A2.ac, A2.ad, A2.ae, A2.af, A2.ag, A2.ah, A2.ai, A2.ak, A2.al, A2.am, A2.an and A2.ao, wherein Z is O and $R^{52}$ is a radical as defined in one line of table A (radicals A2.aa1-A2.aa81 to A2.ao1-A2.ao81):

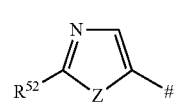  A2.aa

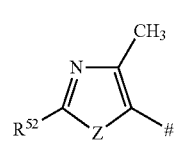  A2.ab

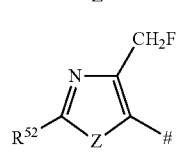  A2.ac

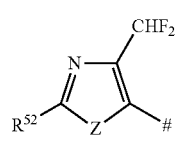  A2.ad

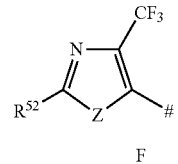  A2.ae

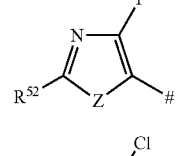  A2.af

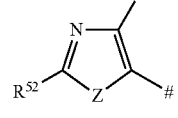  A2.ag

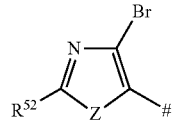  A2.ah

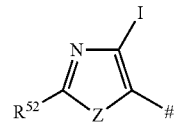  A2.ai

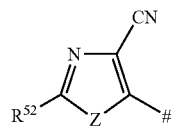  A2.ak

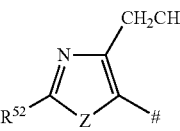  A2.al

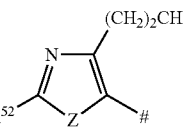  A2.am

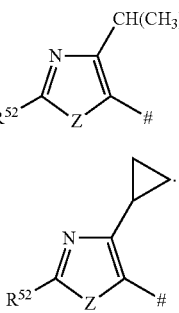  A2.an

A2.ao

Analogue to the above listed structures, examples of suitable radicals A2 are the radicals of formulae A2.aa', A2.ab', A2.ac', A2.ad', A2.ae', A2.af', A2.ag', A2.ah', A2.ai', A2.ak' A2.al', A2.am', A2.an' and A2.ao', wherein Z is S and $R^{52}$ is a radical as defined in one line of table A (radicals A2.aa' 1-A2.aa' 81 to A2.ao' 1-A2.ao' 81).

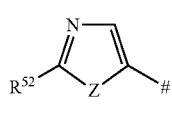  A2.aa'

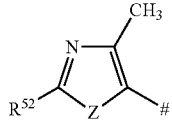  A2.ab'

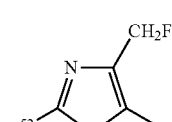  A2.ac'

-continued

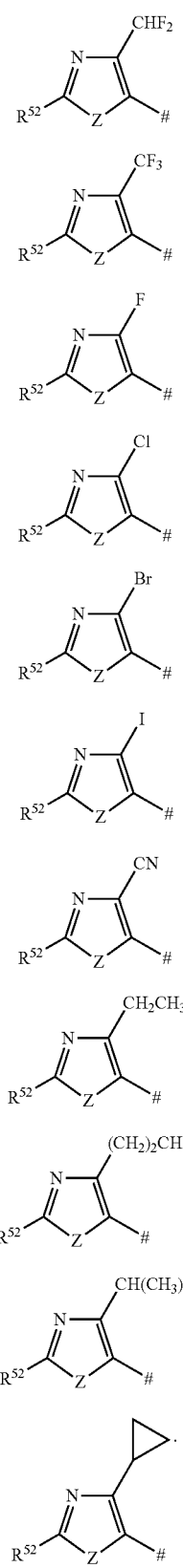

A2.ad'
A2.ae'
A2.af'
A2.ag'
A2.ah'
A2.ai'
A2.ak'
A2.al'
A2.am'
A2.an'
A2.ao'

Analogue to the above listed structures, examples of suitable radicals A2 are the radicats of formulae A2.aa", A2.ab",  A2.ac", A2.ad", A2.ae", A2.af", A2.ag", A2.ah", A2.ai", A2.ak", A2.al", A2.am", A2.an" and A2.ao", wherein Z is NH and $R^{52}$ is a radical as defined in one line of table A (radicals A2.aa" 1-A2.aa" 81 to A2.ao" 1-A2.ao" 81).

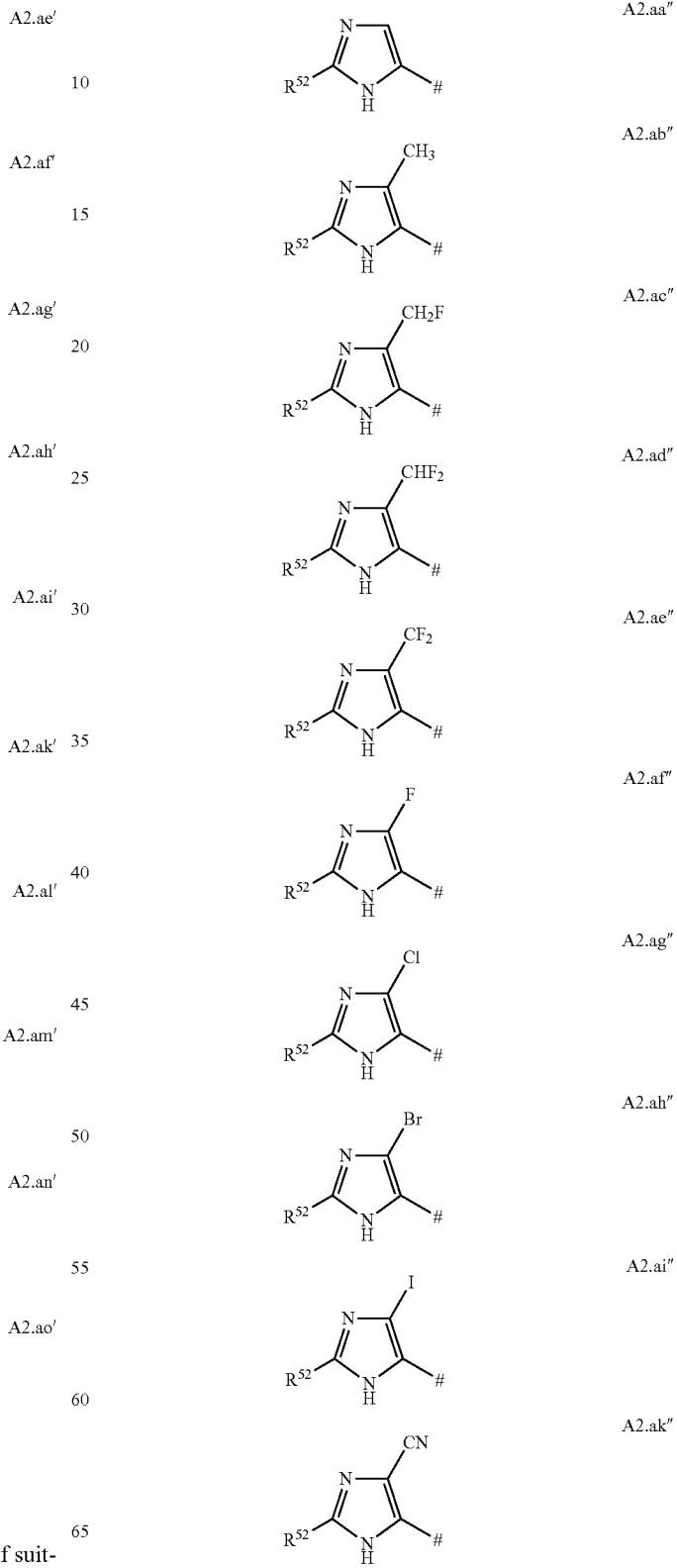

A2.aa"
A2.ab"
A2.ac"
A2.ad"
A2.ae"
A2.af"
A2.ag"
A2.ah"
A2.ai"
A2.ak"

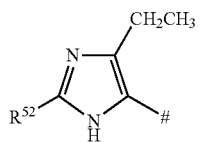
A2.al''
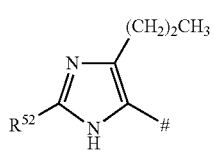
A2.am''
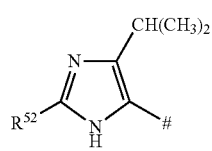
A2.an''
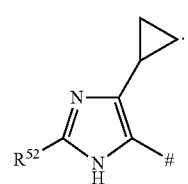
A2.ao''
Further examples of suitable radicals A2 are the radicals of formulae A2.ba, A2.bb, A2.bc, A2.bd, A2.be, A2.bf, A2.bg, A2.bh, A2.bi, A2.bk, A2.bl, A2.bm, A2.bn and A2.bo, wherein Z is N, $R^{62}$ is $CH_3$ and $R^{52}$ is as defined in one line of table A (radicals A2.ba1-A2.ba81 to A2.bo1-A2.bo81):
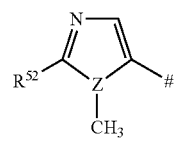
A2.ba
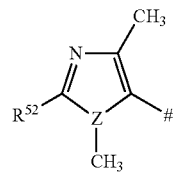
A2.bb
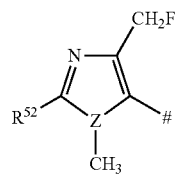
A2.bc
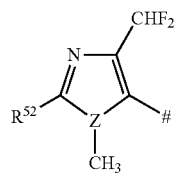
A2.bd
A2.be
A2.bf
A2.bg
A2.bh
A2.bi
A2.bk
A2.bl
A2.bm
A2.bn -continued

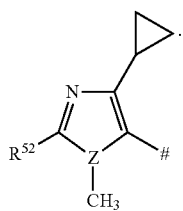
A2.bo

Further examples of suitable radicals A2 are the radicals of formulae A2.ca, A2.cb, A2.cc, A2.cd, A2.ce, A2.cf, A2.cg, A2.ch, A2.ci, A2.ck, A2.cl, A2.cm, A2.cn and A2.co, wherein Z is N, R$^{62}$ is CHF$_2$ and R$^{52}$ is as defined in one line of table A (radicals A2.ca1-A2.ca81 to A2.co1-A2.co81):

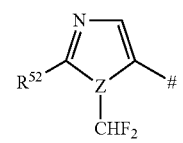
A2.ca

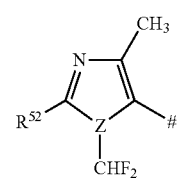
A2.cb

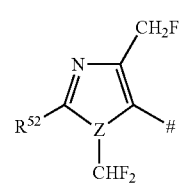
A2.cc

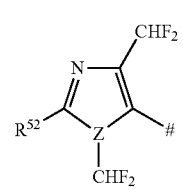
A2.cd

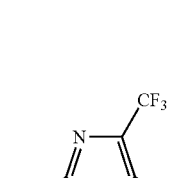
A2.ce

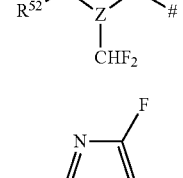
A2.cf

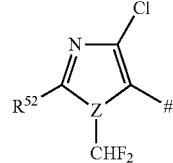
A2.cg

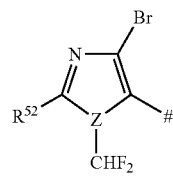
A2.ch

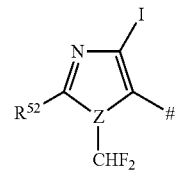
A2.ci

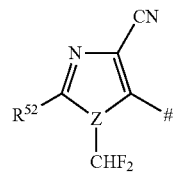
A2.ck

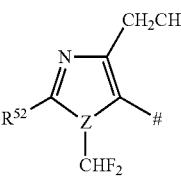
A2.cl

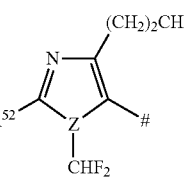
A2.cm

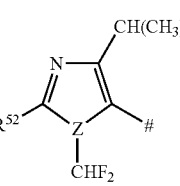
A2.cn

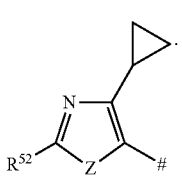
A2.co

Further examples of suitable radicals A2 are the radicals of formulae A2.da, A2.db, A2.dc, A2.dd, A2.de, A2.df, A2.dg, A2.dh, A2.di, A2.dk, A2.dl, A2.dm, A2.dn and A2.do, wherein Z is N, R$^{62}$ is CF$_3$ and R$^{52}$ is as defined in one line of table A (radicals A2.da1-A2.da81 to A2.do1-A2.do81):

| | | | |
|---|---|---|---|
| 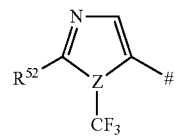 | A2.da | 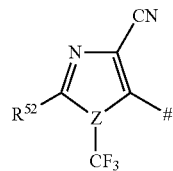 | A2.dk |
| 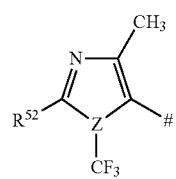 | A2.db | 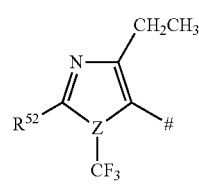 | A2.dl |
| 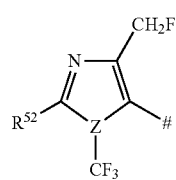 | A2.dc | 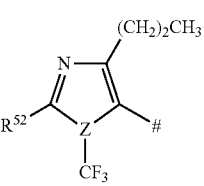 | A2.dm |
| 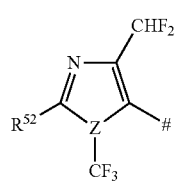 | A2.dd | 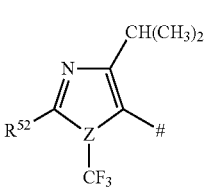 | A2.dn |
| 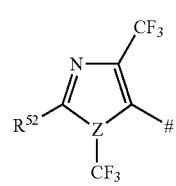 | A2.de | 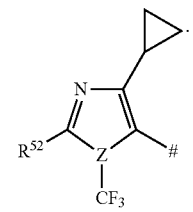 | A2.do |
| 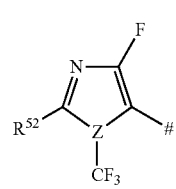 | A2.df | | |
| 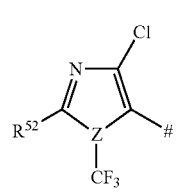 | A2.dg | | |
| 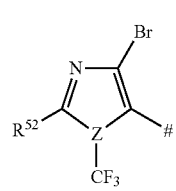 | A2.dh | 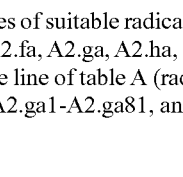 | A2.ea |
| 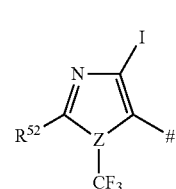 | A2.di | 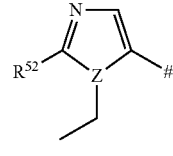 | A2.fa |
| | | 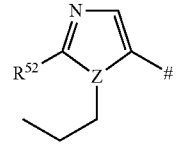 | A2.ga |
| | | 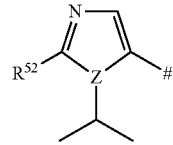 | |
Further examples of suitable radicals A2 are the radicals of formulae A2.ea, A2.fa, A2.ga, A2.ha, wherein Z is N and $R^{52}$ is as defined in one line of table A (radicals A2.ea1-A2.ea81, A2.fa1-A2.fa81, A2.ga1-A2.ga81, and A2.ha1-A2.ha81):

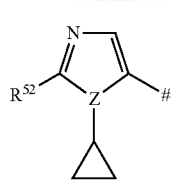

A2.ha

A further embodiment of the invention relates to pyridazine compounds of formulae I and II, to the salts and N-oxides thereof and to the methods and uses of such compounds, wherein A is a radical A3. Among the compounds of the formulae I and II, wherein A is a radical A3, preference is given to compounds of the formulae I or II, wherein $X^1$, $R^1$, $R^t$, $R^u$, $R^v$, and $R^w$ are as defined above and in particular have one of the preferred meanings.

Among the compounds of formulae I and II, wherein A is A3, preference is given to those compounds, wherein $R^{43}$ is selected from hydrogen, halogen, CN, $C_1$-$C_4$-alkyl and $C_2$-$C_{10}$-alkenyl, wherein the 2 last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{43}$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably $R^{43}$ is selected from hydrogen, halogen, CN, $C_1$-$C_4$-alkyl, $C_1$-$C_4$-haloalkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably $R^{43}$ is selected from hydrogen, halogen, CN, $C_1$-$C_4$-alkyl, $C_3$-$C_6$-cycloalkyl and $C_3$-$C_6$-halocycloalkyl. More preferably, $R^{43}$ is selected from hydrogen, halogen, $C_1$-$C_4$-alkyl, $C_1$-$C_4$-haloalkyl, $C_3$-$C_6$-cycloalkyl and $C_3$-$C_6$-halocycloalkyl. Most preferably $R^{43}$ is selected from hydrogen, $C_1$-$C_3$-alkyl, $C_1$-$C_3$-haloalkyl and $C_3$-$C_5$-cycloalkyl. Even more preferably $R^{43}$ is hydrogen or $C_1$-$C_3$-alkyl. In particular $R^{43}$ is hydrogen.

Among the compounds of formulae I and II, wherein A is A3, preference is further given to those compounds, wherein $R^{53}$ is selected from hydrogen, halogen, CN, $C_1$-$C_{10}$-alkyl and $C_2$-$C_{10}$-alkenyl, wherein the 2 last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{53}$ is further selected from $C_3$-$C_6$-cycloalkyl, $C_6$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably $R^{53}$ is selected from hydrogen, halogen, CN, $C_1$-$C_4$-alkyl, $C_1$-$C_4$-haloalkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. Preferably $R^{53}$ is selected from hydrogen, halogen, CN, $C_1$-$C_4$-alkyl, $C_1$-$C_4$-haloalkyl, $C_3$-$C_6$-cycloalkyl and $C_3$-$C_6$-halocycloalkyl. More preferably, $R^{53}$ is selected from hydrogen, halogen, $C_1$-$C_4$-alkyl, $C_1$-$C_4$-haloalkyl, $C_3$-$C_3$-cycloalkyl and $C_3$-$C_6$-halocycloalkyl. Most preferably $R^{53}$ is selected from hydrogen, $C_1$-$C_3$-alkyl, $C_1$-$C_3$-haloalkyl and $C_3$-$C_5$-cycloalkyl. Even more preferably $R^{53}$ is hydrogen or $C_1$-$C_3$-alkyl. In particular $R^{53}$ is hydrogen.

Among the compounds of formulae I and II, wherein A is A3, preference is further given to those compounds, wherein $R^{63}$ if present is selected from hydrogen, $C_1$-$C_{10}$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{63}$ if present is further selected from $C_3$-$C_6$-cycloalkyl, $C_6$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Preferably, $R^{63}$ is selected from hydrogen, $C_1$-$C_4$-alkyl, $C_1$-$C_4$-haloalkyl, $C_3$-$C_6$-cycloalkyl-$C_1$-$C_4$-alkyl, heterocyclyl-$C_1$-$C_4$-alkyl, $C_1$-$C_4$-alkoxy-$C_1$-$C_4$-alkyl and $C_1$-$C_4$-alkyl-CN. Preferably $R^{63}$ if present is selected from hydrogen, $C_1$-$C_4$-alkyl, $C_1$-$C_4$-haloalkyl, $C_3$-$C_6$-cycloalkyl, $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably $R^{63}$ if present is hydrogen, $C_1$-$C_4$-alkyl or $C_1$-$C_4$-haloalkyl. In particular $R^{63}$ if present is hydrogen or $C_1$-$C_3$-alkyl.

Examples of suitable radicals A3 are the radicals of formulae A3.aa, A3.ab, A3.ac, A3.ad, A3.ae, A3.af, A3.ag, A3.ah, A3.ai, A3.ak, A3.al, A3.am, A3.an and A3.ao, wherein Z is O and $R^{53}$ is a radical as defined in one line of table A (radicals A3.aa1-A3.aa81 to A3.ao1-A3.ao81):

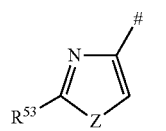

A3.aa

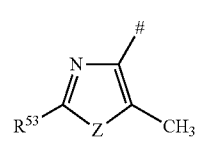

A3.ab

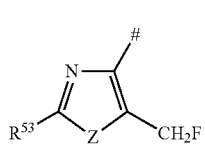

A3.ac

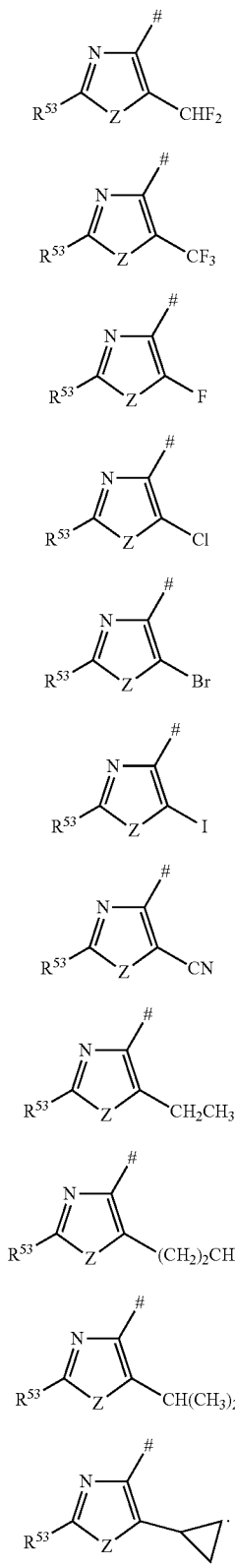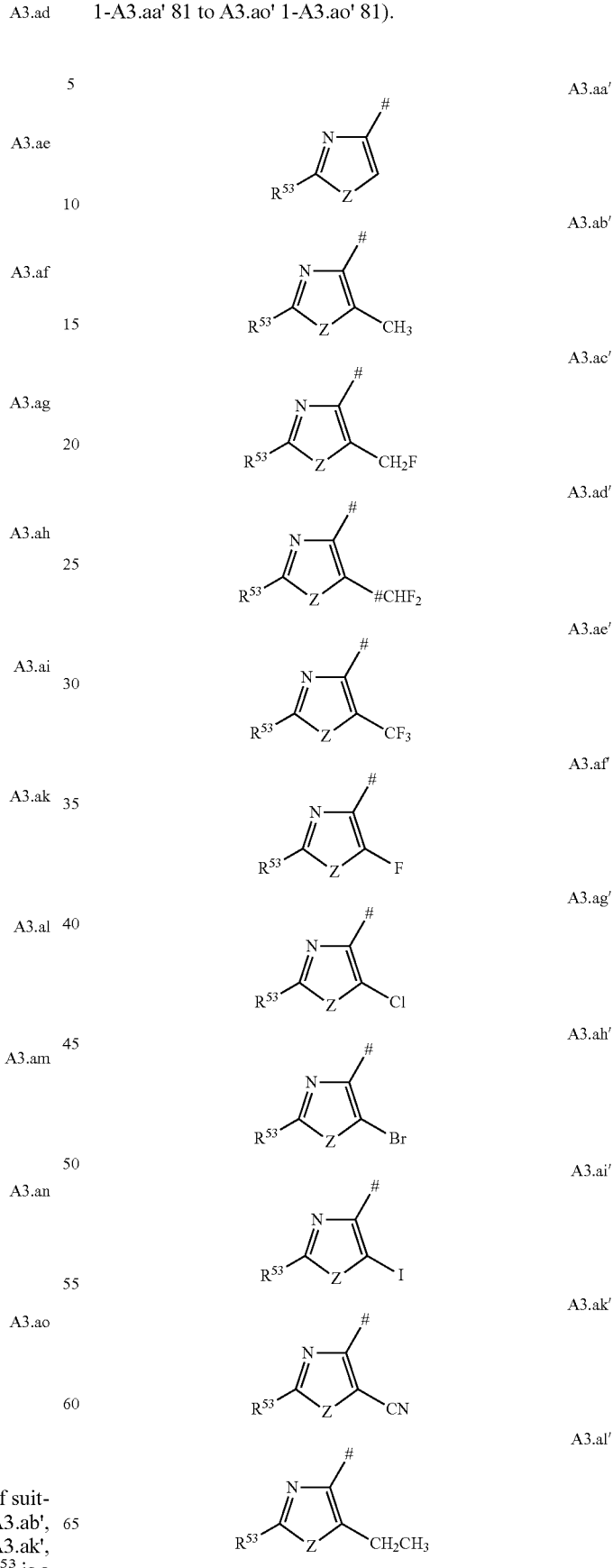
Analogue to the above listed structures, examples of suitable radicals A3 are the radicals of formulae A3.aa', A3.ab', A3.ac', A3.ad', A3.ae', A3.af', A3.ag', A3.ah', A3.ai', A3.ak', A3.al', A3.am', A3.an' and A3.ao', wherein Z is S and $R^{53}$ is a radical as defined in one line of table A (radicals A3.aa' 1-A3.aa' 81 to A3.ao' 1-A3.ao' 81).

-continued

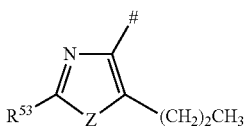 A3.am′

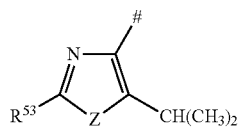 A3.an′

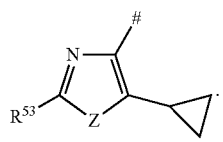 A3.ao′

Further examples of suitable radicals A3 are the radicals of formulae A3.aa″, A3.ab″, A3.ac″, A3.ad″, A3.ae″, A3.af″, A3.ag″, A3.ah″, A3.ak″, A3.al″, A3.am″, A3.an″ and A3.a″, wherein Z is N, R⁵³ is H and R⁶³ is a radical as defined in one line of table A (radicals A3.aa″ 1-A3.aa″ 81 to A3.ao″ 1-A3.ao″ 81):

A3.aa″

A3.ab″ (with CH₃)

A3.ac″ (with CH₂F)

A3.ad″ (with CHF₂)

A3.ae″ (with CF₃)

-continued

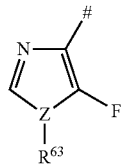 A3.af″

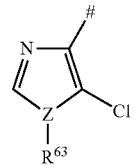 A3.ag″

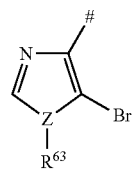 A3.ah″

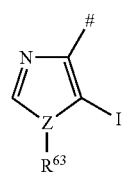 A3.ai″

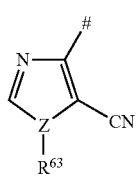 A3.ak″

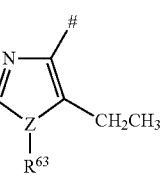 A3.al″

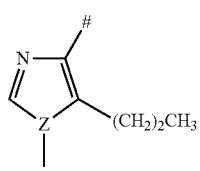 A3.am″

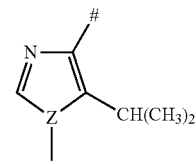 A3.an″

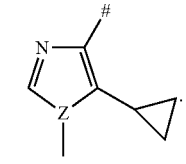 A3.ao″

Further examples of suitable radicals A3 are the radicals of formulae A3.ba, A3.bb, A3.bc, A3.bd, A3.be, A3.bf, A3.bg, A3.bh, A3.bi, A3.bk, A3.bl, A3.bm, A3.bn and A3.bo, wherein Z is N, $R^{53}$ is Cl and $R^{63}$ is a radical as defined in one row of table A (radicals A3.ba1-A3.ba81 to A3.bo1-A3.bo81):

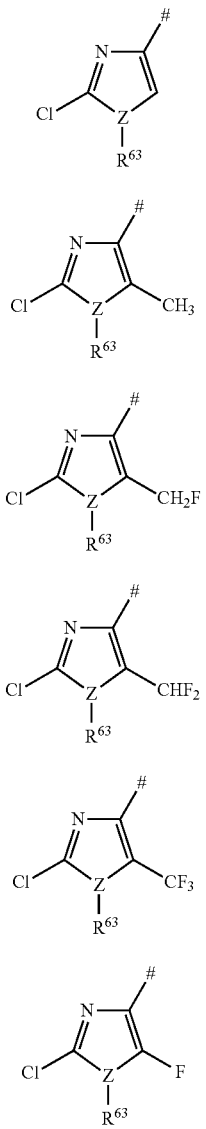

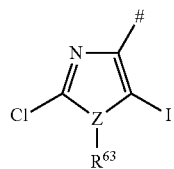

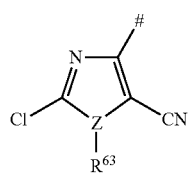

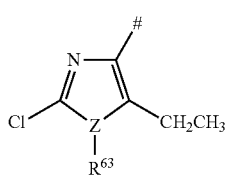

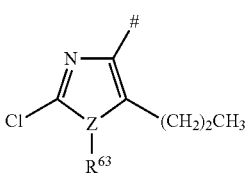

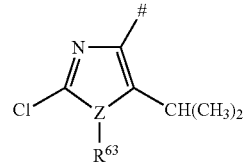

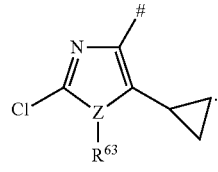

Further examples of suitable radicals A3 are the radicals of formulae A3.ca, A3.cb, A3.cc, A3.cd, A3.ce, A3.cf, A3.cg, A3.ch, A3.ci, A3.ck, A3.cl, A3.cm, A3.cn and A3.co, wherein $R^{53}$ is a radical as defined in one row of table A (radicals A3.ca1-A3.ca81 to A3.co1-A3.co81):

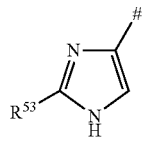

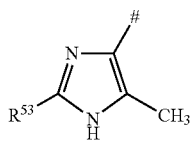

-continued
A3.cc
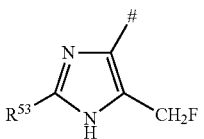
A3.cd
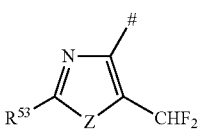
A3.ce
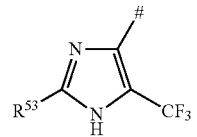
A3.cf
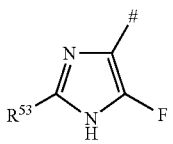
A3.cg
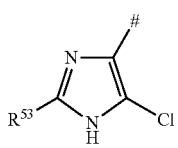
A3.ch
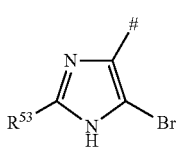
A3.ci
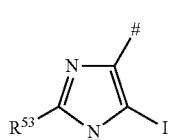
A3.ck
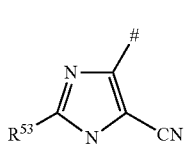
A3.cl
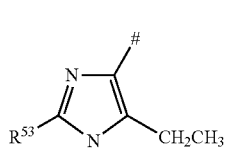
A3.cm
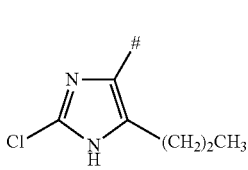
-continued
A3.cn
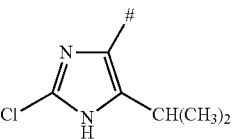
A3.co
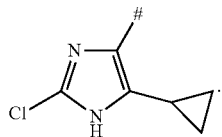
Further examples of suitable radicals A3 are the radicals of formulae A3.da, A3.db, A3.dc, A3.dd, A3.de, A3.df, A3.dg, A3.dh, A3.di, A3.dk, A3.dl, A3.dm, A3.dn and A3.do, wherein Z is N, $R^{63}$ is $CH_3$ and $R^{53}$ is a radical as defined in one row of table A (radicals A3.da1-A3.da81 to A3.do1-A3.do81):
A3.da
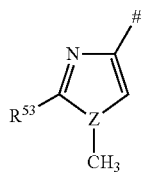
A3.db
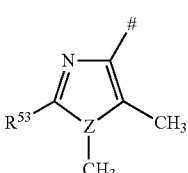
A3.dc
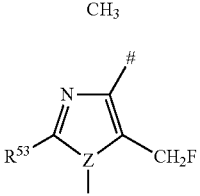
A3.dd
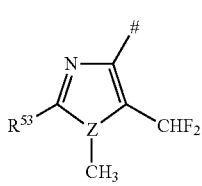
A3.de
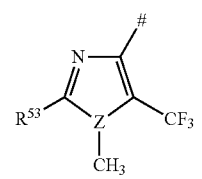
A3.df
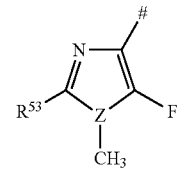

Further examples of suitable radicals A3 are the radicals of formulae A3.ea, A3.eb, A3.ec, A3.ed, A3.ee, A3.ef, A3.eg, A3.eh, A3.ei, A3.ek, A3.el, A3.em, A3.en and A3.eo, wherein Z is N, $R^{63}$ is $CHF_2$ and $R^{53}$ is a radical as defined in one row of table A (radicals A3.ea1-A3.ea81 to A3.eo1-A3.eo81):

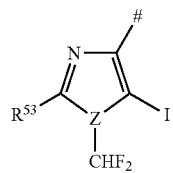 A3.ei
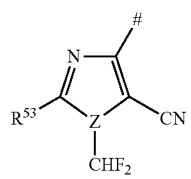 A3.ek
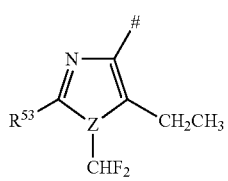 A3.el
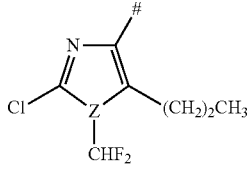 A3.em
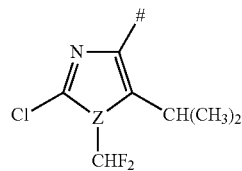 A3.en
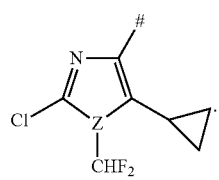 A3.eo
Further examples of suitable radicals A3 are the radicals of formulae A3.fa, A3.fb, A3.fc, A3.fd, A3.fe, A3.ff, A3.fg, A3.fh, A3.fi, A3.fk, A3.fl, A3.fm, A3.fn and A3.fo, wherein Z is N, $R^{63}$ is $CF_3$ and $R^{53}$ is a radical as defined in one row of table A (radicals A3.fa1-A3.fa81 to A3.fo1-A3.fo81):
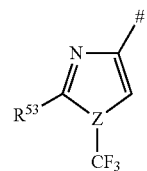 A3.fa
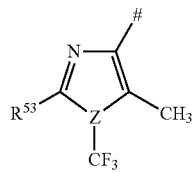 A3.fb
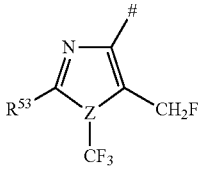 A3.fc
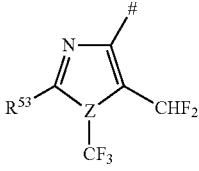 A3.fd
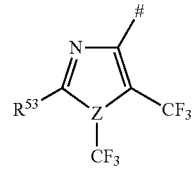 A3.fe
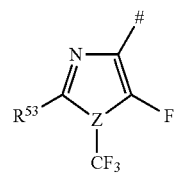 A3.ff
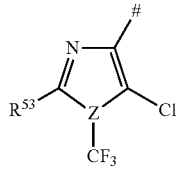 A3.fg
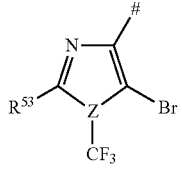 A3.fh
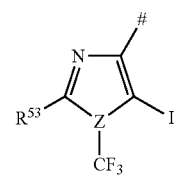 A3.fi -continued A3.fk
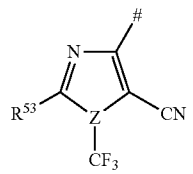

A3.fl
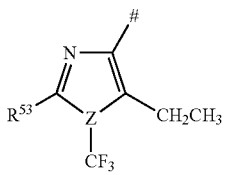

A3.fm
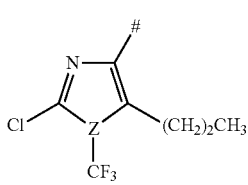

A3.fn
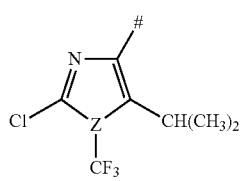

A3.fo
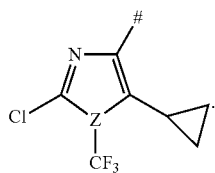

Further examples of suitable radicals A3 are the radicals of formulae A3.&1, A3.&2, A3.3 wherein Z is N, $R^{63}$ is $CH_2CF_3$ and $R^{53}$ is respectively $CH_3$, $CF_3$ and $CHF_2$:

A3.&1

A3.&2
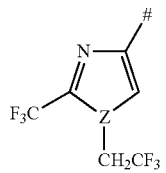

A3.&3
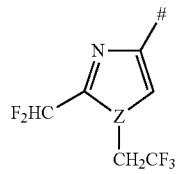

A very preferred embodiment of the invention relates to compounds of the formula I and to the salts and N-oxides thereof, wherein $X^1$ is O. These compounds are hereinafter also referred to as compounds I'.

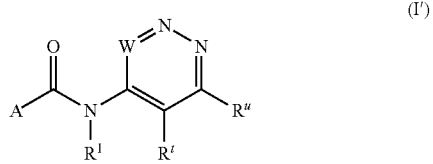
(I')

In formula I', the variables A, $R^1$, $R^t$, $R^u$, V and W are as defined herein.

Among the compounds of the formula I', preference is given to those compounds, wherein at least one of the radicals $R^1$, $R^t$, $R^u$, V and W, preferably at least two of the radicals $R^1$, $R^t$, $R^u$, V and W, and more preferably all of the radicals $R^1$, $R^t$, $R^u$, V and W have one of the preferred meanings.

Among the compounds of the formula I', preference is further given to those compounds, wherein A is a radical A1, e.g. a radical, selected from the oxazole radicals A1.a1 to A1.z81.

Among the compounds of the formula I', preference is further given to those compounds, wherein A is a radical A1, e.g. a radical, selected from the thiazole radicals A1.a' 1 to A1.z' 81

Among the compounds of the formula I', preference is further given to those compounds, wherein A is a radical A1, e.g. a radical, selected from the imidazole radicals A1.a" 1 to A1.z" 81

A particularly preferred embodiment of the invention relates to compounds of formula I'.A and to the salts and N-oxides thereof, wherein

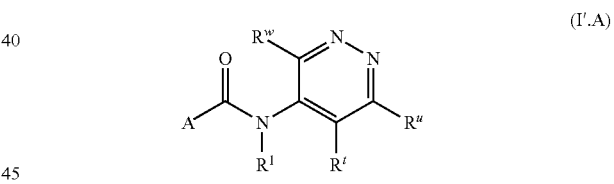
(I'.A)

A is a radical A1, as defined herein, in particular a radical A1, wherein $R^{41}$, $R^{51}$ have the preferred meanings, in particular an oxazole radical of the formulae A1.a to A1.z, e.g. a radical selected from the oxazole radicals A1.a1 to A1.z81;

$R^1$ is hydrogen, $C_1$-$C_4$-alkyl or $C_1$-$C_4$-alkoxy-$C_1$-$C_2$-alkyl, most preferably hydrogen, methyl or ethyl;

R1 is further most preferably propyl, iso-propyl, butyl, iso-butyl, tert-butyl, $CH_2C(CH_3)_3$, $CH_2CH=CH$, $CH_2CH=CCl_2$, $CH_2CH=CBr_2$, $CH_2CH_2F$, $CH_2CH_2Cl$, $CH_2CH_2Br$, $CH_2CHF_2$, $CH_2CHCl_2$, $CH_2CHBr_2$, $CH_2CF_3$, $CH_2CN$, $CH_2OCH_3$, $CH_2OCH_2CH_3$, $CH_2CH_2CN$, $CH_2CHCN_2$, $CH_2CH_2OCH_3$, $CH_2CH_2OCH_2CH_3$, ethyl-cyclopropane, ethyl-cyclobutane, 2-methyl-oxetane, 3-ethyl-oxetane, 3-methyl-thietane, 3-methyl-thietane 1,1-dioxide, ethyl-cyclopentane, 2-ethyl-tetrahydro-furan, 3-ethyl-tetrahydro-furan, methyl-cyclopropane, methyl-cyclobutane, 2-methyl-oxetane, 3-methyl-oxetane, 3-methyl-thietane, 3-thietane 1,1-dioxide, cyclopentane, 2-methyl-tetrahydro-furan, tetrahydro-furan, toluene, 2-methyl-furan, 3-methyl-furan, 2-ethyl-thiophene, 3-methyl-thiophene, 5-ethyl-isothiazole, 4-ethyl-isothiazole, 3-methyl-isothiazole, 3-methyl-isoxazole, 5-methyl-oxazole, 2-ethyl-oxazole, 5-ethyl-thiazole, 2-ethyl-thiazole, 4-ethyl-thiazole, 5-methyl-1H-pyrazole, 4-ethyl-1H-pyrazole, 3-methyl-1H-pyrazole; 5-ethyl-1-methyl-1H-pyrazole, 4-ethyl-1-methyl-1H-pyrazole, 3-ethyl-1-methyl-1H-pyrazole, 5-methyl-1H-imidazole, 4-ethyl-1H-imidazole, 2-methyl-1H-imidazole, 5-ethyl-1-methyl-1H-imidazole, 2-ethyl-1-methyl-1H-imidazole, 1,4-dimethyl-1H-imidazole, 2-methyl-4,5-dihydro-oxazole, 2-ethyl-4,5-dihydro-thiazole, 2-ethyl-4,5-dihydro-1H-imidazole, 2-ethyl-1-methyl-4,5-dihydro-1H-imidazole;

$R^r$, $R^u$, and $R^w$ are independently from each other selected from hydrogen, methyl, difluoromethyl, trifluoromethyl, methoxy, difluoromethoxy and trifluoromethoxy; and wherein preferably at least one, more preferably 2 or 3, of the radicals $R^r$, $R^u$, and $R^w$ are hydrogen.

Examples of compounds of this particularly preferred embodiment are the compounds given in the following tables 1 to 50.

Table 1: Compounds of the formula I'.A and the salts and N-oxides thereof, wherein $R^1$, $R^r$, $R^u$ and $R^w$ are hydrogen and wherein A is selected from the radicals A1.a1 to A1.a81.

Table 2: Compounds of the formula I'.A and the salts and N-oxides thereof, wherein $R^1$ is methyl, $R^r$, $R^u$ and $R^w$ are hydrogen and wherein A is selected from the radicals A1.a1 to A1.a81.

Table 3: Compounds of the formula I'.A and the salts and N-oxides thereof, wherein $R^1$, $R^r$, $R^u$ and $R^w$ are hydrogen and wherein A is selected from the radicals A1.b1 to A1.b81.

Table 4: Compounds of the formula I'.A and the salts and N-oxides thereof, wherein $R^1$ is methyl, $R^r$, $R^u$ and $R^w$ are hydrogen and wherein A is selected from the radicals A1.b1 to A1.b81.

Table 5: Compounds of the formula I'.A and the salts and N-oxides thereof, wherein $R^1$, $R^r$, $R^u$ and $R^w$ are hydrogen and wherein A is selected from the radicals A1.c1 to A1.c81.

Table 6: Compounds of the formula I'.A and the salts and N-oxides thereof, wherein $R^1$ is methyl, $R^r$, $R^u$ and $R^w$ are hydrogen and wherein A is selected from the radicals A1.c1 to A1.c81.

Table 7: Compounds of the formula I'.A and the salts and N-oxides thereof, wherein $R^1$, $R^r$, $R^u$ and $R^w$ are hydrogen and wherein A is selected from the radicals A1.d1 to A1.d81.

Table 8: Compounds of the formula I'.A and the salts and N-oxides thereof, wherein $R^1$ is methyl, $R^r$, $R^u$ and $R^w$ are hydrogen and wherein A is selected from the radicals A1.d1 to A1.d81.

Table 9: Compounds of the formula I'.A and the salts and N-oxides thereof, wherein $R^1$, $R^r$, $R^u$ and $R^w$ are hydrogen and wherein A is selected from the radicals A1.e1 to A1.e81.

Table 10: Compounds of the formula I'.A and the salts and N-oxides thereof, wherein $R^1$ is methyl, $R^r$, $R^u$ and $R^w$ are hydrogen and wherein A is selected from the radicals A1.e1 to A1.e81.

Table 11: Compounds of the formula I'.A and the salts and N-oxides thereof, wherein $R^1$, $R^r$, $R^u$ and $R^w$ are hydrogen and wherein A is selected from the radicals A1.f1 to A1.f81.

Table 12: Compounds of the formula I'.A and the salts and N-oxides thereof, wherein $R^1$ is methyl, $R^r$, $R^u$ and $R^w$ are hydrogen and wherein A is selected from the radicals A1.f1 to A1.f81.

Table 13: Compounds of the formula I'.A and the salts and N-oxides thereof, wherein $R^1$, $R^r$, $R^u$ and $R^w$ are hydrogen and wherein A is selected from the radicals A1.g1 to A1.g81.

Table 14: Compounds of the formula I'.A and the salts and N-oxides thereof, wherein $R^1$ is methyl, $R^r$, $R^u$ and $R^w$ are hydrogen and wherein A is selected from the radicals A1.g1 to A1.g81.

Table 15: Compounds of the formula I'.A and the salts and N-oxides thereof, wherein $R^1$, $R^r$, $R^u$ and $R^w$ are hydrogen and wherein A is selected from the radicals A1.h1 to A1.h81.

Table 16: Compounds of the formula I'.A and the salts and N-oxides thereof, wherein $R^1$ is methyl, $R^r$, $R^u$ and $R^w$ are hydrogen and wherein A is selected from the radicals A1.h1 to A1.h81.

Table 17: Compounds of the formula I'.A and the salts and N-oxides thereof, wherein $R^1$, $R^r$, $R^u$ and $R^w$ are hydrogen and wherein A is selected from the radicals A1.i1 to A1.i81.

Table 18: Compounds of the formula I'.A and the salts and N-oxides thereof, wherein $R^1$ is methyl, $R^r$, $R^u$ and $R^w$ are hydrogen and wherein A is selected from the radicals A1.i1 to A1.i81.

Table 19: Compounds of the formula I'.A and the salts and N-oxides thereof, wherein $R^1$, $R^r$, $R^u$ and $R^w$ are hydrogen and wherein A is selected from the radicals A1.k1 to A1.k81.

Table 20: Compounds of the formula I'.A and the salts and N-oxides thereof, wherein $R^1$ is methyl, $R^r$, $R^u$ and $R^w$ are hydrogen and wherein A is selected from the radicals A1.k1 to A1.k81.

Table 21: Compounds of the formula I'.A and the salts and N-oxides thereof, wherein $R^1$, $R^r$, $R^u$ and $R^w$ are hydrogen and wherein A is selected from the radicals A1.l1 to A1.l81.

Table 22: Compounds of the formula I'.A and the salts and N-oxides thereof, wherein $R^1$ is methyl, $R^r$, $R^u$ and $R^w$ are hydrogen and wherein A is selected from the radicals A1.l1 to A1.l81.

Table 23: Compounds of the formula I'.A and the salts and N-oxides thereof, wherein $R^1$, $R^r$, $R^u$ and $R^w$ are hydrogen and wherein A is selected from the radicals A1.m1 to A1.m81.

Table 24: Compounds of the formula I'.A and the salts and N-oxides thereof, wherein $R^1$ is methyl, $R^r$, $R^u$ and $R^w$ are hydrogen and wherein A is selected from the radicals A1.m1 to A1.m81.

Table 25: Compounds of the formula I'.A and the salts and N-oxides thereof, wherein $R^1$, $R^r$, $R^u$ and $R^w$ are hydrogen and wherein A is selected from the radicals A1.n1 to A1.n81.

Table 26: Compounds of the formula I'.A and the salts and N-oxides thereof, wherein $R^1$ is methyl, $R^r$, $R^u$ and $R^w$ are hydrogen and wherein A is selected from the radicals A1.n1 to A1.n81.

Table 27: Compounds of the formula I'.A and the salts and N-oxides thereof, wherein $R^1$, $R^r$, $R^u$ and $R^w$ are hydrogen and wherein A is selected from the radicals A1.o1 to A1.o81.

Table 28: Compounds of the formula I'.A and the salts and N-oxides thereof, wherein $R^1$ is methyl, $R^r$, $R^u$ and $R^w$ are hydrogen and wherein A is selected from the radicals A1.o1 to A1.o81.

Table 29: Compounds of the formula I'.A and the salts and N-oxides thereof, wherein $R^1$, $R^r$, $R^u$ and $R^w$ are hydrogen and wherein A is selected from the radicals A1.p1 to A1.p81.

Table 30: Compounds of the formula I'.A and the salts and N-oxides thereof, wherein $R^1$ is methyl, $R^t$, $R^u$ and $R^w$ are hydrogen and wherein A is selected from the radicals A1.p1 to A1.p81.

Table 31: Compounds of the formula I'.A and the salts and N-oxides thereof, wherein $R^1$, $R^t$, $R^u$ and $R^w$ are hydrogen and wherein A is selected from the radicals A1.q1 to A1.q81.

Table 32: Compounds of the formula I'.A and the salts and N-oxides thereof, wherein $R^1$ is methyl, $R^t$, $R^u$ and $R^w$ are hydrogen and wherein A is selected from the radicals A1.q1 to A1.q81.

Table 33: Compounds of the formula I'.A and the salts and N-oxides thereof, wherein $R^1$, $R^t$, $R^u$ and $R^w$ are hydrogen and wherein A is selected from the radicals A1.r1 to A1.r81.

Table 34: Compounds of the formula I'.A and the salts and N-oxides thereof, wherein $R^1$ is methyl, $R^t$, $R^u$ and $R^w$ are hydrogen and wherein A is selected from the radicals A1.r1 to A1.r81.

Table 35: Compounds of the formula I'.A and the salts and N-oxides thereof, wherein $R^1$, $R^t$, $R^u$ and $R^w$ are hydrogen and wherein A is selected from the radicals A1.s1 to A1.s81.

Table 36: Compounds of the formula I'.A and the salts and N-oxides thereof, wherein $R^1$ is methyl, $R^t$, $R^u$ and $R^w$ are hydrogen and wherein A is selected from the radicals A1.s1 to A1.s81.

Table 37: Compounds of the formula I'.A and the salts and N-oxides thereof, wherein $R^1$, $R^t$, $R^u$ and $R^w$ are hydrogen and wherein A is selected from the radicals A1.t1 to A1.t81.

Table 38: Compounds of the formula I'.A and the salts and N-oxides thereof, wherein $R^1$ is methyl, $R^t$, $R^u$ and $R^w$ are hydrogen and wherein A is selected from the radicals A1.t1 to A1.t81.

Table 39: Compounds of the formula I'.A and the salts and N-oxides thereof, wherein $R^1$, $R^t$, $R^u$ and $R^w$ are hydrogen and wherein A is selected from the radicals A1.u1 to A1.u81.

Table 40: Compounds of the formula I'.A and the salts and N-oxides thereof, wherein $R^1$ is methyl, $R^t$, $R^u$ and $R^w$ are hydrogen and wherein A is selected from the radicals A1.u1 to A1.u81.

Table 41: Compounds of the formula I'.A and the salts and N-oxides thereof, wherein $R^1$, $R^t$, $R^u$ and $R^w$ are hydrogen and wherein A is selected from the radicals A1.v1 to A1.v81.

Table 42: Compounds of the formula I'.A and the salts and N-oxides thereof, wherein $R^1$ is methyl, $R^t$, $R^u$ and $R^w$ are hydrogen and wherein A is selected from the radicals A1.v1 to A1.v81.

Table 43: Compounds of the formula I'.A and the salts and N-oxides thereof, wherein $R^1$, $R^t$, $R^u$ and $R^w$ are hydrogen and wherein A is selected from the radicals A1.w1 to A1.w81.

Table 44: Compounds of the formula I'.A and the salts and N-oxides thereof, wherein $R^1$ is methyl, $R^t$, $R^u$ and $R^w$ are hydrogen and wherein A is selected from the radicals A1.w1 to A1.w81.

Table 45: Compounds of the formula I'.A and the salts and N-oxides thereof, wherein $R^1$, $R^t$, $R^u$ and $R^w$ are hydrogen and wherein A is selected from the radicals A1.x1 to A1.x81.

Table 46: Compounds of the formula I'.A and the salts and N-oxides thereof, wherein $R^1$ is methyl, $R^t$, $R^u$ and $R^w$ are hydrogen and wherein A is selected from the radicals A1.x1 to A1.x81.

Table 47: Compounds of the formula I'.A and the salts and N-oxides thereof, wherein $R^1$, $R^t$, $R^u$ and $R^w$ are hydrogen and wherein A is selected from the radicals A1.y1 to A1.y81.

Table 48: Compounds of the formula I'.A and the salts and N-oxides thereof, wherein $R^1$ is methyl, $R^t$, $R^u$ and $R^w$ are hydrogen and wherein A is selected from the radicals A1.y1 to A1.y81.

Table 49: Compounds of the formula I'.A and the salts and N-oxides thereof, wherein $R^1$, $R^t$, $R^u$ and $R^w$ are hydrogen and wherein A is selected from the radicals A1.z1 to A1.z81.

Table 50: Compounds of the formula I'.A and the salts and N-oxides thereof, wherein $R^1$ is methyl, $R^t$, $R^u$ and $R^w$ are hydrogen and wherein A is selected from the radicals A1.z1 to A1.z81.

Further examples of compounds of this particularly preferred embodiment are the compounds in analogy to the compounds listed in table 1 to 50 wherein $R^1$ is a radical represented by each individual line (85 to 160) of the following table B:

TABLE B

| Line | Radical $R^1$ |
|---|---|
| 85 | $CH_2CH_3$ |
| 86 | propyl |
| 87 | iso-propyl |
| 88 | butyl |
| 89 | iso-butyl |
| 90 | tert-butyl |
| 91 | $CH_2C(CH_3)_3$ |
| 92 | $CH_2CH=CH$ |
| 93 | $CH_2CH=CCl_2$ |
| 94 | $CH_2CH=CBr_2$ |
| 95 | $CH_2CH_2F$ |
| 96 | $CH_2CH_2Cl$ |
| 97 | $CH_2CH_2Br$ |
| 98 | $CH_2CHF_2$ |
| 99 | $CH_2CHCl_2$ |
| 100 | $CH_2CHBr_2$ |
| 101 | $CH_2CF_3$ |
| 102 | $CH_2CN$ |
| 103 | $CH_2OCH_3$ |
| 104 | $CH_2OCH_2CH_3$ |
| 105 | $CH_2CH_2CN$ |
| 106 | $CH(Me)CH_2CN$ |
| 107 | 2-methoxyethyl |
| 108 | 2-ethoxyethyl |
| 109 | cyclopropylmethyl |
| 110 | cyclobutylmethyl |
| 111 | cyclopentylmethyl |
| 112 | oxetan-2-ylmethyl |
| 113 | oxetan-3-ylmethyl |
| 114 | oxolan-2-ylmethyl |
| 115 | oxolan-3-ylmethyl |
| 116 | thiethan-3-ylmethyl |
| 117 | 1,1-dioxathiethan-3-ylmethyl |
| 118 | cyclopropyl |
| 119 | cyclobutyl |
| 120 | cyclopentyl |
| 121 | oxetan-2-yl |
| 122 | oxetan-3-yl |
| 123 | oxolan-2-yl |
| 124 | oxolan-3-yl |
| 125 | thiethan-3-yl |
| 126 | 1,1-dioxathiethan-3-yl |
| 127 | benzyl |
| 128 | 2-furylmethyl |
| 129 | 3-furylmethyl |
| 130 | 2-thienylmethyl |
| 131 | 3-thienylmethyl |
| 132 | isothiazol-3-ylmethyl |
| 133 | isothiazol-4-ylmethyl |
| 134 | isothiazol-5-ylmethyl |

TABLE B-continued

| Line | Radical R¹ |
|---|---|
| 135 | isoxazol-3-ylmethyl |
| 136 | oxazol-2-ylmethyl |
| 137 | oxazol-5-ylmethyl |
| 138 | oxazol-4-ylmethyl |
| 139 | thiazol-2-ylmethyl |
| 140 | thiazol-4-ylmethyl |
| 141 | thiazol-5-ylmethyl |
| 142 | 1H-pyrazol-3-ylmethyl |
| 143 | 1H-pyrazol-4-ylmethyl |
| 144 | 2H-pyrazol-3-ylmethyl |
| 145 | 1-methyl-1H-pyrazol-3-ylmethyl |
| 146 | 1-methyl-1H-pyrazol-4-ylmethyl |
| 147 | 2-methyl-2H-pyrazol-3-ylmethyl |
| 148 | 1H-imidazol-2-ylmethyl |
| 149 | 1H-imidazol-4-ylmethyl |
| 150 | 1H-imidazol-5-ylmethyl |
| 151 | 1-methyl-1H-imidazol-2-ylmethyl |
| 152 | 1-methyl-1H-imidazol-4-ylmethyl |
| 153 | 1-methyl-1H-imidazol-5-ylmethyl |
| 154 | oxazolin-2-ylmethyl |
| 155 | thiazolin-2-ylmethyl |
| 156 | 1H-imidazolin-2-ylmethyl |
| 157 | 1-methyl-1H-imidazolin-2-ylmethyl |
| 158 | 1-phenylpyrazol-4-ylmethyl |
| 159 | 5-methylfuran-2-ylmethyl |
| 160 | 5,5-dimethyltetrahydrofuran-2-ylmethyl |

Another particular preferred embodiment relates to compounds of the formula I'.A and to the salts and N-oxides thereof, wherein A is a radical A1, as defined herein, in particular a radical A1, wherein $R^{41}$, $R^{51}$ have the preferred meanings, in particular a thiazole radical of the formulae A1.a' to A1.z', e.g. a radical selected from the thiazole radicals A1.a' 1 to A1.z' 81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^t$, $R^u$, and $R^w$ are independently from each other selected from hydrogen, methyl, difluoromethyl, trifluoromethyl, methoxy, difluoromethoxy and trifluoromethoxy; and wherein preferably at least one, more preferably 2 or 3, of the radicals $R^t$, $R^u$, and $R^w$ are hydrogen Examples of compounds of this particularly preferred embodiment are the compounds given in the following tables 51 to 100

Table 51: Compounds of the formula I'.A and the salts and N-oxides thereof, wherein $R^1$, $R^t$, $R^u$ and $R^w$ are hydrogen and wherein A is selected from the radicals A1.a' 1 to A1.a' 81.

Table 52: Compounds of the formula I'.A and the salts and N-oxides thereof, wherein $R^1$ is methyl, $R^t$, $R^u$ and $R^w$ are hydrogen and wherein A is selected from the radicals A1.a' 1 to A1.a' 81.

Table 53: Compounds of the formula I'.A and the salts and N-oxides thereof, wherein $R^1$, $R^t$, $R^u$ and $R^w$ are hydrogen and wherein A is selected from the radicals A1.b' 1 to A1.b' 81.

Table 54: Compounds of the formula I'.A and the salts and N-oxides thereof, wherein $R^1$ is methyl, $R^t$, $R^u$ and $R^w$ are hydrogen and wherein A is selected from the radicals A1.b' 1 to A1.b' 81.

Table 55: Compounds of the formula I'.A and the salts and N-oxides thereof, wherein $R^1$, $R^t$, $R^u$ and $R^w$ are hydrogen and wherein A is selected from the radicals A1.c' 1 to A1.c' 81.

Table 56: Compounds of the formula I'.A and the salts and N-oxides thereof, wherein $R^1$ is methyl, $R^t$, $R^u$ and $R^w$ are hydrogen and wherein A is selected from the radicals A1.c' 1 to A1.c' 81.

Table 57: Compounds of the formula I'.A and the salts and N-oxides thereof, wherein $R^1$, $R^t$, $R^u$ and $R^w$ are hydrogen and wherein A is selected from the radicals A1.d' 1 to A1.d' 81.

Table 58: Compounds of the formula I'.A and the salts and N-oxides thereof, wherein $R^1$ is methyl, $R^t$, $R^u$ and $R^w$ are hydrogen and wherein A is selected from the radicals A1.d' 1 to A1.d' 81.

Table 59: Compounds of the formula I'.A and the salts and N-oxides thereof, wherein $R^1$, $R^t$, $R^u$ and $R^w$ are hydrogen and wherein A is selected from the radicals A1.e' 1 to A1.e' 81.

Table 60: Compounds of the formula I'.A and the salts and N-oxides thereof, wherein $R^1$ is methyl, $R^t$, $R^u$ and $R^w$ are hydrogen and wherein A is selected from the radicals A1.e' 1 to A1.e' 81.

Table 61: Compounds of the formula I'.A and the salts and N-oxides thereof, wherein $R^1$, $R^t$, $R^u$ and $R^w$ are hydrogen and wherein A is selected from the radicals A1.f' 1 to A1.f' 81.

Table 62: Compounds of the formula I'.A and the salts and N-oxides thereof, wherein $R^1$ is methyl, $R^t$, $R^u$ and $R^w$ are hydrogen and wherein A is selected from the radicals A1.f' 1 to A1.f' 81.

Table 63: Compounds of the formula I'.A and the salts and N-oxides thereof, wherein $R^1$, $R^t$, $R^u$ and $R^w$ are hydrogen and wherein A is selected from the radicals A1.g' 1 to A1.g' 81.

Table 64: Compounds of the formula I'.A and the salts and N-oxides thereof, wherein $R^1$ is methyl, $R^t$, $R^u$ and $R^w$ are hydrogen and wherein A is selected from the radicals A1.g' 1 to A1.g' 81.

Table 65: Compounds of the formula I'.A and the salts and N-oxides thereof, wherein $R^1$, $R^t$, $R^u$ and $R^w$ are hydrogen and wherein A is selected from the radicals A1.h' 1 to A1.h' 81.

Table 66: Compounds of the formula I'.A and the salts and N-oxides thereof, wherein $R^1$ is methyl, $R^t$, $R^o$ and $R^w$ are hydrogen and wherein A is selected from the radicals A1.h' 1 to A1.h' 81.

Table 67: Compounds of the formula I'.A and the salts and N-oxides thereof, wherein $R^1$, $R^t$, $R^u$ and $R^w$ are hydrogen and wherein A is selected from the radicals A1.i' 1 to A1.i' 81.

Table 68: Compounds of the formula I'.A and the salts and N-oxides thereof, wherein $R^1$ is methyl, $R^t$, $R^u$ and $R^w$ are hydrogen and wherein A is selected from the radicals A1.i' 1 to A1.i' 81.

Table 69: Compounds of the formula I'.A and the salts and N-oxides thereof, wherein $R^1$, $R^t$, $R^u$ and $R^w$ are hydrogen and wherein A is selected from the radicals A1.k' 1 to A1.k' 81.

Table 70: Compounds of the formula I'.A and the salts and N-oxides thereof, wherein $R^1$ is methyl, $R^t$, $R^u$ and $R^w$ are hydrogen and wherein A is selected from the radicals A1.k' 1 to A1.k' 81.

Table 71: Compounds of the formula I'.A and the salts and N-oxides thereof, wherein $R^1$, $R^r$, $R^u$ and $R^w$ are hydrogen and wherein A is selected from the radicals A1.l' 1 to A1.l' 81.

Table 72: Compounds of the formula I'.A and the salts and N-oxides thereof, wherein $R^1$ is methyl, $R^r$, $R^u$ and $R^w$ are hydrogen and wherein A is selected from the radicals A1.l' 1 to A1.l' 81.

Table 73: Compounds of the formula I'.A and the salts and N-oxides thereof, wherein $R^1$, $R^r$, $R^u$ and $R^w$ are hydrogen and wherein A is selected from the radicals A1.m' 1 to A1.m' 81.

Table 74: Compounds of the formula I'.A and the salts and N-oxides thereof, wherein $R^1$ is methyl, $R^r$, $R^u$ and $R^w$ are hydrogen and wherein A is selected from the radicals A1.m' 1 to A1.m' 81.

Table 75: Compounds of the formula I'.A and the salts and N-oxides thereof, wherein $R^1$, $R^r$, $R^u$ and $R^w$ are hydrogen and wherein A is selected from the radicals A1.n' 1 to A1.n' 81.

Table 76: Compounds of the formula I'.A and the salts and N-oxides thereof, wherein $R^1$ is methyl, $R^r$, $R^u$ and $R^w$ are hydrogen and wherein A is selected from the radicals A1.n' 1 to A1.n' 81.

Table 77: Compounds of the formula I'.A and the salts and N-oxides thereof, wherein $R^1$, $R^r$, $R^u$ and $R^w$ are hydrogen and wherein A is selected from the radicals A1.o' 1 to A1.o' 81.

Table 78: Compounds of the formula I'.A and the salts and N-oxides thereof, wherein $R^1$ is methyl, $R^r$, $R^u$ and $R^w$ are hydrogen and wherein A is selected from the radicals A1.o' 1 to A1.o' 81.

Table 79: Compounds of the formula I'.A and the salts and N-oxides thereof, wherein $R^1$, $R^r$, $R^u$ and $R^w$ are hydrogen and wherein A is selected from the radicals A1.p' 1 to A1.p' 81.

Table 80: Compounds of the formula I'.A and the salts and N-oxides thereof, wherein $R^1$ is methyl, $R^r$, $R^u$ and $R^w$ are hydrogen and wherein A is selected from the radicals A1.p' 1 to A1.p' 81.

Table 81: Compounds of the formula I'.A and the salts and N-oxides thereof, wherein $R^1$, $R^r$, $R^u$ and $R^w$ are hydrogen and wherein A is selected from the radicals A1.q' 1 to A1.q' 81.

Table 82: Compounds of the formula I'.A and the salts and N-oxides thereof, wherein $R^1$ is methyl, $R^r$, $R^u$ and $R^w$ are hydrogen and wherein A is selected from the radicals A1.q' 1 to A1.q' 81.

Table 83: Compounds of the formula I'.A and the salts and N-oxides thereof, wherein $R^1$, $R^r$, $R^u$ and $R^w$ are hydrogen and wherein A is selected from the radicals A1.r' 1 to A1.r' 81.

Table 84: Compounds of the formula I'.A and the salts and N-oxides thereof, wherein $R^1$ is methyl, $R^r$, $R^u$ and $R^w$ are hydrogen and wherein A is selected from the radicals A1.r' 1 to A1.r' 81.

Table 85: Compounds of the formula I'.A and the salts and N-oxides thereof, wherein $R^1$, $R^r$, $R^u$ and $R^w$ are hydrogen and wherein A is selected from the radicals A1.s' 1 to A1.s' 81.

Table 86: Compounds of the formula I'.A and the salts and N-oxides thereof, wherein $R^1$ is methyl, $R^r$, $R^u$ and $R^w$ are hydrogen and wherein A is selected from the radicals A1.s' 1 to A1.s' 81.

Table 87: Compounds of the formula I'.A and the salts and N-oxides thereof, wherein $R^1$, $R^r$, $R^u$ and $R^w$ are hydrogen and wherein A is selected from the radicals A1.t' 1 to A1.t' 81.

Table 88: Compounds of the formula I'.A and the salts and N-oxides thereof, wherein $R^1$ is methyl, $R^r$, $R^u$ and $R^w$ are hydrogen and wherein A is selected from the radicals A1.t' 1 to A1.t' 81.

Table 89: Compounds of the formula I'.A and the salts and N-oxides thereof, wherein $R^1$, $R^r$, $R^u$ and $R^w$ are hydrogen and wherein A is selected from the radicals A1.u' 1 to A1.u' 81.

Table 90: Compounds of the formula I'.A and the salts and N-oxides thereof, wherein $R^1$ is methyl, $R^r$, $R^u$ and $R^w$ are hydrogen and wherein A is selected from the radicals A1.u' 1 to A1.u' 81.

Table 91: Compounds of the formula I'.A and the salts and N-oxides thereof, wherein $R^1$, $R^r$, $R^u$ and $R^w$ are hydrogen and wherein A is selected from the radicals A1.v' 1 to A1.v' 81.

Table 92: Compounds of the formula I'.A and the salts and N-oxides thereof, wherein $R^1$ is methyl, $R^r$, $R^u$ and $R^w$ are hydrogen and wherein A is selected from the radicals A1.v' 1 to A1.v' 81.

Table 93: Compounds of the formula I'.A and the salts and N-oxides thereof, wherein $R^1$, $R^r$, $R^u$ and $R^w$ are hydrogen and wherein A is selected from the radicals A1.w' 1 to A1.w' 81.

Table 94: Compounds of the formula I'.A and the salts and N-oxides thereof, wherein $R^1$ is methyl, $R^r$, $R^u$ and $R^w$ are hydrogen and wherein A is selected from the radicals A1.w' 1 to A1.w' 81.

Table 95: Compounds of the formula I'.A and the salts and N-oxides thereof, wherein $R^1$, $R^r$, $R^u$ and $R^w$ are hydrogen and wherein A is selected from the radicals A1.x' 1 to A1.x' 81.

Table 96: Compounds of the formula I'.A and the salts and N-oxides thereof, wherein $R^1$ is methyl, $R^r$, $R^u$ and $R^w$ are hydrogen and wherein A is selected from the radicals A1.x' 1 to A1.x' 81.

Table 97: Compounds of the formula I'.A and the salts and N-oxides thereof, wherein $R^1$, $R^r$, $R^u$ and $R^w$ are hydrogen and wherein A is selected from the radicals A1.y' 1 to A1.y' 81.

Table 98: Compounds of the formula I'.A and the salts and N-oxides thereof, wherein $R^1$ is methyl, $R^r$, $R^u$ and $R^w$ are hydrogen and wherein A is selected from the radicals A1.y' 1 to A1.y' 81.

Table 99: Compounds of the formula I'.A and the salts and N-oxides thereof, wherein $R^1$, $R^r$, $R^u$ and $R^w$ are hydrogen and wherein A is selected from the radicals A1.z' 1 to A1.z' 81.

Table 100: Compounds of the formula I'.A and the salts and N-oxides thereof, wherein $R^1$ is methyl, $R^r$, $R^u$ and $R^w$ are hydrogen and wherein A is selected from the radicals A1.z' 1 to A1.z' 81.

Further examples of compounds of this particularly preferred embodiment are the compounds of tables 51A to 100A wherein $R^r$, $R^u$ and $R^v$ are hydrogen and wherein A is as defined in tables 51 to 100 and wherein $R^1$ is a radical represented by each individual line (85 to 160) of table B.

Another particular preferred embodiment relates to compounds of the formula I'.A and to the salts and N-oxides thereof, wherein
A is a radical A1, as defined herein, in particular a radical A1, wherein $R^{41}$, $R^{51}$ have the preferred meanings, in particular an imidazole radical of the formulae A1.a' to A1.z', e.g. a radical selected from the thiazole radicals A1.a' to A1.z" 81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^r$, $R^u$, and $R^w$ are independently from each other selected from hydrogen, methyl, difluoromethyl, trifluoromethyl, methoxy, difluoromethoxy and trifluoromethoxy; and wherein preferably at least one, more preferably 2 or 3, of the radicals $R^r$, $R^u$, and $R^w$ are hydrogen.

Examples of compounds of this particularly preferred embodiment are the compounds given in the following tables 101 to 150

Table 101: Compounds of the formula I'.A and the salts and N-oxides thereof, wherein $R^r$, $R^u$ and $R^w$ are hydrogen and wherein A is selected from the radicals A1.a" 1 to A1.a" 81.

Table 102: Compounds of the formula I'.A and the salts and N-oxides thereof, wherein $R^1$ is methyl, $R^r$, $R^u$ and $R^w$ are hydrogen and wherein A is selected from the radicals A1.a" 1 to A1.a" 81.

Table 103: Compounds of the formula I'.A and the salts and N-oxides thereof, wherein $R^1$, $R^r$, $R^u$ and $R^w$ are hydrogen and wherein A is selected from the radicals A1.b" 1 to A1.b" 81.

Table 104: Compounds of the formula I'.A and the salts and N-oxides thereof, wherein $R^1$ is methyl, $R^r$, $R^u$ and $R^w$ are hydrogen and wherein A is selected from the radicals A1.b" 1 to A1.b" 81.

Table 105: Compounds of the formula I.A and the salts and N-oxides thereof, wherein $R^1$, $R^r$, $R^u$ and $R^w$ are hydrogen and wherein A is selected from the radicals A1.c" 1 to A1.c" 81.

Table 106: Compounds of the formula I'.A and the salts and N-oxides thereof, wherein $R^1$ is methyl, $R^r$, $R^u$ and $R^w$ are hydrogen and wherein A is selected from the radicals A1.c" 1 to A1.c" 81.

Table 107: Compounds of the formula I'.A and the salts and N-oxides thereof, wherein $R^1$, $R^r$, $R^u$ and $R^w$ are hydrogen and wherein A is selected from the radicals A1.d" 1 to A1.d" 81.

Table 108: Compounds of the formula I'.A and the salts and N-oxides thereof, wherein $R^1$ is methyl, $R^r$, $R^u$ and $R^w$ are hydrogen and wherein A is selected from the radicals A1.d" 1 to A1.d" 81.

Table 109: Compounds of the formula I'.A and the salts and N-oxides thereof, wherein $R^1$, $R^r$, $R^u$ and $R^w$ are hydrogen and wherein A is selected from the radicals A1.e" 1 to A1.e" 81.

Table 110: Compounds of the formula I'.A and the salts and N-oxides thereof, wherein $R^1$ is methyl, $R^r$, $R^u$ and $R^w$ are hydrogen and wherein A is selected from the radicals A1.e" 1 to A1.e" 81.

Table 111: Compounds of the formula I'.A and the salts and N-oxides thereof, wherein $R^r$, $R^r$, $R^u$ and $R^w$ are hydrogen and wherein A is selected from the radicals A1.f" 1 to A1.f" 81.

Table 112: Compounds of the formula I'.A and the salts and N-oxides thereof, wherein $R^1$ is methyl, $R^r$, $R^u$ and $R^w$ are hydrogen and wherein A is selected from the radicals A1.f" 1 to A1.f" 81.

Table 113: Compounds of the formula I'.A and the salts and N-oxides thereof, wherein $R^1$, $R^r$, $R^u$ and $R^w$ are hydrogen and wherein A is selected from the radicals A1.g" 1 to A1.g" 81.

Table 114: Compounds of the formula I'.A and the salts and N-oxides thereof, wherein $R^1$ is methyl, $R^r$, $R^u$ and $R^w$ are hydrogen and wherein A is selected from the radicals A1.g" 1 to A1.g" 81.

Table 115: Compounds of the formula I'.A and the salts and N-oxides thereof, wherein $R^1$, $R^r$, $R^u$ and $R^w$ are hydrogen and wherein A is selected from the radicals A1.h" 1 to A1.h" 81.

Table 116: Compounds of the formula I'.A and the salts and N-oxides thereof, wherein $R^1$ is methyl, $R^r$, $R^u$ and $R^w$ are hydrogen and wherein A is selected from the radicals A1.h" 1 to A1.h" 81.

Table 117: Compounds of the formula I'.A and the salts and N-oxides thereof, wherein $R^1$, $R^r$, $R^u$ and $R^w$ are hydrogen and wherein A is selected from the radicals A1.i" 1 to A1.i" 81.

Table 118: Compounds of the formula I'.A and the salts and N-oxides thereof, wherein $R^1$ is methyl, $R^r$, $R^u$ and $R^w$ are hydrogen and wherein A is selected from the radicals A1.i" 1 to A1.i" 81.

Table 119: Compounds of the formula I'.A and the salts and N-oxides thereof, wherein $R^1$, $R^r$, $R^u$ and $R^w$ are hydrogen and wherein A is selected from the radicals A1.k" 1 to A1.k" 81.

Table 120: Compounds of the formula I'.A and the salts and N-oxides thereof, wherein $R^1$ is methyl, $R^r$, $R^u$ and $R^w$ are hydrogen and wherein A is selected from the radicals A1.k" 1 to A1.k" 81.

Table 121: Compounds of the formula I'.A and the salts and N-oxides thereof, wherein $R^1$, $R^r$, $R^u$ and $R^w$ are hydrogen and wherein A is selected from the radicals A1.l" 1 to A1.l" 81.

Table 122: Compounds of the formula I'.A and the salts and N-oxides thereof, wherein $R^1$ is methyl, $R^r$, $R^u$ and $R^w$ are hydrogen and wherein A is selected from the radicals A1.l" 1 to A1.l" 81.

Table 123: Compounds of the formula I'.A and the salts and N-oxides thereof, wherein $R^1$, $R^r$, $R^u$ and $R^w$ are hydrogen and wherein A is selected from the radicals A1.m" 1 to A1.m" 81.

Table 124: Compounds of the formula I'.A and the salts and N-oxides thereof, wherein $R^1$ is methyl, $R^r$, $R^u$ and $R^w$ are hydrogen and wherein A is selected from the radicals A1.m" 1 to A1.m" 81.

Table 125: Compounds of the formula I'.A and the salts and N-oxides thereof, wherein $R^1$, $R^r$, $R^u$ and $R^w$ are hydrogen and wherein A is selected from the radicals A1.n" 1 to A1.n" 81.

Table 126: Compounds of the formula I'.A and the salts and N-oxides thereof, wherein $R^1$ is methyl, $R^r$, $R^u$ and $R^w$ are hydrogen and wherein A is selected from the radicals A1.n" 1 to A1.n" 81.

Table 127: Compounds of the formula I'.A and the salts and N-oxides thereof, wherein $R^r$, $R^u$ and $R^w$ are hydrogen and wherein A is selected from the radicals A1.o" 1 to A1.o" 81.

Table 128: Compounds of the formula I'.A and the salts and N-oxides thereof, wherein $R^1$ is methyl, $R^r$, $R^u$ and $R^w$ are hydrogen and wherein A is selected from the radicals A1.o" 1 to A1.o" 81.

Table 129: Compounds of the formula I'.A and the salts and N-oxides thereof, wherein $R^1$, $R^r$, $R^u$ and $R^w$ are hydrogen and wherein A is selected from the radicals A1.p" 1 to A1.p" 81.

Table 130: Compounds of the formula I'.A and the salts and N-oxides thereof, wherein $R^1$ is methyl, $R^r$, $R^u$ and $R^w$ are hydrogen and wherein A is selected from the radicals A1.p" 1 to A1.p" 81.

Table 131: Compounds of the formula I'.A and the salts and N-oxides thereof, wherein $R^1$, $R^t$, $R^u$ and $R^w$ are hydrogen and wherein A is selected from the radicals A1.q" 1 to A1.q" 81.

Table 132: Compounds of the formula I'.A and the salts and N-oxides thereof, wherein $R^1$ is methyl, $R^t$, $R^u$ and $R^w$ are hydrogen and wherein A is selected from the radicals A1.q" 1 to A1.q" 81.

Table 133: Compounds of the formula I'.A and the salts and N-oxides thereof, wherein $R^t$, $R^u$ and $R^w$ are hydrogen and wherein A is selected from the radicals A1.r" 1 to A1.r" 81.

Table 134: Compounds of the formula I'.A and the salts and N-oxides thereof, wherein $R^1$ is methyl, $R^t$, $R^u$ and $R^w$ are hydrogen and wherein A is selected from the radicals A1.r" 1 to A1.r" 81.

Table 135: Compounds of the formula I'.A and the salts and N-oxides thereof, wherein $R^1$, $R^t$, $R^u$ and $R^w$ are hydrogen and wherein A is selected from the radicals A1.s" 1 to A1.s" 81.

Table 136: Compounds of the formula I'.A and the salts and N-oxides thereof, wherein $R^1$ is methyl, $R^t$, $R^u$ and $R^w$ are hydrogen and wherein A is selected from the radicals A1.s" 1 to A1.s" 81.

Table 137: Compounds of the formula I'.A and the salts and N-oxides thereof, wherein $R^1$, $R^t$, $R^u$ and $R^w$ are hydrogen and wherein A is selected from the radicals A1.t" 1 to A1.t" 81.

Table 138: Compounds of the formula I'.A and the salts and N-oxides thereof, wherein $R^1$ is methyl, $R^t$, $R^u$ and $R^w$ are hydrogen and wherein A is selected from the radicals A1.t" 1 to A1.t" 81.

Table 139: Compounds of the formula I'.A and the salts and N-oxides thereof, wherein $R^1$, $R^t$, $R^u$ and $R^w$ are hydrogen and wherein A is selected from the radicals A1.u" 1 to A1.u" 81.

Table 140: Compounds of the formula I'.A and the salts and N-oxides thereof, wherein $R^1$ is methyl, $R^t$, $R^u$ and $R^w$ are hydrogen and wherein A is selected from the radicals A1.u" 1 to A1.u" 81.

Table 141: Compounds of the formula I'.A and the salts and N-oxides thereof, wherein $R^1$, $R^t$, $R^u$ and $R^w$ are hydrogen and wherein A is selected from the radicals A1.v" 1 to A1.v" 81.

Table 142: Compounds of the formula I'.A and the salts and N-oxides thereof, wherein $R^1$ is methyl, $R^t$, $R^u$ and $R^w$ are hydrogen and wherein A is selected from the radicals A1.v" 1 to A1.v" 81.

Table 143: Compounds of the formula I'.A and the salts and N-oxides thereof, wherein $R^1$, $R^t$, $R^u$ and $R^w$ are hydrogen and wherein A is selected from the radicals A1.w" 1 to A1.w" 81.

Table 144: Compounds of the formula I'.A and the salts and N-oxides thereof, wherein $R^1$ is methyl, $R^t$, $R^u$ and $R^w$ are hydrogen and wherein A is selected from the radicals A1.w" 1 to A1.w" 81.

Table 145: Compounds of the formula I'.A and the salts and N-oxides thereof, wherein $R^1$, $R^t$, $R^u$ and $R^w$ are hydrogen and wherein A is selected from the radicals A1.x" 1 to A1.x" 81.

Table 146: Compounds of the formula I'.A and the salts and N-oxides thereof, wherein $R^1$ is methyl, $R^t$, $R^u$ and $R^w$ are hydrogen and wherein A is selected from the radicals A1.x" 1 to A1.x" 81.

Table 147: Compounds of the formula I'.A and the salts and N-oxides thereof, wherein $R^1$, $R^t$, $R^u$ and $R^w$ are hydrogen and wherein A is selected from the radicals A1.y" 1 to A1.y" 81.

Table 148: Compounds of the formula I'.A and the salts and N-oxides thereof, wherein $R^1$ is methyl, $R^t$, $R^u$ and $R^w$ are hydrogen and wherein A is selected from the radicals A1.y" 1 to A1.y" 81.

Table 149: Compounds of the formula I'.A and the salts and N-oxides thereof, wherein $R^1$, $R^t$, $R^u$ and $R^w$ are hydrogen and wherein A is selected from the radicals A1.z" 1 to A1.z" 81.

Table 150: Compounds of the formula I'.A and the salts and N-oxides thereof, wherein $R^1$ is methyl, $R^t$, $R^u$ and $R^w$ are hydrogen and wherein A is selected from the radicals A1.z" 1 to A1.z" 81.

Further examples of compounds of this particularly preferred embodiment are the cornpounds of tables 101A to 150A wherein $R^t$, $R^u$ and $R^v$ are hydrogen and wherein A is as defined in tables 101 to 126 and wherein $R^1$ is a radical represented by each individual line (85 to 160) of table B.

Another particular preferred embodiment relates to compounds of the formula I'.A and 401 to the salts and N-oxides thereof, wherein A is a radical A2, as defined herein, in particular a radical A2, wherein $R^{42}$, $R^{52}$ have the preferred meanings, in particular an oxazole radical of the formulae A2.aa to A2.do, e.g. a radical selected from the oxazole radicals A2.aa1-A2.aa81 to A2.do1 to A2.do81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^t$, $R^u$ and $R^w$ are selected independently of each other from hydrogen, methyl, difluoromethyl, trifluoromethyl, methoxy, difluoromethoxy and trifluoromethoxy; and wherein preferably at least one, more preferably two or three of the radicals $R^t$, $R^u$ and $R^w$ are hydrogen.

Examples of compounds of this particular preferred embodiment are the compounds given in the following tables 151 to 176.

Table 151: Compounds of the formula I'.A and the salts and N-oxides thereof, wherein $R^t$, $R^u$ and $R^w$ are hydrogen and wherein A is selected from the radicals A2.aa1 to A2.aa81.

Table 152: Compounds of the formula I'.A and the salts and N-oxides thereof, wherein $R^1$ is methyl, $R^t$, $R^u$ and $R^w$ are hydrogen and wherein A is selected from the radicals A2.aa1 to A2.aa81.

Table 153: Compounds of the formula I'.A and the salts and N-oxides thereof, wherein $R^1$, $R^t$, $R^u$ and $R^w$ are hydrogen and wherein A is selected from the radicals A2.ab1 to A2.ab81.

Table 154: Compounds of the formula I'.A and the salts and N-oxides thereof, wherein $R^1$ is methyl, $R^t$, $R^u$ and $R^w$ are hydrogen and wherein A is selected from the radicals A2.ab1 to A2.ab81.

Table 155: Compounds of the formula I'.A and the salts and N-oxides thereof, wherein $R^t$, $R^u$ and $R^w$ are hydrogen and wherein A is selected from the radicals A2.ac1 to A2.ac81.

Table 156: Compounds of the formula I'.A and the salts and N-oxides thereof, wherein $R^1$, is methyl, $R^t$, $R^u$ and $R^w$ are hydrogen and wherein A is selected from the radicals A2.ac1 to A2.ac81.

Table 157: Compounds of the formula I'.A and the salts and N-oxides thereof, wherein $R^1$, $R^2$ and $R^3$ are hydrogen and wherein A is selected from the radicals A2.ad1 to A2.ad81.

Table 158: Compounds of the formula I'.A and the salts and N-oxides thereof, wherein $R^1$ is methyl, $R^t$, $R^u$ and $R^w$ are hydrogen and wherein A is selected from the radicals A2.ad1 to A2.ad81.

Table 159: Compounds of the formula I'.A and the salts and N-oxides thereof, wherein $R^1$, $R^r$, $R^u$ and $R^w$ are hydrogen and wherein A is selected from the radicals A2.ae1 to A2.ae81.

Table 160: Compounds of the formula I'.A and the salts and N-oxides thereof, wherein $R^1$ is methyl, $R^r$, $R^u$ and $R^w$ are hydrogen and wherein A is selected from the radicals A2.ae1 to A2.ae81.

Table 161: Compounds of the formula I'.A and the salts and N-oxides thereof, wherein $R^1$, $R^r$, $R^u$ and $R^w$ are hydrogen and wherein A is selected from the radicals A2.af1 to A2.af81.

Table 162: Compounds of the formula I'.A and the salts and N-oxides thereof, wherein $R^1$ is methyl, $R^r$, $R^u$ and $R^w$ are hydrogen and wherein A is selected from the radicals A2.af1 to A2.af81.

Table 163: Compounds of the formula I'.A and the salts and N-oxides thereof, wherein $R^1$, $R^r$, $R^u$ and $R^w$ are hydrogen and wherein A is selected from the radicals A2.ag1 to A2.ag81.

Table 164: Compounds of the formula I'.A and the salts and N-oxides thereof, wherein $R^1$ is methyl, $R^r$, $R^u$ and $R^w$ are hydrogen and wherein A is selected from the radicals A2.ag1 to A2.ag81.

Table 165: Compounds of the formula I'.A and the salts and N-oxides thereof, wherein $R^1$, $R^r$, $R^u$ and $R^w$ are hydrogen and wherein A is selected from the radicals A2.ai1 to A2.ai81.

Table 166: Compounds of the formula I'.A and the salts and N-oxides thereof, wherein $R^1$ is methyl, $R^r$, $R^u$ and $R^w$ are hydrogen and wherein A is selected from the radicals A2.ai1 to A2.ai81.

Table 167: Compounds of the formula I'.A and the salts and N-oxides thereof, wherein $R^r$, $R^u$ and $R^w$ are hydrogen and wherein A is selected from the radicals A2.ak1 to A2.ak81.

Table 168: Compounds of the formula I'.A and the salts and N-oxides thereof, wherein $R^1$ is methyl, $R^r$, $R^u$ and $R^w$ are hydrogen and wherein A is selected from the radicals A2.ak1 to A2.ak81.

Table 169: Compounds of the formula I'.A and the salts and N-oxides thereof, wherein $R^r$, $R^u$ and $R^w$ are hydrogen and wherein A is selected from the radicals A2.al1 to A2.al81.

Table 170: Compounds of the formula I'.A and the salts and N-oxides thereof, wherein $R^1$ is methyl, $R^r$, $R^u$ and $R^w$ are hydrogen and wherein A is selected from the radicals A2.al1 to A2.al81.

Table 171: Compounds of the formula I'.A and the salts and N-oxides thereof, wherein $R^r$, $R^u$ and $R^w$ are hydrogen and wherein A is selected from the radicals A2.am1 to A2.am81.

Table 172: Compounds of the formula I'.A and the salts and N-oxides thereof, wherein $R^1$ is methyl, $R^r$, $R^u$ and $R^w$ are hydrogen and wherein A is selected from the radicals A2.am1 to A2.am81.

Table 173: Compounds of the formula I'.A and the salts and N-oxides thereof, wherein $R^1$, $R^r$, $R^u$ and $R^w$ are hydrogen and wherein A is selected from the radicals A2.an1 to A2.an81.

Table 174: Compounds of the formula I'.A and the salts and N-oxides thereof, wherein $R^1$ is methyl, $R^r$, $R^u$ and $R^w$ are hydrogen and wherein A is selected from the radicals A2.an1 to A2.an81.

Table 175: Compounds of the formula I'.A and the salts and N-oxides thereof, wherein $R^1$, $R^r$, $R^u$ and $R^w$ are hydrogen and wherein A is selected from the radicals A2.ao1 to A2.ao81.

Table 176: Compounds of the formula I'.A and the salts and N-oxides thereof, wherein $R^1$ is methyl, $R^r$, $R^u$ and $R^w$ are hydrogen and wherein A is selected from the radicals A2.ao1 to A2.ao81.

Further examples of compounds of this particularly preferred embodiment are the compounds of tables 151A to 176A wherein $R^r$, $R^u$ and $R^v$ are hydrogen and wherein A is as defined in tables 153 to 180 and wherein $R^1$ is a radical represented by each individual line (85 to 160) of table B.

Another particular preferred embodiment relates to compounds of the formula I'.A and to the salts and N-oxides thereof, wherein A is a radical A2, as defined herein, in particular a radical A2, wherein $R^{42}$, $R^{52}$ have the preferred meanings, in particular a thiazole radical of the formulae A2.aa' to A2.do', e.g. a radical selected from the thiazole radicals A2.aa' 1-A2.aa' 81 to A2.do' 1 to A2.do' 81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^r$, $R^u$ and $R^w$ are selected independently of each other from hydrogen, methyl, difluoromethyl, trifluoromethyl, methoxy, difluoromethoxy and trifluoromethoxy; and wherein preferably at least one, more preferably two or three of the radicals $R^r$, $R^u$ and $R^w$ are hydrogen.

Examples of compounds of this particular preferred embodiment are the compounds given in the following tables 177 to 202.

Table 177: Compounds of the formula I'.A and the salts and N-oxides thereof, wherein $R^1$, $R^r$, $R^u$ and $R^w$ are hydrogen and wherein A is selected from the radicals A2.aa' 1 to A2.aa' 81.

Table 178: Compounds of the formula I'.A and the salts and N-oxides thereof, wherein $R^1$ is methyl, $R^r$, $R^u$ and $R^w$ are hydrogen and wherein A is selected from the radicals A2.aa' 1 to A2.aa' 81.

Table 179: Compounds of the formula I'.A and the salts and N-oxides thereof, wherein $R^1$, $R^r$, $R^u$ and $R^w$ are hydrogen and wherein A is selected from the radicals A2.ab' 1 to A2.ab' 81.

Table 180: Compounds of the formula I'.A and the salts and N-oxides thereof, wherein $R^1$ is methyl, $R^r$, $R^u$ and $R^w$ are hydrogen and wherein A is selected from the radicals A2.ab' 1 to A2.ab' 81.

Table 181: Compounds of the formula I'.A and the salts and N-oxides thereof, wherein $R^1$, $R^r$, $R^u$ and $R^w$ are hydrogen and wherein A is selected from the radicals A2.ac' 1 to A2.ac' 81.

Table 182: Compounds of, the formula I'.A and the salts and N-oxides thereof, wherein $R^1$ is methyl, $R^r$, $R^u$ and $R^w$ are hydrogen and wherein A is selected from the radicals A2.ac' 1 to A2.ac' 81.

Table 183: Compounds of the formula I'.A and the salts and N-oxides thereof, wherein $R^1$, $R^2$ and $R^3$ are hydrogen and wherein A is selected from the radicals A2.ad' 1 to A2.ad' 81.

Table 184: Compounds of the formula I'.A and the salts and N-oxides thereof, wherein $R^1$ is methyl, $R^r$, $R^u$ and $R^w$ are hydrogen and wherein A is selected from the radicals A2.ad' 1 to A2.ad' 81.

Table 185: Compounds of the formula I'.A and the salts and N-oxides thereof, wherein $R^1$, $R^r$, $R^u$ and $R^w$ are hydrogen and wherein A is selected from the radicals A2.ae' 1 to A2.ae' 81.

Table 186: Compounds of the formula I'.A and the salts and N-oxides thereof, wherein $R^1$ is methyl, $R^t$, $R^u$ and $R^w$ are hydrogen and wherein A is selected from the radicals A2.ae' 1 to A2.ae' 81.

Table 187: Compounds of the formula I'.A and the salts and N-oxides thereof, wherein $R^1$, $R^t$, $R^u$ and $R^w$ are hydrogen and wherein A is selected from the radicals A2.af' 1 to A2.af' 81.

Table 188: Compounds of the formula I'.A and the salts and N-oxides thereof, wherein $R^1$ is methyl, $R^t$, $R^u$ and $R^w$ are hydrogen and wherein A is selected from the radicals A2.af' 1 to A2.af' 81.

Table 189: Compounds of the formula I'.A and the salts and N-oxides thereof, wherein $R^1$, $R^t$, $R^u$ and $R^w$ are hydrogen and wherein A is selected from the radicals A2.ag' 1 to A2.ag' 81.

Table 190: Compounds of the formula I'.A and the salts and N-oxides thereof, wherein $R^1$ is methyl, $R^t$, $R^u$ and $R^w$ are hydrogen and wherein A is selected from the radicals A2.ag' 1 to A2.ag' 81.

Table 191: Compounds of the formula I'.A and the salts and N-oxides thereof, wherein $R^1$, $R^t$, $R^u$ and $R^w$ are hydrogen and wherein A is selected from the radicals A2.ai' 1 to A2.ai' 81.

Table 192: Compounds of the formula I'.A and the salts and N-oxides thereof, wherein $R^1$ is methyl, $R^t$, $R^u$ and $R^w$ are hydrogen and wherein A is selected from the radicals A2.ai' 1 to A2.ai' 81.

Table 193: Compounds of the formula I'.A and the salts and N-oxides thereof, wherein $R^1$, $R^t$, $R^u$ and $R^w$ are hydrogen and wherein A is selected from the radicals A2.ak' 1 to A2.ak' 81.

Table 194: Compounds of the formula I'.A and the salts and N-oxides thereof, wherein $R^1$ is methyl, $R^t$, $R^u$ and $R^w$ are hydrogen and wherein A is selected from the radicals A2.ak' 1 to A2.ak' 81.

Table 195: Compounds of the formula I'.A and the salts and N-oxides thereof, wherein $R^1$, $R^t$, $R^u$ and $R^w$ are hydrogen and wherein A is selected from the radicals A2.al' 1 to A2.al' 81.

Table 196: Compounds of the formula I'.A and the salts and N-oxides thereof, wherein $R^1$ is methyl, $R^t$, $R^u$ and $R^w$ are hydrogen and wherein A is selected from the radicals A2.al' 1 to A2.al' 81.

Table 197: Compounds of the formula I'.A and the salts and N-oxides thereof, wherein $R^t$, $R^u$ and $R^w$ are hydrogen and wherein A is selected from the radicals A2.am' 1 to A2.am' 81.

Table 198: Compounds of the formula I'.A and the salts and N-oxides thereof, wherein $R^1$ is methyl, $R^t$, $R^u$ and $R^w$ are hydrogen and wherein A is selected from the radicals A2.am' 1 to A2.am' 81.

Table 199: Compounds of the formula I'.A and the salts and N-oxides thereof, wherein $R^1$, $R^t$, $R^u$ and $R^w$ are hydrogen and wherein A is selected from the radicals A2.an' 1 to A2.an' 81.

Table 200: Compounds of the formula I'.A and the salts and N-oxides thereof, wherein $R^1$ is methyl, $R^t$, $R^u$ and $R^w$ are hydrogen and wherein A is selected from the radicals A2.an' 1 to A2.an' 81.

Table 201: Compounds of the formula I'.A and the salts and N-oxides thereof, wherein $R^1$, $R^t$, $R^u$ and $R^w$ are hydrogen and wherein A is selected from the radicals A2.ao' 1 to A2.ao' 81.

Table 202: Compounds of the formula I'.A and the salts and N-oxides thereof, wherein $R^1$ is methyl, $R^t$, $R^u$ and $R^w$ are hydrogen and wherein A is selected from the radicals A2.ao' 1 to A2.ao' 81.

Further examples of compounds of this particularly preferred embodiment are the compounds of tables 177A to 202A wherein $R^t$, $R^u$ and $R^v$ are hydrogen and wherein A is as defined in tables 176 to 202 and wherein $R^1$ is a radical represented by each individual line (85 to 160) of table B.

Another particular preferred embodiment relates to compounds of the formula I'.A and to the salts and N-oxides thereof, wherein A is a radical A2, as defined herein, in particular a radical A2, wherein $R^{42}$, $R^{52}$, $R^{63}$ have the preferred meanings, in particular an imidazole radical of the formulae A2.aa" to A2.do, e.g. a radical selected from the imidazole radicals A2.aa" 1-A2.aa" 81 to A2.do1 to A2.do81;

$R^1$ is hydrogen, C$_1$ralkyl or C$_1$ra-4-alkoxy-C$_1$-C$_2$-alkyl, most preferably hydrogen, methyl or ethyl;

$R^1$ is further most preferably represented by a radical as defined in each line of table B;

$R^t$, $R^u$ and $R^w$ are selected independently of each other from hydrogen, methyl, difluoromethyl, trifluoromethyl, methoxy, difluoromethoxy and trifluoromethoxy; and wherein preferably at least one, more preferably two or three of the radicals $R^t$, $R^u$ and $R^w$ are hydrogen.

Examples of compounds of this particular preferred embodiment are the compounds given in the following tables 203 to 313.

Table 203: Compounds of the formula I'.A and the salts and N-oxides thereof, wherein $R^1$, $R^t$, $R^u$ and $R^w$ are hydrogen and wherein A is selected from the radicals A2.aa" 1 to A2.aa" 81.

Table 204: Compounds of the formula I'.A and the salts and N-oxides thereof, wherein $R^1$ is methyl, $R^t$, $R^u$ and $R^w$ are hydrogen and wherein A is selected from the radicals A2.aa" 1 to A2.aa" 81.

Table 205: Compounds of the formula I'.A and the salts and N-oxides thereof, wherein $R^t$, $R^u$ and $R^w$ are hydrogen and wherein A is selected from the radicals A2.ab" 1 to A2.ab" 81.

Table 206: Compounds of the formula I'.A and the salts and N-oxides thereof, wherein $R^1$ is methyl, $R^t$, $R^u$ and $R^w$ are hydrogen and, wherein A is selected from the radicals A2.ab" 1 to A2.ab" 81.

Table 207: Compounds of the formula I'.A and the salts and N-oxides thereof, wherein $R^1$, $R^t$, $R^u$ and $R^w$ are hydrogen and wherein A is selected from the radicals A2.ac" 1 to A2.ac" 81.

Table 208: Compounds of the formula I'.A and the salts and N-oxides thereof, wherein $R^1$ is methyl, $R^t$, $R^u$ and $R^w$ are hydrogen and wherein A is selected from the radicals A2.ac" 1 to A2.ac" 81.

Table 209: Compounds of the formula I'.A and the salts and N-oxides thereof, wherein $R^1$, $R^2$ and $R^3$ are hydrogen and wherein A is selected from the radicals A2.ad" 1 to A2.ad" 81.

Table 210: Compounds of the formula I'.A and the salts and N-oxides thereof, wherein $R^1$ is methyl, $R^t$, $R^u$ and $R^w$ are hydrogen and wherein A is selected from the radicals A2.ad" 1 to A2.ad" 81.

Table 211: Compounds of the formula I'.A and the salts and N-oxides thereof, wherein $R^1$, $R^t$, $R^u$ and $R^w$ are hydrogen and wherein A is selected from the radicals A2.ae" 1 to A2.ae" 81.

Table 212: Compounds of the formula I'.A and the salts and N-oxides thereof, wherein $R^1$ is methyl, $R^r$, $R^u$ and $R^w$ are hydrogen and wherein A is selected from the radicals A2.ae" 1 to A2.ae" 81.

Table 213: Compounds of the formula I'.A and the salts and N-oxides thereof, wherein $R^1$, $R^u$ and $R^w$ are hydrogen and wherein A is selected from the radicals A2.af" 1 to A2.af" 81.

Table 214: Compounds of the formula I'.A and the salts and N-oxides thereof, wherein $R^1$ is methyl, $R^r$, $R^u$ and $R^w$ are hydrogen and wherein A is selected from the radicals A2.af" 1 to A2.af" 81.

Table 215: Compounds of the formula I'.A and the salts and N-oxides thereof, wherein $R^1$, $R^r$, $R^u$ and $R^w$ are hydrogen and wherein A is selected from the radicals A2.ag" 1 to A2.ag" 81.

Table 216: Compounds of the formula I'.A and the salts and N-oxides thereof, wherein $R^1$ is methyl, $R^r$, $R^u$ and $R^w$ are hydrogen and wherein A is selected from the radicals A2.ag" 1 to A2.ag" 81.

Table 217: Compounds of the formula I'.A and the salts and N-oxides thereof, wherein $R^1$, $R^r$, $R^u$ and $R^w$ are hydrogen and wherein A is selected from the radicals A2.ai" 1 to A2.ai" 81.

Table 218: Compounds of the formula I'.A and the salts and N-oxides thereof, wherein $R^1$ is methyl, $R^r$, $R^u$ and $R^w$ are hydrogen and wherein A is selected from the radicals A2.ai" 1 to A2.ai" 81.

Table 219: Compounds of the formula I'.A and the salts and N-oxides thereof, wherein $R^1$, $R^r$, $R^u$ and $R^w$ are hydrogen and wherein A is selected from the radicals A2.ak" 1 to A2.ak" 81.

Table 220: Compounds of the formula I'.A and the salts and N-oxides thereof, wherein $R^1$ is methyl, $R^r$, $R^u$ and $R^w$ are hydrogen and wherein A is selected from the radicals A2.ak" 1 to A2.ak" 81.

Table 221: Compounds of the formula I'.A and the salts and N-oxides thereof, wherein $R^1$, $R^u$ and $R^w$ are hydrogen and wherein A is selected from the radicals A2.al" 1 to A2.al" 81.

Table 222: Compounds of the formula I'.A and the salts and N-oxides thereof, wherein $R^1$ is methyl, $R^r$, $R^u$ and $R^w$ are hydrogen and wherein A is selected from the radicals A2.al" 1 to A2.al" 81.

Table 223: Compounds of the formula I'.A and the salts and N-oxides thereof, wherein $R^1$, $R^r$, $R^u$ and $R^w$ are hydrogen and wherein A is selected from the radicals A2.am" 1 to A2.am" 81.

Table 224: Compounds of the formula I'.A and the salts and N-oxides thereof, wherein $R^1$ is methyl, $R^r$, $R^u$ and $R^w$ are hydrogen and wherein A is selected from the radicals A2.am" 1 to A2.am" 81.

Table 225: Compounds of the formula I'.A and the salts and N-oxides thereof, wherein $R^1$, $R^r$, $R^u$ and $R^w$ are hydrogen and wherein A is selected from the radicals A2.an" 1 to A2.an" 81.

Table 226: Compounds of the formula I'.A and the salts and N-oxides thereof, wherein $R^1$ is methyl, $R^r$, $R^u$ and $R^w$ are hydrogen and wherein A is selected from the radicals A2.an" 1 to A2.an" 81.

Table 227: Compounds of the formula I'.A and the salts and N-oxides thereof, wherein $R^1$, $R^r$, $R^u$ and $R^w$ are hydrogen and wherein A is selected from the radicals A2.ao" 1 to A2.ao" 81.

Table 228: Compounds of the formula I'.A and the salts and N-oxides thereof, wherein $R^1$ is methyl, $R^r$, $R^u$ and $R^w$ are hydrogen and wherein A is selected from the radicals A2.ao" 1 to A2.ao" 81.

Table 229: Compounds of the formula I'.A and the salts and N-oxides thereof, wherein $R^1$, $R^r$, $R^u$ and $R^w$ are hydrogen and wherein A is selected from the radicals A2.ba1 to A2.ba81.

Table 230: Compounds of the formula I'.A and the salts and N-oxides thereof, wherein $R^1$ is methyl, $R^r$, $R^u$ and $R^w$ are hydrogen and wherein A is selected from the radicals A2.ba1 to A2.ba81.

Table 231: Compounds of the formula I'.A and the salts and N-oxides thereof, wherein $R^1$, $R^r$, $R^u$ and $R^w$ are hydrogen and wherein A is selected from the radicals A2.bb1 to A2.bb81.

Table 232: Compounds of the formula I'.A and the salts and N-oxides thereof, wherein $R^1$ is methyl, $R^r$, $R^u$ and $R^{w\,3}$ are hydrogen and wherein A is selected from the radicals A2.bb1 to A2.bb81.

Table 233: Compounds of the formula I'.A and the salts and N-oxides thereof, wherein $R^1$, $R^r$, $R^u$ and $R^w$ are hydrogen and wherein A is selected from the radicals A2.bc1 to A2.bc81.

Table 234: Compounds of the formula I'.A and the salts and N-oxides thereof, wherein $R^1$ is methyl, $R^r$, $R^u$ and $R^w$ are hydrogen and wherein A is selected from the radicals A2.bc1 to A2.bc81.

Table 235: Compounds of the formulaI'.A and, the salts and N-oxides thereof, wherein $R^1$, IT, $R^u$ and $R^w$ are hydrogen and wherein A is selected from the radicals A2.bd1 to A2.bd81.

Table 236: Compounds of the formula I'.A and the salts and N-oxides thereof, wherein $R^1$ is methyl, $R^r$, $R^u$ and $R^w$ are hydrogen and wherein A is selected from the radicals A2.bd1 to A2.bd81.

Table 237: Compounds of the formula I'.A and the salts and N-oxides thereof, wherein $R^1$, $R^r$, $R^u$ and $R^w$ are hydrogen and wherein A is selected from the radicals A2.be1 to A2.be81.

Table 238: Compounds of the formula I'.A and the salts and N-oxides thereof, wherein $R^1$ is methyl, $R^r$, $R^u$ and $R^w$ are hydrogen and wherein A is selected from the radicals A2.be1 to A2.be81.

Table 239: Compounds of the formula I'.A and the salts and N-oxides thereof, wherein $R^1$, $R^r$, $R^u$ and $R^w$ are hydrogen and wherein A is selected from the radicals A2.bf1 to A2.bf81.

Table 240: Compounds of the formula I'.A and the salts and N-oxides thereof, wherein $R^1$ is methyl, $R^r$, $R^u$ and $R^w$ are hydrogen and wherein A is selected from the radicals A2.bf1 to A2.bf81.

Table 241: Compounds of the formula I'.A and the salts and N-oxides thereof, wherein $R^1$, $R^r$, $R^u$ and $R^w$ are hydrogen and wherein A is selected from the radicals A2.bg1 to A2.bg81.

Table 242: Compounds of the formula I'.A and the salts and N-oxides thereof, wherein $R^1$ is methyl, $R^1$, $R^u$ and $R^w$ are hydrogen and wherein A is selected from the radicals A2.bg1 to A2.bg81.

Table 243: Compounds of the formula I'.A and the salts and N-oxides thereof, wherein $R^r$, $R^u$ and $R^w$ are hydrogen and wherein A is selected from the radicals A2.bi1 to A2.bi81.

Table 244: Compounds of the formula I'.A and the salts and N" oxides thereof, wherein $R^1$ is methyl, $R^r$, $R^u$ and $R^w$ are hydrogen and wherein A is selected from the radicals A2.bi1 to A2.bi81.

Table 245: Compounds of the formula I'.A and the salts and N-oxides thereof, wherein $R^1$, $R^r$, $R^u$ and $R^w$ are hydrogen and wherein A is selected from the radicals A2.bk1 to A2.bk81.

Table 246: Compounds of the formula I'.A and the salts and N-oxides thereof, wherein $R^r$ is methyl, $R^r$, $R^u$ and $R^w$ are hydrogen and wherein A is selected from the radicals A2.bk1 to A2.bk81.

Table 247: Compounds of the formula I'.A and the salts and N-oxides thereof, wherein $R^1$, $R^r$, $R^u$ and $R^w$ are hydrogen and wherein A is selected from the radicals A2.bl1 to A2.bl81.

Table 248: Compounds of the formula I'.A and the salts and N-oxides thereof, wherein $R^1$ is methyl, $R^r$, $R^u$ and $R^w$ are hydrogen and wherein A is selected from the radicals A2.bl1 to A2.bl81.

Table 249: Compounds of the formula I'.A and the salts and N-oxides thereof, wherein $R^1$, $R^u$ and $R^w$ are hydrogen and wherein A is selected from the radicals A2.bm1 to A2.bm81.

Table 250: Compounds of the formula I'.A and the salts and N-oxides thereof, wherein $R^1$ is methyl, $R^r$, $R^u$ and $R^w$ are hydrogen and wherein A is selected from the radicals A2.bm1 to A2.bm81.

Table 251: Compounds of the formula I'.A and the salts and N-oxides thereof, wherein $R^r$, $R^u$ and $R^w$ are hydrogen and wherein A is selected from the radicals A2.bn1 to A2.bn81.

Table 252: Compounds of the formula I'.A and the salts and N-oxides thereof, wherein $R^1$ is methyl, $R^r$, $R^u$ and $R^w$ are hydrogen and wherein A is selected from the radicals A2.bn1 to A2.bn81.

Table 253: Compounds of the formula I'.A and the salts and N-oxides thereof, wherein $R^1$, $R^r$, $R^u$ and $R^w$ are hydrogen and wherein A is selected from the radicals A2.bo1 to A2.bo81.

Table 254: Compounds of the formula I'.A and the salts and N-oxides thereof, wherein $R^1$ is methyl, $R^r$, $R^u$ and $R^w$ are hydrogen and wherein A is selected from the radicals A2.bo1 to A2.bo81.

Table 255: Compounds of the formula I'.A and the salts and N-oxides thereof, wherein $R^1$, $R^r$, $R^u$ and $R^w$ are hydrogen and wherein A is selected from the radicals A2.ca1 to A2.ca81.

Table 256: Compounds of the formula I'.A and the salts and N-oxides thereof, wherein $R^1$ is methyl, $R^r$, $R^u$ and $R^w$ are hydrogen and wherein A is selected from the radicals A2.ca1 to A2.ca81.

Table 257: Compounds of the formula I'.A and the salts and N-oxides thereof, wherein $R^1$, $R^r$, $R^u$ and $R^w$ are hydrogen and wherein A is selected from the radicals A2.cb1 to A2.cb81.

Table 258: Compounds of the formula I'.A and the salts and N-oxides thereof, wherein $R^1$ is methyl, $R^r$, $R^u$ and $R^w$ are hydrogen and wherein A is selected from the radicals A2.cb1 to A2.cb81.

Table 259: Compounds of the formula I'.A and the salts and N-oxides thereof, wherein $R^1$, $R^r$, $R^u$ and $R^w$ are hydrogen and wherein A is selected from the radicals A2.cc1 to A2.cc81.

Table 260: Compounds of the formula I'.A and the salts and N-oxides thereof, wherein $R^1$ is methyl, $R^r$, $R^u$ and $R^w$ are hydrogen and wherein A is selected from the radicals A2.cc1 to A2.cc81.

Table 261: Compounds of the formula I'.A and the salts and N-oxides thereof, wherein $R^r$, $R^u$ and $R^w$ are hydrogen and wherein A is selected from the radicals A2.cd1 to A2.cd81.

Table 262: Compounds of the formula I'.A and the salts and N-oxides thereof, wherein $R^1$ is methyl, $R^r$, $R^u$ and $R^w$ are hydrogen and wherein A is selected from the radicals A2.cd1 to A2.cd81.

Table 263: Compounds of the formula I'.A and the salts and N-oxides thereof, wherein $R^r$, $R^u$ and $R^w$ are hydrogen and wherein A is selected from the radicals A2.ce1 to A2.ce81.

Table 264: Compounds of the formula I'.A and the salts and N-oxides thereof, wherein $R^1$ is methyl, $R^r$, $R^u$ and $R^w$ are hydrogen and wherein A is selected from the radicals A2.ce1 to A2.ce81.

Table 265: Compounds of the formula I'.A and the salts and N-oxides thereof, wherein $R^1$, $R^r$, $R^u$ and $R^w$ are hydrogen and wherein A is selected from the radicals A2.cf1 to A2.cf81.

Table 266: Compounds of the formula I'.A and the salts and N-oxides thereof, wherein $R^1$ is methyl, $R^r$, $R^u$ and $R^w$ are hydrogen and wherein A is selected from the radicals A2.cf1 to A2.cf81.

Table 267: Compounds of the formula I'.A and the salts and N-oxides thereof, wherein $R^1$, $R^r$, $R^u$ and $R^w$ are hydrogen and wherein A is selected from the radicals A2.cg1 to A2.cg81.

Table 268: Compounds of the formula I'.A and the salts and N-oxides thereof, wherein $R^1$ is methyl, $R^r$, $R^u$ and $R^w$ are hydrogen and wherein A is selected from the radicals A2.cg1 to A2.cg81.

Table 269: Compounds of the formula I'.A and the salts and N-oxides thereof, wherein $R^1$, $R^r$, $R^u$ and $R^w$ are hydrogen and wherein A is selected from the radicals A2.ci1 to A2.ci81.

Table 270: Compounds of the formula I'.A and the salts and N-oxides thereof, wherein $R^1$ is methyl, $R^r$, $R^u$ and $R^w$ are hydrogen and wherein A is selected from the radicals A2.ci1 to A2.ci81.

Table 271: Compounds of the formula I'.A and the salts and N-oxides thereof, wherein $R^1$, $R^r$, $R^u$ and $R^w$ are hydrogen and wherein A is selected from the radicals A2.ck1 to A2.ck81.

Table 272: Compounds of the formula I'A and the salts and N-oxides thereof, wherein $R^1$ is methyl, $R^r$, $R^u$ and $R^w$ are hydrogen and wherein A is selected from the radicals A2.ck1 to A2.ck81.

Table 273: Compounds of the formula I'.A and the salts and N-oxides thereof, wherein $R^1$, $R^r$, $R^u$ and $R^w$ are hydrogen and wherein A is selected from the radicals A2.cl1 to A2.cl81.

Table 274: Compounds of the formula I'.A and the salts and N-oxides thereof, wherein $R^1$ is methyl, $R^r$, $R^u$ and $R^w$ are hydrogen and wherein A is selected from the radicals A2.cl1 to A2.cl81.

Table 275: Compounds of the formula I'.A and the salts and N-oxides thereof, wherein $R^1$, $R^r$, $R^u$ and $R^w$ are hydrogen and wherein A is selected from the radicals A2.cm1 to A2.cm81.

Table 276: Compounds of the formula I'.A and the salts and N-oxides thereof, wherein $R^1$ is methyl, $R^r$, $R^u$ and $R^w$ are hydrogen and wherein A is selected from the radicals A2.cm1 to A2.cm81.

Table 277: Compounds of the formula I'.A and the salts and N-oxides thereof, wherein $R^1$, $R^r$, $R^u$ and $R^w$ are hydrogen and wherein A is selected from the radicals A2.cn1 to A2.cn81.

Table 278: Compounds of the formula I'.A and the salts and N-oxides thereof, wherein $R^1$ is methyl, $R^r$, $R^u$ and $R^w$ are hydrogen and wherein A is selected from the radicals A2.cn1 to A2.cn81.

Table 279: Compounds of the formula I'.A and the salts and N-oxides thereof, wherein $R^1$, $R^r$, $R^u$ and $R^w$ are hydrogen and wherein A is selected from the radicals A2.co1 to A2.co81.

Table 280: Compounds of the formula I'.A and the salts and N-oxides thereof, wherein $R^1$ is methyl, $R^r$, $R^u$ and $R^w$ are hydrogen and wherein A is selected from the radicals A2.co1 to A2.co81.

Table 281: Compounds of the formula I'.A and the salts and N-oxides thereof, wherein $R^1$, $R^r$, $R^u$ and $R^w$ are hydrogen and wherein A is selected from the radicals A2.da1 to A2.da81.

Table 282: Compounds of the formula I'.A and the salts and N-oxides thereof, wherein $R^1$ is methyl, $R^r$, $R^u$ and $R^w$ are hydrogen and wherein A is selected from the radicals A2.da1 to A2.da81.

Table 283: Compounds of the formula I'.A and the salts and N-oxides thereof, wherein $R^1$, $R^r$, $R^u$ and $R^w$ are hydrogen and wherein A is selected from the radicals A2.db1 to A2.db81.

Table 284: Compounds of the formula I'.A and the salts and N-oxides thereof, wherein $R^1$ is methyl, $R^r$, $R^u$ and $R^w$ are hydrogen and wherein A is selected from the radicals A2.db1 to A2.db81.

Table 285: Compounds of the formula, I'.A and the salts and N-oxides thereof, wherein $R^1$, $R^r$, $R^u$ and $R^w$ are hydrogen and wherein A is selected from the radicals A2.dc1 to A2.dc81.

Table 286: Compounds of the formula I'.A and the salts and N-oxides thereof, wherein $R^1$ is methyl, $R^r$, $R^u$ and $R^w$ are hydrogen and wherein A is selected from the radicals A2.dc1 to A2.dc81.

Table 287: Compounds of the formula I'.A and the salts and N-oxides thereof, wherein $R^1$, $R^r$, $R^u$ and $R^N$ are hydrogen and wherein A is selected from the radicals A2.dd1 to A2.dd81.

Table 288: Compounds of the formula I'.A and the salts and N-oxides thereof, wherein $R^1$ is methyl, $R^r$, $R^u$ and $R^w$ are hydrogen and wherein A is selected from the radicals A2.dd1 to A2.dd81.

Table 289: Compounds of the formula I'.A and the salts and N-oxides thereof, wherein $R^1$, $R^u$ and $R^w$ are hydrogen, and wherein A is selected from the radicals A2.de1 to A2.de81.

Table 290 Compounds of the formula I'.A and the salts and N-oxides thereof, wherein $R^1$ is methyl, $R^r$, $R^u$ and $R^w$ are hydrogen and wherein A is selected from the radicals A2.de1 to A2.de81.

Table 291: Compounds of the formula I'.A and the salts and N-oxides thereof, wherein $R^1$, $R^r$, $R^u$ and $R^w$ are hydrogen and wherein A is selected from the radicals A2.df1 to A2.df81.

Table 292: Compounds of the formula I'.A and the salts and N-oxides thereof, wherein $R^1$ is methyl, $R^r$, $R^u$ and $R^w$ are, hydrogen and wherein A is selected from the radicals A2.df1 to A2.df81.

Table 293: Compounds of the formula I'.A and the salts and N-oxides thereof, wherein $R^1$, $R^r$, $R^u$ and $R^w$ are hydrogen and wherein A is selected from the radicals A2.dg1 to A2.dg81.

Table 294: Compounds of the formula I'.A and the salts and N-oxides thereof, wherein $R^1$ is methyl, $R^r$, $R^u$ and $R^w$ are hydrogen and wherein A is selected from the radicals A2.dg1 to A2.dg81.

Table 295: Compounds of the formula I'.A and the salts and N-oxides thereof, wherein $R^r$, $R^r$, $R^u$ and $R^w$ are hydrogen and wherein A is selected from the radicals A2.di1 to A2.di81.

Table 296: Compounds of the formula I'.A and the salts and N-oxides thereof, wherein $R^1$ is methyl, $R^r$, $R^u$ and $R^w$ are hydrogen and wherein A is selected from the radicals A2.di1 to A2.di81.

Table 297: Compounds of the formula I'.A and the salts and N-oxides thereof, wherein $R^1$, $R^r$, $R^u$ and $R^w$ are hydrogen and wherein A is selected from the radicals A2.dk1 to A2.dk81.

Table 298: Compounds of the formula I'.A and the salts and N-oxides thereof, wherein $R^1$ is methyl, $R^r$, $R^u$ and $R^w$ are hydrogen and wherein A is selected from the radicals A2.dk1 to A2.dk81.

Table 299: Compounds of the formula I'.A and the salts and N-oxides thereof, wherein $R^1$, $R^r$, $R^u$ and $R^w$ are hydrogen and wherein A is selected from the radicals A2.dl1 to A2.dl81.

Table 300: Compounds of the formula I'.A and the salts and N-oxides thereof, wherein $R^1$ is methyl, $R^r$, $R^u$ and $R^w$ are hydrogen and wherein A is selected from the radicals A2.dl1 to A2.dl81.

Table 301: Compounds of the formula I'.A and the salts and N-oxides thereof, wherein $R^1$, $R^r$, $R^u$ and $R^w$ are hydrogen and wherein A is selected from the radicals A2.dm1 to A2.dm81.

Table 302: Compounds of the formula I'.A and the salts and N-oxides thereof, wherein $R^1$ is methyl, $R^r$, $R^u$ and $R^w$ are hydrogen and wherein A is selected from the radicals A2.dm1 to A2.dm81.

Table 303: Compounds of the formula I'.A and the salts and N-oxides thereof, wherein $R^1$, $R^r$, $R^u$ and $R^w$ are hydrogen and wherein A is selected from the radicals A2.dn1 to A2.dn81.

Table 304: Compounds of the formula I'.A and the salts and N-oxides thereof, wherein $R^1$ is methyl, $R^r$, $R^u$ and $R^w$ are hydrogen and wherein A is selected from the radicals A2.dn1 to A2.dn81.

Table 305: Compounds of the formula I'.A and the salts and N-oxides thereof, wherein $R^r$, $R^r$, $R^u$ and $R^w$ are hydrogen and wherein A is selected from the radicals A2.do1 to A2.do81.

Table 306: Compounds of the formula I'.A and the salts and N-oxides thereof, wherein $R^1$ is methyl, $R^r$, $R^u$ and $R^w$ are hydrogen and wherein A is selected from the radicals A2.do1 to A2.do81.

Table 307: Compounds of the formula I'.A and the salts and N-oxides thereof, wherein $R^1$, $R^r$, $R^u$ and $R^w$ are hydrogen and wherein A is selected from the radicals A2.ea1 to A2.ea81.

Table 308: Compounds of the formula I'.A and the salts and N-oxides thereof, wherein $R^1$ is methyl, $R^r$, $R^u$ and $R^w$ are hydrogen and wherein A is selected from the radicals A2.ea1 to A2.ea81.

Table 309: Compounds of the formula I'.A and the salts and N-oxides thereof, wherein $R^1$, $R^r$, $R^u$ and $R^w$ are hydrogen and wherein A is selected from the radicals A2.fa1 to A2.fa81.

Table 310: Compounds of the formula I'.A and the salts and N-oxides thereof, wherein $R^1$ is methyl, $R^r$, $R^u$ and $R^w$ are hydrogen and wherein A is selected from the radicals A2.fa1 to A2.fa81.

Table 311: Compounds of the formula I'.A and the salts and N-oxides thereof, wherein $R^1$, $R^r$, $R^u$ and $R^w$ are hydrogen and wherein A is selected from the radicals A2.ga1 to A2.ga81.

Table 312: Compounds of the formula I'.A and the salts and N-oxides thereof, wherein $R^1$ is methyl, $R^r$, $R^u$ and $R^w$ are hydrogen and wherein A is selected from the radicals A2.ga1 to A2.ga81.

Table 313: Compounds of the formula I'.A and the salts and N-oxides thereof, wherein $R^1$, $R^r$, $R^u$ and $R^w$ are hydrogen and wherein A is selected from the radicals A2.ha1 to A2.ha81.

Further examples of compounds of this particularly preferred embodiment are the compounds of tables 203A to 313A wherein $R^r$, $R^u$ and $R^v$ are hydrogen and wherein A is as, defined in tables 203 to 313 and wherein $R^1$ is a radical represented by each individual line (85 to 160) of table B.

Another particular preferred embodiment relates to compounds of formula I'.A and to the salts and N-oxides thereof, wherein A is a radical A3, as defined herein, in particular a radical A3, wherein $R^{43}$, $R^{53}$ have the preferred meanings, more particularly an oxazole radical of the formulae A3.aa to A3.do, e.g. a radical selected from the oxazole radicals A3.aa1-A3.aa81 to A3.do1-A3.do81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^r$, $R^u$ and $R^w$ are selected independently of each other from hydrogen, methyl, difluoromethyl, trifluoromethyl, methoxy, difluoromethoxy and trifluoromethoxy; and wherein preferably at least one, more preferably 2 or 3, of the radicals $R^r$, $R^u$ and $R^w$ are hydrogen.

Examples of compounds of this particular preferred embodiment are the compounds given in the following tables 314 to 341.

Table 314: Compounds of the formula I'.A and the salts and N-oxides thereof, wherein $R^1$, $R^r$, $R^u$ and $R^w$ are hydrogen and wherein A is selected from the radicals A3.aa1 to A3.aa81.

Table 315: Compounds of the formula I.A and the salts and N-oxides thereof, wherein $R^1$ is methyl, $R^r$, $R^u$ and $R^w$ are hydrogen and wherein A is selected from the radicals A3.aa1 to A3.aa81.

Table 316: Compounds of the formula I'.A and the salts and N-oxides thereof, wherein $R^1$, $R^r$, $R^u$ and $R^w$ are hydrogen and wherein A is selected from the radicals A3.ab1 to A3.ab81.

Table 317: Compounds of the formula I.A and the salts and N-oxides thereof, wherein $R^1$ is methyl, $R^r$, $R^u$ and $R^w$ are hydrogen and wherein A is selected from the radicals A3.ab1 to A3.ab81.

Table 318: Compounds of the formula I'.A and the salts and N-oxides thereof, wherein $R^1$, $R^r$, $R^u$ and $R^w$ are hydrogen and wherein A is selected from the radicals A3.ac1 to A3.ac81.

Table 319: Compounds of the formula I'.A and the salts and N-oxides thereof, wherein $R^1$ is methyl, $R^r$, $R^u$ and $R^w$ are hydrogen and wherein A is selected from the radicals A3.ac1 to A3.ac81.

Table 320: Compounds of the formula I'.A and the salts and N-oxides thereof, wherein $R^r$, $R^u$ and $R^w$ are hydrogen and wherein A is selected from the radicals A3.ad1 to A3.ad81.

Table 321: Compounds of the formula I'.A and the salts and N-oxides thereof, wherein $R^1$ is methyl, $R^r$, $R^u$ and $R^w$ are hydrogen and wherein A is selected from the radicals A3.ad1 to A3.ad81.

Table 322: Compounds of the formula I'.A and the salts and N-oxides thereof, wherein $R^r$, $R^r$, $R^u$ and $R^w$ are hydrogen and wherein A is selected from the radicals A3.ae1 to A3.ae81.

Table 323: Compounds of the formula I'A and the salts and N-oxides thereof, wherein $R^1$ is methyl, $R^r$, $R^u$ and $R^w$ are hydrogen and wherein A is selected from the radicals A3.ae1 to A3.ae81.

Table 324: Compounds of the formula I'.A and the salts and N-oxides thereof, wherein $R^1$, $R^r$, $R^u$ and $R^w$ are hydrogen and wherein A is selected from the radicals A3.af1 to A3.af81.

Table 325: Compounds of the formula I'.A and the salts and N-oxides thereof, wherein $R^1$ is methyl, $R^r$, $R^u$ and $R^w$ are hydrogen and wherein A is selected from the radicals A3.af1 to A3.af81.

Table 326: Compounds of the formula I'.A and the salts and N-oxides thereof, wherein $R^1$, $R^r$, $R^u$ and $R^w$ are hydrogen and wherein A is selected from the radicals A3.ag1 to A3.ag81.

Table 327: Compounds of the formula I'.A and the salts and N-oxides thereof, wherein $R^1$ is methyl, $R^r$, $R^u$ and $R^w$ are hydrogen and wherein A is selected from the radicals A3.ag1 to A3.ag81.

Table 328: Compounds of the formula I'.A and the salts and N-oxides thereof, wherein $R^1$, $R^r$, $R^u$ and $R^w$ are hydrogen and wherein A is selected from the radicals A3.ah1 to A3.ah81.

Table 329: Compounds of the formula I'.A and the salts and N-oxides thereof, wherein $R^1$ is methyl, $R^r$, $R^u$ and $R^w$ are hydrogen and wherein A is selected from the radicals A3.ah1 to A3.ah81.

Table 330: Compounds of the formula I'.A and the salts and N-oxides thereof, wherein $R^1$, $R^u$ and $R^w$ are hydrogen and wherein A is selected from the radicals A3.ai1 to A3.ai81.

Table 331: Compounds of the formula I'.A and the salts and N-oxides thereof, wherein $R^1$ is methyl, $R^r$, $R^u$ and $R^w$ are hydrogen and wherein A is selected from the radicals A3.ai1 to A3.ai81.

Table 332: Compounds of the formula I'.A and the salts and N-oxides thereof, wherein $R^1$, $R^r$, $R^u$ and $R^w$ are hydrogen and wherein A is selected from the radicals A3.ak1 to A3.ak81.

Table 333: Compounds of the formula I'.A and the salts and N-oxides thereof, wherein $R^1$ is methyl, $R^r$, $R^u$ and $R^w$ are hydrogen and wherein A is selected from the radicals A3.ak1 to A3.ak81.

Table 334: Compounds of the formula I'.A and the salts and N-oxides thereof, wherein $R^1$, $R^r$, $R^u$ and $R^w$ are hydrogen and wherein A is selected from the radicals A3.al1 to A3.al81.

Table 335: Compounds of the formula I'.A and the salts and N-oxides thereof, wherein $R^1$ is methyl, $R^r$, $R^u$ and $R^w$ are hydrogen and wherein A is selected from the radicals A3.al1 to A3.al81.

Table 336: Compounds of the formula I'.A and the salts and N-oxides thereof, wherein $R^1$, $R^r$, $R^u$ and $R^w$ are hydrogen and wherein A is selected from the radicals A3.am1 to A3.am81.

Table 337: Compounds of the formula I'.A and the salts and N-oxides thereof, wherein $R^1$ is methyl, $R^r$, $R^u$ and $R^w$ are hydrogen and wherein A is selected from the radicals A3.am1 to A3.am81.

Table 338: Compounds of the formula I'.A and the salts and N-oxides thereof, wherein $R^r$, $R^u$ and $R^w$ are hydrogen and wherein A is selected from the radicals A3.an1 to A3.an81.

Table 339: Compounds of the formula I'.A and the salts and N-oxides thereof, wherein $R^1$ is methyl, $R^r$, $R^u$ and $R^w$ are hydrogen and wherein A is selected from the radicals A3.an1 to A3.an81.

Table 340: Compounds of the formula I'.A and the salts and N-oxides thereof, wherein $R^1$, $R^r$, $R^u$ and $R^w$ are hydrogen and wherein A is selected from the radicals A3.ao1 to A3.ao81.

Table 341: Compounds of the formula I'.A and the salts and N-oxides thereof, wherein $R^1$ is methyl, $R^r$, $R^u$ and $R^w$ are hydrogen and wherein A is selected from the radicals A3.ao1 to A3.ao81.

Further examples of compounds of this particularly preferred embodiment are the compounds of tables 314A to 341A wherein $R^r$, $R^u$ and $R^v$ are hydrogen and wherein A is as defined in tables 314 to 341 and wherein $R^1$ is a radical represented by each individual line (85 to 160) of table B.

Another particular preferred embodiment relates to compounds of formula I'.A and to the salts and N-oxides thereof, wherein A is a radical A3, as defined herein, in particular a radical A3, wherein $R^{43}$, $R^{53}$ have the preferred meanings, more particularly a thiazole radical of the formulae A3.aa' to A3.do', e.g. a radical selected from the thiazole radicals A3.aa' 1-A3.aa' 81 to A3.do' 1-A3.do' 81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^r$, $R^u$ and $R^w$ are selected independently of each other from hydrogen, methyl, difluoromethyl, trifluoromethyl, methoxy, difluoromethoxy and trifluoromethoxy; and wherein preferably at least one, more preferably 2 or 3, of the radicals $R^r$, $R^u$ and $R^w$ are hydrogen.

Examples of compounds of this particular preferred embodiment are the compounds given in the following tables 342 to 369.

Table 342: Compounds of the formula I'.A and the salts and N-oxides thereof, wherein $R^1$, $R^r$, $R^u$ and $R^w$ are hydrogen and wherein A is selected from the radicals A3.aa' 1 to A3.aa' 81.

Table 343: Compounds of the formula I'.A and the salts and N-oxides thereof, wherein $R^1$ is methyl, $R^r$, $R^u$ and $R^w$ are hydrogen and wherein A is selected from the radicals A3.aa' 1 to A3.aa' 81.

Table 344: Compounds of the formula I'.A and the salts and N-oxides thereof, wherein $R^1$, $R^r$, $R^u$ and $R^w$ are hydrogen and wherein A is selected from the radicals A3.ab' 1 to A3.ab' 81.

Table 345: Compounds of the formula I'.A and the salts and N-oxides thereof, wherein $R^1$ is methyl, $R^r$, $R^u$ and $R^w$ are hydrogen and wherein A is selected from the radicals A3.ab' 1 to A3.ab' 81.

Table 346: Compounds of the formula I'.A and the salts and N-oxides thereof, wherein $R^1$, $R^r$, $R^u$ and $R^w$ are hydrogen and wherein A is selected from the radicals A3.ac' 1 to A3.ac' 81.

Table 347: Compounds of the formula I'.A and the salts and N-oxides thereof, wherein $R^1$ is methyl, $R^r$, $R^u$ and $R^w$ are hydrogen and wherein A is selected from the radicals A3.ac' 1 to A3.ac' 81.

Table 348: Compounds of the formula I'.A and the salts and N-oxides thereof, wherein $R^1$, $R^r$, $R^u$ and $R^w$ are hydrogen and wherein A is selected from the radicals A3.ad' 1 to A3.ad' 81.

Table 349: Compounds of the formula I'.A and the salts and N-oxides thereof, wherein $R^1$ is methyl, $R^r$, $R^u$ and $R^w$ are hydrogen and wherein A is selected from the radicals A3.ad' 1 to A3.ad' 81.

Table 350: Compounds of the formula I'.A and the salts and N-oxides thereof, wherein $R^1$, $R^r$, $R^u$ and $R^w$ are hydrogen and wherein A is selected from the radicals A3.ae' 1 to A3.ae' 81.

Table 351: Compounds of the formula I'.A and the salts and N-oxides thereof, wherein $R^1$ is methyl, $R^r$, $R^u$ and $R^w$ are hydrogen and wherein A is selected from the radicals A3.ae' 1 to A3.ae' 81.

Table 352: Compounds of the formula I'.A and the salts and N-oxides thereof, wherein $R^1$, $R^r$, $R^u$ and $R^w$ are hydrogen and wherein A is selected from the radicals A3.af' 1 to A3.af' 81.

Table 353: Compounds of the formula I'.A and the salts and N-oxides thereof, wherein $R^1$ is methyl, IR % $R^u$ and $R^w$ are hydrogen and wherein A is selected from the radicals A3.af' 1 to A3.af' 81.

Table 354: Compounds of the formula I'.A and the salts and N-oxides thereof, wherein $R^1$, $R^r$, $R^u$ and $R^w$ are hydrogen and wherein A is selected from the radicals A3.ag' 1 to A3.ag' 81.

Table 355: Compounds of the formula I'.A and the salts and N-oxides thereof, wherein $R^1$ is methyl, $R^r$, $R^u$ and $R^w$ are hydrogen and wherein A is selected from the radicals A3.ag' 1 to A3.ag' 81.

Table 356: Compounds of the formula I'.A and the salts and N-oxides thereof, wherein $R^1$, $R^r$, $R^u$ and $R^w$ are hydrogen and wherein A is selected from the radicals A3.ah' 1 to A3.ah' 81.

Table 357: Compounds of the formula I'.A and the salts and N-oxides thereof, wherein $R^1$ is methyl, $R^r$, $R^u$ and $R^w$ are hydrogen and wherein A is selected from the radicals A3.ah' 1 to A3.ah' 81.

Table 358: Compounds of the formula I'.A and the salts and N-oxides thereof, wherein $R^1$, $R^r$, $R^u$ and $R^w$ are hydrogen and wherein A is selected from the radicals A3.ai' 1 to A3.ai' 81.

Table 359: Compounds of the formula I'.A and the salts and N-oxides thereof, wherein $R^1$ is methyl, $R^r$, $R^u$ and $R^w$ are hydrogen and wherein A is selected from the radicals A3.ai' 1 to A3.ai' 81.

Table 360: Compounds of the formula I'.A and the salts and N-oxides thereof, wherein $R^1$, $R^r$, $R^u$ and $R^w$ are hydrogen and wherein A is selected from the radicals A3.ak' 1 to A3.ak' 81.

Table 361: Compounds of the formula I'.A and the salts and N-oxides thereof, wherein $R^1$ is methyl, $R^r$, $R^u$ and $R^w$ are hydrogen and wherein A is selected from the radicals A3.ak' 1 to A3.ak' 81.

Table 362: Compounds of the formula I'.A and the salts and N-oxides thereof, wherein $R^1$, $R^r$, $R^u$ and $R^w$ are hydrogen and wherein A is selected from the radicals A3.al' 1 to A3.al' 81.

Table 363: Compounds of the formula I'.A and the salts and N-oxides thereof, wherein $R^1$ is methyl, $R^r$, $R^u$ and $R^N$ are hydrogen and wherein A is selected from the radicals A3.al' 1 to A3.al' 81.

Table 364 Compounds of the formula I'.A and the salts and N-oxides thereof, wherein $R^1$, $R^r$, $R^u$ and $R^w$ are hydrogen and wherein A is selected from the radicals A3.am' 1 to A3.am' 81.

Table 365: Compounds of the formula I'.A and the salts and N-oxides thereof, wherein $R^1$ is methyl, $R^t$, $R^u$ and $R^w$ are hydrogen and wherein A is selected from the radicals A3.am' 1 to A3.am' 81.

Table 366: Compounds of the formula I'.A and the salts and N-oxides thereof, wherein $R^t$, $R^t$, $R^u$ and $R^w$ are hydrogen and wherein I'.A is selected from the radicals A3.an' 1 to A3.an' 81.

Table 367: Compounds of the formula I'.A and the salts and N-oxides thereof, wherein $R^1$ is methyl, $R^t$, $R^u$ and $R^w$ are hydrogen and wherein A is selected from the radicals A3.an' 1 to A3.an' 81.

Table 368: Compounds of the formula I'.A and the salts and N-oxides thereof, wherein $R^1$, $R^t$, $R^u$ and $R^w$ are hydrogen and wherein A is selected from the radicals A3.ao' 1 to A3.ao' 81.

Table 369: Compounds of the formula I'.A and the salts and N-oxides thereof, wherein $R^1$ is methyl, $R^t$, $R^u$ and $R^w$ are hydrogen and wherein A is selected from the radicals A3.ao' 1 to A3.ao' 81.

Further examples of compounds of this particularly preferred embodiment are the compounds of tables 342A to 369A wherein $R^t$, $R^u$ and $R^w$ are hydrogen and wherein A is as defined in tables 342 to 369 and wherein $R^1$ is a radical represented by each individual line (85 to 160) of table B.

Another particular preferred embodiment relates to compounds of formula I'.A and to the salts and N-oxides thereof, wherein A is a radical A3, as defined herein, in particular a radical A3, wherein $R^{43}$, $R^{53}$ have the preferred meanings, more particularly an imidazole radical of the formulae A3.aa" to A3.fo, e.g. a radical selected from the thiazole radicals A3.aa" 1-A3.aa" 81 to A3.fo1-A3.fo81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^t$, $R^u$ and $R^w$ are selected independently of each other from hydrogen, methyl, difluoromethyl, trifluoromethyl, methoxy, difluoromethoxy and trifluoromethoxy; and wherein preferably at least one, more preferably 2 or 3, of the radicals $R^t$, $R^u$ and $R^w$ are hydrogen.

Examples of compounds of this particular preferred embodiment are the compounds given in the following tables 370 to 537.

Table 370: Compounds of the formula I'.A and the salts and N-oxides thereof, wherein $R^1$, $R^t$, $R^u$ and $R^w$ are hydrogen and wherein A is selected from the radicals A3.aa" 1 to A3.aa" 81.

Table 371: Compounds of the formula I'.A and the salts and N-oxides thereof, wherein $R^1$ is methyl, $R^t$, $R^u$ and $R^w$ are hydrogen and wherein A is selected from the radicals A3.aa" 1 to A3.aa" 81.

Table 372: Compounds of the formula I'.A and the salts and N-oxides thereof, wherein $R^1$, $R^t$, $R^u$ and $R^w$ are hydrogen and wherein A is selected from the radicals A3.ab" 1 to A3.ab" 81.

Table 373: Compounds of the formula I'.A and the salts and N-oxides thereof, wherein $R^1$ is methyl, $R^t$, $R^u$ and $R^w$ are hydrogen and wherein A is selected from the radicals A3.ab" 1 to A3.ab" 81.

Table 374: Compounds of the formula I'.A and the salts and N-oxides thereof, wherein $R^1$, $R^t$, $R^u$ and $R^w$ are hydrogen and wherein A is selected from the radicals A3.ac" 1 to A3.ac" 81.

Table 375: Compounds of the formula I'.A and the salts and N-oxides thereof, wherein $R^1$ is methyl, $R^t$, $R^u$ and $R^w$ are hydrogen and wherein A is selected from the radicals A3.ac" 1 to A3.ac" 81.

Table 376: Compounds of the formula I'.A and the salts and N-oxides thereof, wherein $R^1$, $R^t$, $R^u$ and $R^w$ are hydrogen and wherein A is selected from the radicals A3.ad" 1 to A3.ad" 81.

Table 377: Compounds of the formula I'.A and the salts and N-oxides thereof, wherein $R^1$ is methyl, IR', $R^u$ and $R^w$ are hydrogen and wherein A is selected from the radicals A3.ad" 1 to A3.ad" 81.

Table 378: Compounds of the formula I'.A and the salts and N-oxides thereof, wherein $R^1$, $R^t$, $R^u$ and $R^w$ are hydrogen and wherein A is selected from the radicals A3.ae" 1 to A3.ae" 81.

Table 379: Compounds of the formula I'.A and the salts and N-oxides thereof, wherein $R^1$ is methyl, $R^t$, $R^u$ and $R^w$ are hydrogen and wherein A is selected from the radicals A3.ae" 1 to A3.ae" 81.

Table 380: Compounds of the formula I'.A and the salts and N-oxides thereof, wherein $R^1$, $R^t$, $R^u$ and $R^w$ are hydrogen and wherein A is selected from the radicals A3.af" 1 to A3.af" 81.

Table 381: Compounds of the formula I'.A and the salts and N-oxides thereof, wherein $R^1$ is methyl, $R^t$, $R^u$ and $R^w$ are hydrogen and wherein A is selected from the radicals A3.af" 1 to A3.af" 81.

Table 382: Compounds of the formula I'.A and the salts and N-oxides thereof, wherein $R^1$, $R^t$, $R^u$ and $R^w$ are hydrogen and wherein A is selected from the radicals A3.ag" 1 to A3.ag" 81.

Table 383: Compounds of the formula I'.A and the salts and N-oxides thereof, wherein $R^1$ is methyl, $R^t$, $R^u$ and $R^w$ are hydrogen and wherein A is selected from the radicals A3.ag" 1 to A3.ag" 81.

Table 384: Compounds of the formula I'.A and the salts and N-oxides thereof, wherein $R^1$, $R^t$, $R^u$ and $R^w$ are hydrogen and wherein A is selected from the radicals A3.ah" 1 to A3.ah" 81.

Table 385: Compounds of the formula I'.A and the salts and N-oxides thereof, wherein $R^1$ is methyl, $R^t$, $R^u$ and $R^w$ are hydrogen and wherein A is selected from the radicals A3.ah" 1 to A3.ah" 81.

Table 386: Compounds of the formula I'.A and the salts and N-oxides thereof, wherein $R^1$, $R^t$, $R^u$ and $R^w$ are hydrogen and wherein A is selected from the radicals A3.ai" 1 to A3.ai" 81.

Table 387: Compounds of the formula I'.A and the salts and N-oxides thereof, wherein $R^1$ is methyl, $R^t$, $R^u$ and $R^w$ are hydrogen and wherein A is selected from the radicals A3.ai" 1 to A3.ai" 81.

Table 388: Compounds of the formula I'.A and the salts and N-oxides thereof, wherein $R^1$, $R^t$, $R^u$ and $R^w$ are hydrogen and wherein A is selected from the radicals A3.ak" 1 to A3.ak" 81.

Table 389: Compounds of the formula I'.A and the salts and N-oxides thereof, wherein $R^1$ is methyl, $R^t$, $R^u$ and $R^w$ are hydrogen and wherein A is selected from the radicals A3.ak" 1 to A3.ak" 81.

Table 390: Compounds of the formula I'.A and the salts and N-oxides thereof, wherein $R^1$, $R^t$, $R^u$ and $R^w$ are hydrogen and wherein A is selected from the radicals A3.al" 1 to A3.al" 81.

Table 391: Compounds of the formula I'.A and the salts and N-oxides thereof, wherein $R^1$ is methyl, $R^t$, $R^u$ and $R^w$ are hydrogen and wherein A is selected from the radicals A3.al" 1 to A3.al" 81.

Table 392: Compounds of the formula I'.A and the salts and N-oxides thereof, wherein $R^1$, $R^t$, $R^u$ and $R^w$ are hydrogen and wherein A is selected from the radicals A3.am" 1 to A3.am" 81.

Table 393: Compounds of the formula I'.A and the salts and N-oxides thereof, wherein $R^1$ is methyl, $R^t$, $R^u$ and $R^w$ are hydrogen and wherein A is selected from the radicals A3.am" 1 to A3.am" 81.

Table 394: Compounds of the formula I'.A and the salts and N-oxides thereof, wherein $R^1$, $R^t$, $R^u$ and $R^w$ are hydrogen and wherein A is selected from the radicals A3.an" 1 to A3.an" 81.

Table 395: Compounds of the formula I'.A and the salts and N-oxides thereof, wherein $R^1$ is methyl, $R^t$, $R^u$ and $R^w$ are hydrogen and wherein A is selected from the radicals A3.an" 1 to A3.an" 81.

Table 396: Compounds of the formula I'.A and the salts and N-oxides thereof, wherein $R^1$, $R^t$, $R^u$ and $R^w$ are hydrogen and wherein A is selected from the radicals A3.ao" 1 to A3.ao" 81.

Table 397: Compounds of the formula I'.A and the salts and N-oxides thereof, wherein $R^1$ is methyl, $R^t$, $R^u$ and $R^w$ are hydrogen and wherein A is selected from the radicals A3.ao" 1 to A3.ao" 81.

Table 398: Compounds of the formula I'.A and the salts and N-oxides thereof, wherein $R^1$, $R^t$, $R^u$ and $R^w$ are hydrogen and wherein A is selected from the radicals A3.ba1 to A3.ba81.

Table 399: Compounds of the formula I'.A and the salts and N-oxides thereof, wherein $R^1$ is methyl, $R^t$, $R^u$ and $R^w$ are hydrogen and wherein A is selected from the radicals A3.ba1 to A3.ba81.

Table 400: Compounds of the formula I'.A and the salts and N-oxides thereof, wherein $R^1$, $R^t$, $R^u$ and $R^w$ are hydrogen and wherein A is selected from the radicals A3.bb1 to A3.bb81.

Table 401: Compounds of the formula I'.A and the salts and N-oxides thereof, wherein $R^1$ is methyl, $R^t$, $R^u$ and $R^w$ are hydrogen and wherein A is selected from the radicals A3.bb1 to A3.bb81.

Table 402: Compounds of the formula I'.A and the salts and N-oxides thereof, wherein $R^1$, $R^t$, $R^u$ and $R^w$ are hydrogen and wherein A is selected from the radicals A3.bc1 to A3.bc81.

Table 403: Compounds of the formula I'.A and the salts and N-oxides thereof, wherein $R^1$ is methyl, $R^t$, $R^u$ and $R^w$ are hydrogen and wherein A is selected from the radicals A3.bc1 to A3.bc81.

Table 404: Compounds of the formula I'.A and the salts and N-oxides thereof, wherein $R^1$, $R^t$, $R^u$ and $R^w$ are hydrogen and wherein A is selected from the radicals A3.bd1 to A3.bd81.

Table 405: Compounds of the formula I'.A and the salts and N-oxides thereof, wherein $R^1$ is methyl, $R^t$, $R^u$ and $R^w$ are hydrogen and wherein A is selected from the radicals A3.bd1 to A3.bd81.

Table 406: Compounds of the formula I'.A and the salts and N-oxides thereof, wherein $R^1$, $R^t$, $R^u$ and $R^w$ are hydrogen and wherein A is selected from the radicals A3.be1 to A3.be81.

Table 407: Compounds of the formula I'.A and the salts and N-oxides thereof, wherein $R^1$ is methyl, $R^t$, $R^u$ and $R^w$ are hydrogen and wherein A is selected from the radicals A3.be1 to A3.be81.

Table 408: Compounds of the formula I'.A and the salts and N-oxides thereof, wherein $R^1$, $R^t$, $R^u$ and $R^w$ are hydrogen and wherein A is selected from the radicals A3.bf1 to A3.bf81.

Table 409: Compounds of the formula I'.A and the salts and N-oxides thereof, wherein $R^1$ is methyl, $R^t$, $R^u$ and $R^w$ are hydrogen and wherein A is selected from the radicals A3.bf1 to A3.bf81.

Table 410: Compounds of the formula I'.A and the salts and N-oxides thereof, wherein $R^1$, $R^t$, $R^u$ and $R^w$ are hydrogen and wherein A is selected from the radicals A3.bg1 to A3.bg81.

Table 411: Compounds of the formula I'.A and the salts and N-oxides thereof, wherein $R^1$ is methyl, $R^t$, $R^u$ and $R^w$ are hydrogen and wherein A is selected from the radicals A3.bg1 to A3.bg81.

Table 412: Compounds of the formula I'.A and the salts and N-oxides thereof, wherein $R^1$, $R^t$, $R^u$ and $R^w$ are hydrogen and wherein A is selected from the radicals A3.bh1 to A3.bh81.

Table 413: Compounds of the formula I'.A and the salts and N-oxides thereof, wherein $R^1$ is methyl, $R^t$, $R^u$ and $R^w$ are hydrogen and wherein A is selected from the radicals A3.bh1 to A3.bh81.

Table 414: Compounds of the formula I'.A and the salts and N-oxides thereof, wherein $R^1$, $R^t$, $R^u$ and $R^w$ are hydrogen and wherein A is selected from the radicals A3.bi1 to A3.bi81.

Table 415: Compounds of the formula I'.A and the salts and N-oxides thereof, wherein $R^1$ is methyl, $R^t$, $R^u$ and $R^w$ are hydrogen and wherein A is selected from the radicals A3.bi1 to A3.bi81.

Table 416: Compounds of the formula I'.A and the salts and N-oxides thereof, wherein $R^1$, $R^t$, $R^u$ and $R^w$ are hydrogen and wherein A is selected from the radicals A3.bk1 to A3.bk81.

Table 417: Compounds of the formula I'.A and the salts and N-oxides thereof, wherein $R^1$ is methyl, $R^t$, $R^u$ and $R^w$ are hydrogen and wherein A is selected from the radicals A3.bk1 to A3.bk81.

Table 418: Compounds of the formula I'.A and the salts and N-oxides thereof, wherein $R^1$, $R^t$, $R^u$ and $R^w$ are hydrogen and wherein A is selected from the radicals A3.bl1 to A3.bl81.

Table 419: Compounds of the formula I'.A and the salts and N-oxides thereof, wherein $R^1$ is methyl, $R^t$, $R^u$ and $R^w$ are hydrogen and wherein A is selected from the radicals A3.bl1 to A3.bl81.

Table 420: Compounds of the formula I'.A and the salts and N-oxides thereof, wherein $R^1$, $R^t$, $R^u$ and $R^w$ are hydrogen and wherein A is selected from the radicals A3.bm1 to A3.bm81.

Table 421: Compounds of the formula I'.A and the salts and N-oxides thereof, wherein $R^1$ is methyl, $R^t$, $R^u$ and $R^w$ are hydrogen and wherein A is selected from the radicals A3.bm1 to A3.bm81.

Table 422: Compounds of the formula I'.A and the salts and N-oxides thereof, wherein $R^1$, $R^t$, $R^u$ and $R^w$ are hydrogen and wherein A is selected from the radicals A3.bn1 to A3.bn81.

Table 423: Compounds of the formula I'.A and the salts and N-oxides thereof, wherein $R^1$ is methyl, $R^r$, $R^u$ and $R^w$ are hydrogen and wherein A is selected from the radicals A3.bn1 to A3.bn81.

Table 424: Compounds of the formula I'.A and the salts and N-oxides thereof, wherein $R^1$, $R^r$, $R^u$ and $R^w$ are hydrogen and wherein A is selected from the radicals A3.bo1 to A3.bo81.

Table 425: Compounds of the formula I'.A and the salts and N-oxides thereof, wherein $R^1$ is methyl, $R^r$, $R^u$ and $R^w$ are, hydrogen and wherein A is selected from the radicals A3.bo1 to A3.bo81.

Table 426: Compounds of the formula I'.A and, the salts and N-oxides thereof, wherein $R^1$, $R^r$, $R^u$ and $R^w$ are hydrogen and wherein A is selected from the radicals A3.ca1 to A3.ca81.

Table 427: Compounds of the formula I'.A and the salts and N-oxides thereof, wherein $R^1$ is methyl, $R^r$, $R^u$ and $R^w$ are hydrogen and wherein A is selected from the radicals A3.ca1 to A3.ca81.

Table 428: Compounds of the formula I'.A and the salts and N-oxides thereof, wherein $R^1$, $R^r$, $R^u$ and $R^w$ are hydrogen and wherein A is selected from the radicals A3.cb1 to A3.cb81.

Table 429: Compounds of the formula I'.A and the salts and N-oxides thereof, wherein $R^1$ is methyl, $R^r$, $R^u$ and $R^w$ are hydrogen and wherein A is selected from the radicals A3.cb1 to A3.cb81.

Table 430: Compounds of the formula I'.A and the salts and N-oxides thereof, wherein $R^1$, $R^r$, $R^u$ and $R^w$ are, hydrogen and wherein A is selected from the radicals A3.cc1 to A3.cc81.

Table 431: Compounds of the formula I'.A and the salts and N-oxides thereof, wherein $R^1$ is methyl, $R^r$, $R^u$ and $R^w$ are hydrogen and wherein A is selected from the radicals A3.cc1 to A3.cc81.

Table 432: Compounds of the formula I'.A and the salts and N-oxides thereof, wherein $R^1$, $R^r$, $R^u$ and $R^w$ are, hydrogen and wherein A is selected from the radicals A3.cd1 to A3.cd81.

Table 433: Compounds of the formula I'.A and, the salts and N-oxides thereof, wherein $R^1$ is methyl, $R^r$, $R^u$ and $R^w$ are hydrogen and wherein A is selected from the radicals A3.cd1 to A3.cd81.

Table 434: Compounds of the formula I'.A and the salts and N-oxides thereof, wherein $R^1$, $R^r$, $R^u$ and $R^w$ are hydrogen and wherein A is selected from the radicals A3.ce1 to A3.ce81.

Table 435: Compounds of the formula I'.A and the salts and N-oxides thereof, wherein $R^1$ is methyl, $R^r$, $R^u$ and $R^w$ are hydrogen and wherein A is selected from the radicals A3.ce1 to A3.ce81.

Table 436: Compounds of the formula I'.A and the salts and N-oxides thereof, wherein $R^1$, $R^r$, $R^u$ and $R^w$ are hydrogen and wherein A is selected from the radicals A3.cf1 to A3.cf81.

Table 437: Compounds of the formula I'.A and the salts and N-oxides thereof, wherein $R^1$ is methyl, $R^r$, $R^u$ and $R^w$ are hydrogen and wherein A is selected from the radicals A3.cf1 to A3.cf81.

Table 438: Compounds of the formula I'.A and the salts and N-oxides thereof, wherein $R^1$, $R^u$ and $R^w$ are hydrogen and wherein A is selected from the radicals A3.cg1 to A3.cg81.

Table 439: Compounds of the formula I'.A and the salts and N-oxides thereof, wherein $R^1$ is methyl, $R^r$, $R^u$ and $R^w$ are hydrogen and wherein A is selected from the radicals A3.cg1 to A3.cg81.

Table 440: Compounds of the formula I'.A and the salts and N-oxides thereof, wherein $R^r$, $R^u$ and $R^w$ are hydrogen and wherein A is selected from the radicals A3.ch1 to A3.ch81.

Table 441: Compounds of the formula I'.A and the salts and N-oxides thereof, wherein $R^1$ is methyl, $R^r$, $R^u$ and $R^w$ are hydrogen and wherein A is selected from the radicals A3.ch1 to A3.ch81.

Table 442: Compounds of the formula I'.A and the salts and N-oxides thereof, wherein $R^1$, $R^r$, $R^u$ and $R^w$ are hydrogen and wherein A is selected from the radicals A3.ci1 to A3.ci81.

Table 443: Compounds of the formula I'.A and the salts and N-oxides thereof, wherein $R^r$ is methyl, $R^r$, $R^u$ and $R^w$ are hydrogen and wherein A is selected from the radicals A3.ci1 to A3.ci81.

Table 444: Compounds of the formula I'.A and the salts and N-oxides thereof, wherein $R^1$, $R^r$, $R^u$ and $R^w$ are hydrogen and wherein A is selected from the radicals A3.ck1 to A3.ck81.

Table 445: Compounds of the formula I'.A and the salts and N-oxides thereof, wherein $R^1$ is methyl, $R^r$, $R^u$ and $R^w$ are hydrogen and wherein A is selected from the radicals A3.ck1 to A3.ck81.

Table 446: Compounds of the formula I'.A and the salts and N-oxides thereof, wherein $R^1$, $R^r$, $R^u$ and $R^w$ are hydrogen and wherein A is selected from the radicals A3.cl1 to A3.cl81.

Table 447: Compounds of the formula I'.A and the salts and N-oxides thereof, wherein $R^{-1}$ is methyl, $R^r$, $R^u$ and $R^w$ are hydrogen and wherein A is selected from the radicals A3.cl1 to A3.cl81.

Table 448: Compounds of the formula I'.A and the salts and N-oxides thereof, wherein $R^1$, $R^r$, $R^u$ and $R^w$ are hydrogen and wherein A is selected from the radicals A3.cm1 to A3.cm81.

Table 449: Compounds of the formula and the salts and N-oxides thereof, wherein $R^1$ is methyl, $R^r$, $R^u$ and $R^w$ are hydrogen and wherein A is selected from the radicals A3.cm1 to A3.cm81.

Table 450: Compounds of the formula I'.A and the salts and N-oxides thereof, wherein $R^1$, $R^r$, $R^u$ and $R^w$ are hydrogen and wherein A is selected from the radicals A3.cn1 to A3.cn81.

Table 451: Compounds of the formula I'.A and the salts and N-oxides thereof, wherein $R^1$ is methyl, $R^r$, $R^u$ and $R^w$ are hydrogen and wherein A is selected from the radicals A3.cn1 to A3.cn81.

Table 452: Compounds of the formula I'.A and the salts and N-oxides thereof, wherein $R^1$, $R^r$, $R^u$ and $R^w$ are hydrogen and wherein A is selected from the radicals A3.co1 to A3.co81.

Table 453: Compounds of the formula I'.A and the salts and N-oxides thereof, wherein $R^1$ is methyl, $R^r$, $R^u$ and $R^w$ are hydrogen and wherein A is selected from the radicals A3.co1 to A3.co81.

Table 454: Compounds of the formula I'.A and the salts and N-oxides thereof, wherein $R^1$, $R^r$, $R^u$ and $R^w$ are hydrogen and wherein A is selected from the radicals A3.da1 to A3.da81.

Table 455: Compounds of the formula I'.A and the salts and N-oxides thereof, wherein $R^1$ is methyl, $R^r$, $R^u$ and $R^w$ are hydrogen and wherein A is selected from the radicals A3.da1 to A3.da81.

Table 456: Compounds of the formula I'.A and the salts and N-oxides thereof, wherein $R^1$, $R^r$, $R^u$ and $R^w$ are hydrogen and wherein A is selected from the radicals A3.db1 to A3.db81.

Table 457: Compounds of the formula I'.A and the salts and N-oxides thereof, wherein $R^1$ is methyl, $R^t$, $R^u$ and $R^w$ are hydrogen and wherein A is selected from the radicals A3.db1 to A3.db81.

Table 458: Compounds of the formula I'.A and the salts and N-oxides thereof, wherein $R^1$, $R^t$, $R^u$ and $R^w$ are hydrogen and wherein A is selected from the radicals A3.dc1 to A3.dc81.

Table 459: Compounds of the formula I'.A and the salts and N-oxides thereof, wherein $R^1$ is methyl, $R^t$, $R^u$ and $R^w$ are hydrogen and wherein A is selected from the radicals A3.dc1 to A3.dc81.

Table 460: Compounds of the formula I'.A and the salts and N-oxides thereof, wherein $R^1$, $R^t$, $R^u$ and $R^w$ are hydrogen and wherein A is selected from the radicals A3.dd1 to A3.dd81.

Table 461: Compounds of the formula I'.A and the salts and N-oxides thereof, wherein $R^1$ is methyl, $R^t$, $R^u$ and $R^w$ are hydrogen and wherein A is selected from the radicals A3.dd1 to A3.dd81.

Table 462: Compounds of the formula I'.A and the salts and N-oxides thereof, wherein $R^1$, $R^t$, $R^u$ and $R^w$ are hydrogen and wherein A is selected from the radicals A3.de1 to A3.de81.

Table 463: Compounds of the formula I'.A and the salts and N-oxides thereof, wherein $R^1$ is methyl, $R^t$, $R^u$ and $R^w$ are hydrogen and wherein A is selected from the radicals A3.de1 to A3.de81.

Table 464: Compounds of the formula I'.A and the salts and N-oxides thereof, wherein $R^1$, $R^t$, $R^u$ and $R^w$ are hydrogen and wherein A is selected from the radicals A3.df1 to A3.df81.

Table 465: Compounds of the formula I'.A and the salts and N-oxides thereof, wherein $R^1$ is methyl, $R^t$, $R^u$ and $R^w$ are hydrogen and wherein A is selected from the radicals A3.df1 to A3.df81.

Table 466: Compounds of the formula I'.A and the salts and N-oxides thereof, wherein $R^1$, $R^t$, $R^u$ and $R^w$ are hydrogen and wherein A is selected from the radicals A3.dg1 to A3.dg81.

Table 467: Compounds of the formula I'.A and the salts and N-oxides thereof, wherein $R^1$ is methyl, $R^t$, $R^u$ and $R^w$ are hydrogen and wherein A is selected from the radicals A3.dg1 to A3_dg81.

Table 468: Compounds of the formula I'.A and the salts and N-oxides thereof, wherein $R^1$, $R^t$, $R^u$ and $R^w$ are hydrogen and wherein A is selected from the radicals A3.dh1 to A3.dh81.

Table 469: Compounds of the formula I'.A and the salts and N-oxides thereof, wherein $R^1$ is methyl, $R^t$, $R^u$ and $R^w$ are hydrogen and wherein A is selected from the radicals A3.dh1 to A3.dh81.

Table 470: Compounds of the formula I'.A and the salts and N-oxides thereof, wherein $R^1$, $R^t$, $R^u$ and $R^w$ are hydrogen and wherein A is selected from the radicals A3.di1 to A3.di81.

Table 471: Compounds of the formula I'.A and the salts and N-oxides thereof, wherein $R^1$ is methyl, $R^t$, $R^u$ and $R^w$ are hydrogen and wherein A is selected from the radicals A3.di1 to A3.di81.

Table 472: Compounds of the formula I'.A and the salts and N-oxides thereof, wherein $R^1$, $R^u$ and $R^w$ are hydrogen and wherein A is selected from the radicals A3.dk1 to A3.dk81.

Table 473: Compounds of the formula I'.A and the salts and N-oxides thereof, wherein $R^1$ is methyl, $R^t$, $R^u$ and $R^w$ are hydrogen and wherein A is selected from the radicals A3.dk1 to A3.dk81.

Table 474: Compounds of the formula I'.A and the salts and N-oxides thereof, wherein $R^1$, $R^t$, $R^u$ and $R^w$ are hydrogen and wherein A is selected from the radicals A3.dl1 to A3.dl81.

Table 475: Compounds of the formula I'.A and the salts and N-oxides thereof, wherein $R^1$ is methyl, $R^t$, $R^u$ and $R^w$ are hydrogen and wherein A is selected from the radicals A3.dl1 to A3.dl81.

Table 476: Compounds of the formula I'.A and the salts and N-oxides thereof, wherein $R^1$, $R^t$, $R^u$ and $R^w$ are hydrogen and wherein A is selected from the radicals A3.dm1 to A3.dm81.

Table 477: Compounds of the formula I'.A and the salts and N-oxides thereof, wherein $R^1$ is methyl, $R^t$, $R^u$ and $R^w$ are hydrogen and wherein A is selected from the radicals A3.dm1 to A3.dm81.

Table 478: Compounds of the formula I'.A and the salts and N-oxides thereof, wherein $R^1$, $R^t$, $R^u$ and $R^w$ are hydrogen and wherein A is selected from the radicals A3.dn1 to A3.dn81.

Table 479: Compounds of the formula I'.A and the salts and N-oxides thereof, wherein $R^1$ is methyl, $R^t$, $R^u$ and $R^w$ are hydrogen and wherein A is selected from the radicals A3.dn1 to A3.dn81.

Table 480: Compounds of the formula I'.A and the salts and N-oxides thereof, wherein $R^1$, $R^t$, $R^u$ and $R^w$ are hydrogen and wherein A is selected from the radicals A3.do1 to A3.do81.

Table 481: Compounds of the formula I'.A and the salts and N-oxides thereof, wherein $R^1$ is methyl, $R^t$, $R^u$ and $R^w$ are hydrogen and wherein A is selected from the radicals A3.do1 to A3.do81.

Table 482: Compounds of the formula I'.A and the salts and N-oxides thereof, wherein $R^1$, $R^t$, $R^u$ and $R^w$ are hydrogen and wherein A is selected from the radicals A3.ea1 to A3.ea81.

Table 483: Compounds of the formula I'.A and the salts and N-oxides thereof, wherein $R^1$ is methyl, $R^t$, $R^u$ and $R^w$ are hydrogen and wherein A is selected from the radicals A3.ea1 to A3.ea81.

Table 484: Compounds of the formula I'.A and the salts and N-oxides thereof, wherein $R^1$, $R^t$, $R^u$ and $R^w$ are hydrogen and wherein A is selected from the radicals A3.eb1 to A3.eb81.

Table 485: Compounds of the formula I'.A and the salts and N-oxides thereof, wherein $R^1$ is methyl, $R^t$, $R^u$ and $R^w$ are hydrogen and wherein A is selected from the radicals A3.eb1 to A3.eb81.

Table 486: Compounds of the formula I'.A and the salts and N-oxides thereof, wherein $R^1$, $R^t$, $R^u$ and $R^w$ are hydrogen and wherein A is selected from the radicals A3.ec1 to A3.ec81.

Table 487: Compounds of the formula I'.A and the salts and N-oxides thereof, wherein $R^1$ is methyl, $R^t$, $R^u$ and $R^w$ are hydrogen and wherein A is selected from the radicals A3.ec1 to A3.ec81.

Table 488: Compounds of the formula I'.A and the salts and N-oxides thereof, wherein $R^1$, $R^t$, $R^u$ and $R^w$ are hydrogen and wherein A is selected from the radicals A3.ed1 to A3.ed81.

Table 489: Compounds of the formula I'.A and the salts and N-oxides thereof, wherein $R^1$ is methyl, $R^t$, $R^u$ and $R^w$ are hydrogen and wherein A is selected from the radicals A3.ed1 to A3.ed81.

Table 490: Compounds of the formula I'.A and the salts and N-oxides thereof, wherein $R^1$, $R^r$, $R^u$ and $R^w$ are hydrogen and wherein A is selected from the radicals A3.ee1 to A3.ee81.

Table 491: Compounds of the formula I'.A and the salts and N-oxides thereof, wherein $R^1$ is methyl, $R^r$, $R^u$ and $R^w$ are hydrogen and wherein A is selected from the radicals A3.ee1 to A3.ee81.

Table 492: Compounds of the formula I'.A and the salts and N-oxides thereof, wherein $R^1$, $R^r$, $R^u$ and $R^w$ are hydrogen and wherein A is selected from the radicals A3.ef1 to A3.ef81.

Table 493: Compounds of the formula I'.A and the salts and N-oxides thereof, wherein $R^1$ is methyl, $R^r$, $R^u$ and $R^w$ are hydrogen and wherein A is selected from the radicals A3.ef1 to A3.ef81.

Table 494: Compounds of the formula I'.A and the salts and N-oxides thereof, wherein $R^r$, $R^u$ and $R^w$ are hydrogen and wherein A is selected from the radicals A3.eg1 to A3.eg81.

Table 495: Compounds of the formula I'.A and the salts and N-oxides thereof, wherein $R^1$ is methyl, $R^r$, $R^u$ and $R^w$ are hydrogen and wherein A is selected from the radicals A3.eg1 to A3.eg81.

Table 496: Compounds of the formula I'.A and the salts and N-oxides thereof, wherein $R^1$, $R^r$, $R^u$ and $R^w$ are hydrogen and wherein A is selected from the radicals A3.eh1 to A3.eh81.

Table 497: Compounds of the formula I'.A and the salts and N-oxides thereof, wherein $R^1$ is methyl, $R^r$, $R^u$ and $R^w$ are hydrogen and wherein A is selected from the radicals A3.eh1 to A3.eh81.

Table 498: Compounds of the formula I'.A and the salts and N-oxides thereof, wherein $R^1$, $R^r$, $R^u$ and $R^w$ are hydrogen and wherein A is selected from the radicals A3.ei1 to A3.ei81.

Table 499: Compounds of the formula I'.A and the salts and N-oxides thereof, wherein $R^r$ is methyl, $R^r$, $R^u$ and $R^w$ are hydrogen and wherein A is selected from the radicals A3.ei1 to A3.ei81.

Table 500: Compounds of the formula I'.A and the salts and N-oxides thereof, wherein $R^1$, $R^r$, $R^u$ and $R^w$ are hydrogen and wherein A is selected from the radicals A3.ek1 to A3.ek81.

Table 501: Compounds of the formula I'.A and the salts and N-oxides thereof, wherein $R^1$ is methyl, $R^r$, $R^u$ and $R^w$ are hydrogen and wherein A is selected from the radicals A3.ek1 to A3.ek81.

Table 502: Compounds of the formula I'.A and the salts and N-oxides thereof, wherein $R^1$, $R^r$, $R^u$ and $R^w$ are hydrogen and wherein A is selected from the radicals A3.el1 to A3.el81.

Table 503: Compounds of the formula I'.A and the salts and N-oxides thereof, wherein $R^1$ is methyl, $R^r$, $R^u$ and $R^w$ are hydrogen and wherein A is selected from the radicals A3.el1 to A3.el81.

Table 504: Compounds of the formula I'.A and the salts and N-oxides thereof, wherein $R^1$, $R^r$, $R^u$ and $R^w$ are hydrogen and wherein A is selected from the radicals A3.em1 to A3.em81.

Table 505: Compounds of the formula I'.A and the salts and N-oxides thereof, wherein $R^1$ is methyl, $R^r$, $R^u$ and $R^w$ are hydrogen and wherein A is selected from the radicals A3.em1 to A3.em81.

Table 506: Compounds of the formula I'.A and the salts and N-oxides thereof, wherein $R^1$, $R^r$, $R^u$ and $R^w$ are hydrogen and wherein A is selected from the radicals A3.en1 to A3.en81.

Table 507: Compounds of the formula I'.A and the salts and N-oxides thereof, wherein $R^1$ is methyl, $R^r$, $R^u$ and $R^w$ are hydrogen and wherein A is selected from the radicals A3.en1 to A3.en81.

Table 508: Compounds of the formula I'.A and the salts and N-oxides thereof, wherein $R^1$, $R^r$, $R^u$ and $R^w$ are hydrogen and wherein A is selected from the radicals A3.eo1 to A3.eo81.

Table 509: Compounds of the formula I'.A and the salts and N-oxides thereof, wherein $R^1$ is methyl, $R^r$, $R^u$ and $R^w$ are hydrogen and wherein A is selected from the radicals A3.eo1 to A3.eo81.

Table 510: Compounds of the formula I'.A and the salts and N-oxides thereof, wherein $R^1$, $R^r$, $R^u$ and $R^w$ are hydrogen and wherein A is selected from the radicals A3.fa1 to A3.fa81.

Table 511: Compounds of the formula I'.A and the salts and N-oxides thereof, wherein $R^1$ is methyl, $R^r$, $R^u$ and $R^w$ are hydrogen and wherein A is selected from the radicals A3.fa1 to A3.fa81.

Table 512: Compounds of the formula I'.A and the salts and N-oxides thereof, wherein $R^1$, $R^r$, $R^u$ and $R^w$ are hydrogen and wherein A is selected from the radicals A3.fb1 to A3.fb81.

Table 513: Compounds of the formula I'.A and the salts and N-oxides thereof, wherein $R^1$ is methyl, $R^r$, $R^u$ and $R^w$ are hydrogen and wherein A is selected from the radicals A3.fb1 to A3.fb81.

Table 514: Compounds of the formula I'.A and the salts and N-oxides thereof, wherein $R^1$, $R^r$, $R^u$ and $R^w$ are hydrogen and wherein A is selected from the radicals A3.fc1 to A3.fc81.

Table 515: Compounds of the formula I'.A and the salts and N-oxides thereof, wherein $R^1$ is methyl, $R^r$, $R^u$ and $R^w$ are hydrogen and wherein A is selected from the radicals A3.fc1 to A3.fc81.

Table 516: Compounds of the formula I'.A and the salts and N-oxides thereof, wherein $R^1$, $R^r$, $R^u$ and $R^w$ are hydrogen and wherein A is selected from the radicals A3.fd1 to A3.fd81.

Table 517: Compounds of the formula I'.A and the salts and N-oxides thereof, wherein $R^1$ is methyl, $R^2$ and $R^3$ are hydrogen and wherein A is selected from the radicals A3.fd1 to A3.fd81.

Table 518: Compounds of the formula I'.A and the salts and N-oxides thereof, wherein $R^1$, $R^r$, $R^u$ and $R^w$ are hydrogen and wherein A is selected from the radicals A3.fe1 to A3.fe81.

Table 519: Compounds of the formula I'.A and the salts and N-oxides thereof, wherein $R^1$ is methyl, $R^r$, $R^u$ and $R^w$ are hydrogen and wherein A is selected from the radicals A3.fe1 to A3.fe81.

Table 520: Compounds of the formula I'.A and the salts and N-oxides thereof, wherein $R^1$, $R^r$, $R^u$ and $R^w$ are hydrogen and wherein A is selected from the radicals A3.ff1 to A3.ff81.

Table 521: Compounds of the formula I'.A and the salts and N-oxides thereof, wherein $R^1$ is methyl, $R^r$, $R^u$ and $R^w$ are hydrogen and wherein A is selected from the radicals A3.ff1 to A3.ff81.

Table 522: Compounds of the formula I'.A and the salts and N-oxides thereof, wherein $R^1$, $R^r$, $R^u$ and $R^w$ are hydrogen and wherein A is selected from the radicals A3.fg1 to A3.fg81.

Table 523: Compounds of the formula I'.A and the salts and N-oxides thereof, wherein $R^1$ is methyl, $R^t$, $R^u$ and $R^w$ are hydrogen and wherein A is selected from the radicals A3.fg1 to A3.fg81.

Table 524: Compounds of the formula I'.A and the salts and N-oxides thereof, wherein $R^1$, $R^t$, $R^u$ and $R^w$ are hydrogen and wherein A is selected from the radicals A3.fh1 to A3.fh81.

Table 525: Compounds of the formula I'.A and the salts and N-oxides thereof, wherein $R^1$ is methyl, $R^t$, $R^u$ and $R^w$ are hydrogen and wherein A is selected from the radicals A3.fh1 to A3.fh81.

Table 526: Compounds of the formula I'.A and the salts and N-oxides thereof, wherein $R^1$, $R^t$, $R^u$ and $R^w$ are hydrogen and wherein A is selected from the radicals A3.fi1 to A3.fi81.

Table 527: Compounds of the formula I'.A and the salts and N-oxides thereof, wherein $R^1$ is methyl, $R^t$, $R^u$ and $R^w$ are hydrogen and wherein A is selected from the radicals A3.fi1 to A3.fi81.

Table 528: Compounds of the formula I'.A and the salts and N-oxides thereof, wherein $R^1$, $R^t$, $R^u$ and $R^w$ are hydrogen and wherein A is selected from the radicals A3.fk1 to A3.fk81.

Table 529: Compounds of the formula I'.A and the salts and N-oxides thereof, wherein $R^1$ is methyl, $R^t$, $R^u$ and $R^w$ are hydrogen and wherein A is selected from the radicals A3.fk1 to A3.fk81.

Table 530: Compounds of the formula I'.A and the salts and N-oxides thereof, wherein $R^1$, $R^t$, $R^u$ and $R^w$ are hydrogen and wherein A is selected from the radicals A3.fl1 to A3.fl81.

Table 531: Compounds of the formula I'.A and the salts and N-oxides thereof, wherein $R^1$ is methyl, $R^t$, $R^u$ and $R^w$ are hydrogen and wherein A is selected from the radicals A3.fl1 to A3.fl81.

Table 532: Compounds of the formula I'.A and the salts and N-oxides thereof, wherein $R^1$, $R^t$, $R^u$ and $R^w$ are hydrogen and wherein A is selected from the radicals A3.fm1 to A3.fm81.

Table 533: Compounds of the formula I'.A and the salts and N-oxides thereof, wherein $R^1$ is methyl, $R^t$, $R^u$ and $R^w$ are hydrogen and wherein A is selected from the radicals A3.fm1 to A3.fm81.

Table 534: Compounds of the formula I'.A and the salts and N-oxides thereof, wherein $R^1$, $R^t$, $R^u$ and $R^w$ are hydrogen and wherein A is selected from the radicals A3.fn1 to A3.fn81.

Table 535: Compounds of the formula I'.A and the salts and N-oxides thereof, wherein $R^1$ is methyl, $R^t$, $R^u$ and $R^w$ are hydrogen and wherein A is selected from the radicals A3.fn1 to A3.fn81.

Table 536: Compounds of the formula I'.A and the salts and N-oxides thereof, wherein $R^1$, $R^t$, $R^u$ and $R^w$ are hydrogen and wherein A is selected from the radicals A3.fo1 to A3.fo81.

Table 537: Compounds of the formula and the salts and N-oxides thereof, wherein $R^1$ is methyl, $R^t$, $R^u$ and $R^w$ are hydrogen and wherein A is selected from the radicals A3.fo1 to A3.fo81.

Further examples of compounds of this particularly preferred embodiment are the compounds of tables 370A to 537A wherein $R^t$, $R^u$ and $R^v$ are hydrogen and wherein A is as defined in tables 370 to 357 and wherein $R^1$ is a radical represented by each individual line (85 to 160) of table B.

Another particularly preferred embodiment of the invention relates to compounds of formula I'.B and to the salts and N-oxides thereof, wherein

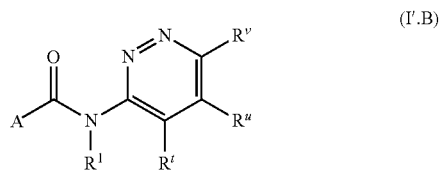

(I'.B)

A is a radical A1, as defined herein, in particular a radical A1, wherein $R^{41}$ and $R^{51}$ have the preferred meanings, in particular an oxazole radical of the formulae A1.a to A1.z, e.g. a radical selected from the oxazole radicals A1.a1 to A1.z81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^t$, $R^u$ and $R^v$ are independently of each other selected from hydrogen, methyl, difluoromethyl, trifluoromethyl, methoxy, difluoromethoxy and trifluoromethoxy; and wherein preferably at least one, more preferably 2 or 3, of the radicals $R^t$, $R^u$, and $R^v$ are hydrogen.

Examples of compounds of this particularly preferred embodiment are the compounds given in the following tables 538 to 588 and tables 538A to 588A.

Tables 538 to 588: Compounds of the formula I'.B and the salts and N-oxides thereof, wherein $R^t$, $R^u$ and $R^v$ are hydrogen and wherein A and $R^1$ are as defined in tables 1 to 50.

Tables 538A to 588A: Compounds of the formula I'.B and the salts and N-oxides thereof, wherein $R^t$, $R^u$ and $R^v$ are hydrogen and wherein A and $R^1$ are as defined in tables 1A to 50A.

Another particular preferred embodiment relates to compounds of the formula I'.B and to the salts and N-oxides thereof, wherein A is a radical A1, as defined herein, in particular a radical A1, wherein $R^{41}$ and $R^{51}$ have the preferred meanings, in particular a thiazole radical of the formulae A1.a' to A1.z', e.g. a radical selected from the thiazole radicals A1.a' 1 to A1.z' 81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^t$, $R^u$ and $R^v$ are independently of each other selected from hydrogen, methyl, difluoromethyl, trifluoromethyl, methoxy, difluoromethoxy and trifluoromethoxy; and wherein preferably at least one, more preferably 2 or 3, of the radicals $R^t$, $R^u$, and $R^v$ are hydrogen.

Examples of compounds of this particularly preferred embodiment are the compounds given in the following tables 589 to 639 and tables 589A to 639A.

Tables 589 to 639: Compounds of the formula I'.B and the salts and N-oxides thereof, wherein $R^t$, $R^u$ and $R^v$ are hydrogen and wherein A and $R^1$ are as defined in tables 51 to 100.

Tables 589A to 639A: Compounds, of the formula I'.B and the salts and N-oxides thereof, wherein $R^t$, $R^u$ and $R^v$ are hydrogen and wherein A and Ware as defined in tables 51A to 100A.

Another particular preferred embodiment relates to compounds of the formula I'.B and to the salts and N-oxides thereof, wherein A is a radical A2, as defined herein, in particular a radical A2, wherein $R^{42}$ and $R^{52}$ have the preferred meanings, in particular an oxazole radical of the formulae A2.aa to A2.do, e.g. a radical selected from the oxazole radicals A2.aa1-A2.aa81 to A2.ha1-A2.ha81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^t$, $R^u$ and $R^v$ are selected independently of each other from hydrogen, methyl, difluoromethyl, trifluoromethyl, methoxy, difluoromethoxy and trifluoromethoxy; and wherein preferably at least one, more preferably two or three of the radicals $R^t$, $R^u$ and $R^v$ are hydrogen.

Examples of compounds of this particular preferred embodiment are the compounds given in the following tables 640 to 690 and tbales 640A to 690A.

Tables 640 to 690: Compounds of the formula I'.B and the salts and N-oxides thereof, wherein $R^t$, $R^u$ and $R^v$ are hydrogen and wherein A and $R^1$ are as defined in tables 101 to 150.

Tables 640A to 690A: Compounds of the formula I'.B and the salts and N-oxides thereof, wherein $R^t$, $R^u$ and $R^v$ are hydrogen and wherein A and $R^1$ are as defined in 101A to 150A.

Another particular preferred embodiment relates to compounds of the formula I'.B and to the salts and N-oxides thereof, wherein A is a radical A2, as defined herein, in particular a radical A2, wherein $R^{42}$ and $R^{52}$ have the preferred meanings, in particular a thiazole radical of the formulae A2.aa' to A2.do', e.g. a radical selected from the thiazole radicals A2.aa' 1-A2.aa' 81 to A2.ha' 1-A2.ha' 81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^t$, $R^u$ and $R^v$ are selected independently of each other from hydrogen, methyl, difluoromethyl, trifluoromethyl, methoxy, difluoromethoxy and trifluoromethoxy; and wherein preferably at least one, more preferably two or three of the radicals $R^t$, $R^u$ and $R^v$ are hydrogen.

Examples of compounds of this particular preferred embodiment are the compounds given in the following tables 691 to 716 and tables 691A to 716A.

Tables 691 to 716: Compounds of the formula I'.B and the salts and N-oxides thereof, wherein $R^t$, $R^u$ and $R^v$ are hydrogen and wherein A and $R^1$ are as defined in tables 151 to 176.

Tables 691A to 716A: Compounds of the formula I'.B and the salts and N-oxides thereof, wherein $R^t$, $R^u$ and $R^v$ are hydrogen and wherein A and $R^1$ are as defined in tables 151A to 176A.

Another particular preferred embodiment relates to compounds of formula I'.B and to the salts and N-oxides thereof, wherein A is a radical A3, as defined herein, in particular a radical A3, wherein $R^{43}$ and $R^{53}$ have the preferred meanings, more particularly an oxazole radical of the formulae A3.aa to A3.do, e.g. a radical selected from the oxazole, thiazole, or imidazole radicals A3.aa1-A3.aa81 to A3.do1-A3.do81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^u$, $R^v$ and $R^t$ are selected independently of each other from hydrogen, methyl, difluoromethyl, trifluoromethyl, methoxy, difluoromethoxy and trifluoromethoxy; and wherein preferably at least one, more preferably 2 or 3, of the radicals $R^u$, $R^v$ and $R^t$ are hydrogen.

Examples of compounds of this particular preferred embodiment are the compounds given in the following tables 717 to 742 and tables 717A to 742A.

Tables 717 to 742: Compounds of the formula I'.B and the salts and N-oxides thereof, wherein $R^t$, $R^u$ and $R^v$ are hydrogen and wherein A and $R^1$ are as defined in tables 177 to 202.

Tables 717A to 742A: Compounds of the formula I'.B and the salts and N-oxides thereof, wherein $R^t$, $R^u$ and $R^v$ are hydrogen and wherein A and $R^1$ are as defined in tables 177A to 202A.

Another particular preferred embodiment relates to compounds of formula I'.B and to the salts and N-oxides thereof, wherein A is a radical A3, as defined herein, in particular a radical A3, wherein $R^{43}$ and $R^{53}$ have the preferred meanings, more particularly a thiazole radical of the formulae A3.aa' to A3.do', e.g. a radical selected from the thiazole radicals A3.aa' 1-A3.aa' 81 to A3.do' 1-A3.do' 81;

$R^1$ is hydrogen, $C_1$-$C_4$-alkyl or $C_1$-$C_4$-alkoxy-$C_1$-$C_2$-alkyl, most preferably hydrogen, methyl or ethyl;

$R^1$ is further most preferably represented by a radical as defined in each line of table B;

$R^u$, $R^v$ and $R^t$ are selected independently of each other from hydrogen, methyl, difluoromethyl, trifluoromethyl, methoxy, difluoromethoxy and trifluoromethoxy; and wherein preferably at least one, more preferably 2 or 3, of the radicals $R^u$, $R^v$ and $R^t$ are hydrogen.

Examples of compounds of this particular preferred embodiment are the compounds given in the following tables 743 to 760 and tables 743A to 760A.

Tables 743 to 760: Compounds of the formula I'.B and the salts and N-oxides thereof, wherein $R^t$, $R^u$ and $R^v$ are hydrogen and wherein A and $R^1$ are as defined in tables 342 to 369.

Tables 743A to 760A: Compounds of the formula I'.B and the salts and N-oxides thereof, wherein $R^t$, $R^u$ and $R^v$ are hydrogen and wherein A and $R^1$ are as defined in tables 342A to 369A.

The compounds of the formula I, wherein $X^1$ is O or S (compounds I'), can be prepared e.g. according to the method depicted in scheme 1 by reacting an activated oxazole, thiazole or imidazole carboxylic acid derivative II with a 3- or 4-aminopyridazine, compound III (see e.g. Houben-Weyl: "Methoden der organ. Chemie" [Methods of Organic Chemistry], Georg-Thieme-Verlag, Stuttgart, New York 1985, Volume E5, pp. 941-1045). Activated oxazole, thiazole or imidazole carboxylic acid derivatives II are, for example, acyl halides, activated esters, anhydrides, acyl azides, wherein X is for example chlorine, fluorine, bromine, para-nitrophenoxy, pentafluorophenoxy, N-hydroxysuccinimides, hydroxybenzotriazol-1-yl. In scheme 1, the radicals A, $R^1$, $R^t$, $R^u$, V and W have the meanings mentioned above and in particular the meanings mentioned as being preferred.

Scheme 1:

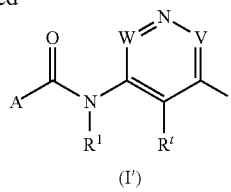

(I')

The compounds of the formula I, wherein $X^1$ is O or S (compounds I'), can also be prepared, for example, by reacting the oxzole or thiazole carboxylic acid IV and the 3- or 4-aminopyridazine compound III, in the presence of a coupling agent according to scheme 2. In scheme 2, the radicals A, $R^t$, $R^u$, V and W have the meanings given above and in particular the meanings given as being preferred.

Scheme 2:

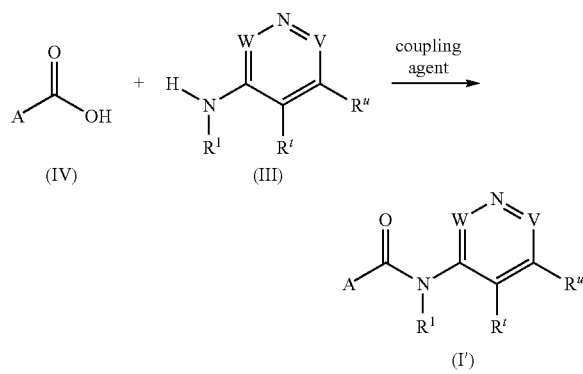

Suitable coupling agents are, for example:
coupling agents based on carbodiimides, for example N,N'-dicyclohexylcarbodiimide [J. C. Sheehan, G. P. Hess, J. Am. Chem. Soc. 1955, 77, 1067], N-(3-dimethylaminopropyl)-N'-ethylcarbodiimide; coupling agents which form mixed anhydrides with carbonic esters, for example 2-ethoxy-1-ethoxycarbonyl-1,2-dihydroquinoline [B. Belleau, G. Malek, J. Amer. Chem. Soc. 1968, 90, 1651], 2-isobutyloxy-1-isobutyloxycarbonyl-1,2-dihydroquinoline [Y. Kiso, H. Yajima, J. Chem. Soc., Chem. Commun. 1972, 942];
coupling agents based on phosphonium salts, for example (benzotriazol-1-yloxy)tris(dimethylamino)phosphonium hexafluorophosphate [B. Castro, J. R. Domoy, G. Evin, C. Selve, Tetrahedron Lett. 1975, 14, 1219], (benzotriazol-1-yloxy)tripyrrolidinophosphonium hexafluorophosphate [J. Coste et al., Tetrahedron Lett. 1990, 31, 205];
coupling agents based on uronium salts or having a guanidinium N-oxide structure, for example N,N,N',N'-tetramethyl-O-(1H-benzotriazol-1-yl)uronium hexafluorophosphate [R. Knorr, A. Trzeciak, W. Bannwarth, D. Gillessen, Tetrahedron Lett. 1989, 30, 1927], N,N,N',N'-tetramethyl-O-(benzotriazol-1-yl)uronium tetrafluoroborate, (benzotriazol-1-yloxy)dipiperidinocarbenium hexafluorophosphate [S. Chen, J. Xu, Tetrahedron Lett. 1992, 33, 647];
coupling agents which form acid chlorides, for example bis-(2-oxooxazolidinyl)phosphinic chloride [J. Diago-Mesequer, Synthesis 1980, 547].

Compounds of formula I, wherein $X^1$ is O (compounds I') and $R^1$ is different from hydrogen can also be prepared by alkylating the amides I (in which $R^1$ is hydrogen and which can be obtained according to scheme 1 or 2) using suitable alkylating agents in the presence of bases.

Scheme 3:

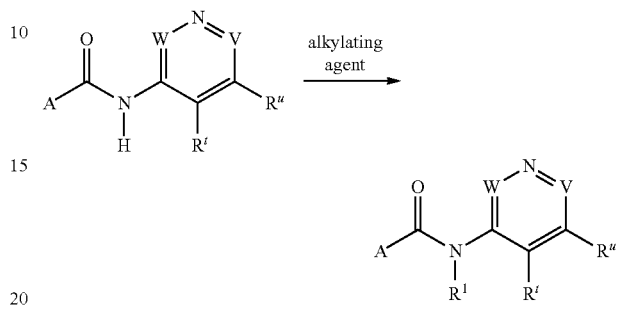

The oxazole, thiazole or imidazole carboxylic acids IV and their activated derivatives II as well as 3- or 4-aminopyridazine-compounds III please check if following names are correct are known in the art or are commercially available or can be prepared by methods known from the literature.

Compounds of the formula I, wherein $X^1$ is different from oxygen, can be prepared from the compounds of formula I' by standard methods:

Compounds of the formula I, wherein $X^1$ is S, can be prepared e.g. by reacting a compound of formula I' with 2,4-bis(4-methoxyphenyl)-1,3,2,4-dithiadiphosphetane-2,4-disulfide or phorphorus pentasulfide according to the method described by M. Jesberger et al. in Synthesis 2003, 1929.

Compounds of the formula I, wherein $X^1$ is $NR^{1a}$, can be prepared e.g. by reacting a compound I' with by reacting a compound I' with 2,4-bis(4-methoxyphenyl)-1,3,2,4-dithiadiphosphetane-2,4-disulfide to obtain the corresponding thioamide (compound I, wherein $X^1$ is S) which is then reacted with an appropriate amine according to the method described by V. Glushkov et al. in Pharmaceutical Chemistry Journal 2005, 39(10), 533-536.

Compounds of formula II, wherein $X^2=SR^{2a}$, can be prepared by alkylation of the corresponding thioamide (compound I, wherein $X^1$ is S) by reaction with an alkylating agent according to the method described by V. Glushkov et al. in Pharmaceutical Chemistry Journal 2005, 39(10) 533-536. In a similar manner, compounds I, wherein $X^2$ is $OR^{2a}$ or $NR^{2b}R^{2c}$ can be obtained. Compounds of the formula II, wherein $X^2=SOR^{2a}$ or $SO_2R^{2a}$ can be obtained by oxidation of compounds II with $X^2=SR^{2a}$.

N-oxides of the compounds of formulae I and II, can be prepared by oxidation of compounds I, according to standard methods of preparing heteroaromatic N-oxides, e.g. by the method described by C. Botteghi et al. in Journal of Organometallic Chemistry 1989, 370, 17-31.

As a rule, the compounds of formulae I or II can be prepared by the methods described above. If individual compounds can not be prepared via the above-described routes, they can be prepared by derivatization of other compounds I or II or by customary modifications of the synthesis routes described. For example, in individual cases, certain compounds I or II can advantageously be prepared from other compounds I or II by ester hydrolysis, amidation, esterification, ether cleavage, olefination, reduction, oxidetion and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the general formulae I or II may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formulae (I) or (II) or a salt or N-oxide thereof or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of formulae (I) or (II) or an agriculturally acceptable salt or N-oxide thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes.

The invention further provides an agricultural composition for combating such invertebrate pests, which comprises such an amount of at least one compound of the general formulae I or II or at least one agriculturally useful salt or N-oxide thereof and at least one inert liquid and/or solid agronomically acceptable carrier that has a pesticidal action and, if desired, at least one surfactant.

Such a composition may contain a single active compound of the formulae I or II or a salt or N-oxide thereof or a mixture of several active compounds I or II or their salts according to the present invention. The composition according to the present invention may comprise an individual isomer or mixtures of isomers as well as individual tautomers or mixtures of tautomers.

The compounds of the formulae I or II and the pesticidical compositions comprising them are effective agents for controlling arthropod pests and nematodes. Invertebrate pests controlled by the compounds of formulae I or II include for example insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla pini, Rhopalomyzus ascalonicus, Rhopalosiphum maidis, Rhopalosiphum padi, Rhopalosiphum insertum, Sappaphis, mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* siphonatera, e.g. *Xenopsylla cheopsis Ceratophyllus* spp.

The compositions and compounds of formulae I or II are useful for the control of nematodes, especially plant parasitic nematodes such as root knot nematodes, *Meloidogyne hapla, Meloidogyne incognita, Meloidogyne javanica,* and other *Meloidogyne* species;

cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Heliocotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formulae I or II are used for controlling insects or arachnids, in particular insects of the orders Lepidoptera, Coleoptera, Thysanoptera and Homoptera and arachnids of the order Acarina. The compounds of the formulae I or II according to the present invention are particularly useful for controlling insects of the order Thysanoptera and Homoptera.

The compounds of formula formulae I or II or the pesticidal compositions comprising them may be used to protect growing plants and crops from attack or infestation by invertebrate pests, especially insects, acaridae or arachnids by contacting the plant/crop with a pesticidally effective amount of compounds of, formulae I or II. The term "crop" refers both to growing and harvested crops.

The compounds of formulae I or II can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulphates, alkylsulfonates, fatty alcohol sulfates, fatty acids and sulphated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2- to 10-fold leading to concentrations in the ready to use preparations of 0.01 to 60% by weight active compound by weight, preferably 0.1 to 40% by weight.

The compounds of formulae I or II can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wetable powders (sprayable powders, oil dispersions) by adding water. To prepare emulsions, pastes or oil dispersions, the substances, as such or dissolved in an oil or solvent, can be homogenized in water by means of a wettings agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetting agents or other auxiliaries are added. The active compound(s) dissolves upon dilution with water, whereby a formula-tion with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetting agents and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetting agents and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active cornpound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formulae I or II are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pre-germinated the latter In a preferred embodiment a FS formulation is used for seed treatment. Typically, a FS formulation may comprise 1 to 800 g/l of active ingredient, 1 to 200 g/l Surfactant, 0 to 200 g/l antifreezing agent, 0 to 400 g/l of binder, 0 to 200 g/l of a pigment and up to 1 liter of a solvent, preferably water.

Other preferred FS formulations of compounds of formulae I or II for seed treatment comprise from 0.5 to 80 wt % of the active ingredient, from 0.05 to 5 wt % of a wetting agent, from 0.5 to 15 wt % of a dispersing agent, from 0.1 to 5 wt % of a thickener, from 5 to 20 wt % of an anti-freeze agent, from 0.1 to 2 wt % of an anti-foam agent, from 1 to 20 wt % of a pigment and/or a dye, from 0 to 15 wt % of a sticker/adhesion agent, from 0 to 75 wt % of a filler/vehicle, and from 0.01 to 1 wt % of a preservative.

Various types of oils, wetting agents, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formulae I or II are effective through both contact (via soil, glass, wall, bed net, carpet, plant parts or animal parts), and ingestion (bait, or plant part).

For use against ants, termites, wasps, flies, mosquitoes, crickets, or cockroaches, compounds of formulae I or II are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spraying devices, droplet sources, or evaporation sources. Gels can be based on aqueous or oily matrices and can be formulated to par-ticular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formulae I or II as aerosols (e.g. in spray cans), oil sprays or pump sprays are highly suitable for the non-professional user for controlling pests such as flies, fleas, ticks, mosquitos or cockroaches. Aerosol recipes are preferably corn-posed of the active compound, solvents such as lower alcohols (e.g. methanol, ethanol, propanol, butanol), ketones (e.g. acetone, methyl ethyl ketone), paraffin hydrocar-bons (e.g. kerosenes) having boiling ranges of approximately 50 to 250° C., dimethyl-formamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3 to 7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, am-photeric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formulae I or II and their respective compositions can also be used in mosquito and fumigating coils, smoke cartridges, vaporizer plates or long-term vaporizers and also in, moth papers, moth pads or other heat-independent vaporizer sys tems.

Methods to control infectious diseases transmitted by insects (e.g. malaria, dengue and yellow fever, lymphatic filariasis, and leishmaniasis) with compounds of formulae I or II and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for exam-ple are N,N-diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-H-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formulae I and II or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formulae I or II into contact with each other, and "seed dressing" to methods of seed treatment which provide the seeds with an amount of the compounds of formulae I or II, i.e. which generate a seed comprising the compound of formulae I or II. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formulae I or II or the enantiomers or veterinarily acceptable salts thereof are in particular also suitable for being used for combating parasites in and on animals.

A further object of the present invention is therefore to provide new methods for controlling parasites in and on animals. Another object of the invention is to provide safer pesticides for animals. Another object of the invention is further to provide pesticides for animals that may be used in lower doses than existing pesticides. And another object of the invention is, to provide pesticides for animals, which provide a long, residual control of the parasites.

The invention also relates to compositions containing a parasiticidally effective amount of compounds of formulae I or II or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of compounds of formulae I or II or the enantiomers or, veterinarily acceptable salts thereof and an acceptable carrier or a composition comprising it.

The present invention also provides a non-therapeutic method for treating, controlling, preventing and protecting animals against infestation and infection by parasites, which comprises applying to a locus-P a parasiticidally effective amount of a compound of formulae I or II or the enantiomers or veterinarily acceptable salts thereof and an acceptable carrier or a composition comprising it.

The invention also provides a process for the preparation of a composition for treating, controlling, preventing or protecting animals against infestation or, infection by parasites which comprises including a parasiticidally effective amount of a compound of, formulae I or II or the enantiomers or veterinarily acceptable salts thereof and an acceptable carrier or a composition comprising it.

The invention relates further to the use of compounds of formula I for treating, controlling, preventing or protecting animals against infestation or infection by parasites. The invention relates also to the use of a compound of formulae I or II or the enanti-omers or veterinarily acceptable salts thereof and an acceptable carrier or a composition comprising it, for the manufacture of a medicament for the therapeutic treatment of animals against infections or infestions by parasites.

Activity of compounds against agricultural pests does not suggest their suitability for control of endo- and ectoparasites in and on animals which requires, for example, low, nonemetic dosages in the case of oral application, metabolic compatibility with the animal, low toxicity, and a safe handling.

Surprisingly, it has been found that compounds of formulae I or II are suitable for combating endo- and ectoparasites in and on animals.

Compounds of formulae I or II or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in furbearing animals such as mink, chinchilla and raccoon, birds such as hens, geese, turkeys and ducks and fish such as fresh- and salt-water fish such as trout, carp and eels.

Compounds of formulae I or II or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting dice, ticks, nasal bots, keds, biting flies, muscoid flies, flies, myiasitic fly larvae, chiggers, gnats, mosquitoes and fleas.

The compounds of formulae I or II or the enantiomers or veterinarily acceptable salts thereof and compositions comprising them are suitable for systemic and/or non-systemic control of ecto- and/or endoparasites. They are active against all or some stages of development.

The compounds of formulae I or II are especially useful for combating ectoparasites.

The compounds of formulae I or II are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*, ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Orni-thodorus hermsi, Ornithodorus turicata* and parasitic mites (Mesostigmata), e.g. *Orni-thonyssus bacoti* and *Dermanyssus gallinae*, actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, bugs (Heteropterida): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum*,

*Enterobius vermicularis* (Threadworm), *Toxocara canis, Toxascaris leonine, Skrjabinema* spp., and *Oxyuris equi*, Camallanida, e.g. *Dracunculus medinensis* (guinea worm), Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formulae I or II and compositions containing them are particularly useful for the control of pests from the orders Diptera, Siphonaptera and Ixodida.

Moreover, the use of the formulae I or II and compositions containing them for combating mosquitoes is especially preferred.

The use of the compounds of formulae I or II and compositions containing them for combating flies is a further preferred embodiment of the present invention.

Furthermore, the use of the compounds of formulae I or II and compositions containing them for combating fleas is especially preferred.

The use of the compounds of formula formulae I or II and compositions containing them for combating ticks is a further preferred embodiment of the present invention.

The compounds of formulae I or II and compositions containing them also are especially useful for combating endoparasites (roundworms nematoda, thorny headed worms and planarians).

The compounds of formulae I or II and compositions containing them can be effective through both contact (via soil, glass, wall, bed net, carpet, blankets or animal parts) and ingestion (e.g. baits).

The present invention relates to the therapeutic and the non-therapeutic use of cornpounds of formulae I or II and compositions'containing them for controlling and/or combating parasites in and/or on animals.

The compounds of formulae I or II and compositions containing them may be used to protect the animals from attack or infestation by parasites by contacting them with a parasitically effective amount of compounds of formulae I or II and compositions containing them. As such, "contacting" includes both direct contact (applying the pesticidal mixtures/compositions directly on the parasite, which may include an indirect contact at it's locus-P, and optionally also administrating the pesticidal mixtures/composition directly on the animal) and indirect contact (applying the compounds/compositions to the locus of the parasite). The contact of the parasite through application to its locus is an example of a non-therapeutic use of compounds of formula I.

"Locus-P" as defined above means the habitat, food supply, breeding ground, area, material or environment in which a parasite is growing or may grow outside of the animal. The compounds of the invention can also be applied preventively to places at which occurrence of the pests or parasites is expected.

Administration can be carried out both prophylactically and therapeutically.

Administration of the active compounds is carried out directly or in the form of suitable preparations, orally, topically/dermally or parenterally.

For oral administration to warm-blooded animals, the compounds of formula I or II may be formulated as animal feeds, animal feed premixes, animal feed concentrates, pills, solutions, pastes, suspensions, drenches, gels, tablets, boluses and capsules. In addition, the compounds of formulae I or II may be administered to the animals in their drinking water. For oral administration, the dosage form chosen should provide the animal with 0.01 mg/kg to 100 mg/kg of animal body weight per day of the formulae I or II compound, preferably with 0.5 mg/kg to 100 mg/kg of animal body weight per day.

Alternatively, the compounds of formulae I or II may be administered to animals parenterally, for example, by intraruminal, intramuscular, intravenous or subcutaneous injection. The compounds of formulae I or II may be dispersed or dissolved in a physiologically acceptable carrier for subcutaneous injection. Alternatively, the compounds of formulae I or II may be formulated into an implant for subcutaneous administration. In addition the compounds of formulae I or II may be transdermally administered to animals. For parenteral administration, the dosage form chosen should provide the animal with 0.01 mg/kg to 100 mg/kg of animal body weight per day of the compounds of formulae I or II.

The compounds of formulae I or II may also be applied topically to the animals in the form of dips, dusts, powders, collars, medallions, sprays, shampoos, spot-on and pouron formulations and in ointments or oil-in-water or water-in-oil emulsions. For topical applica-tion, dips and sprays usually contain 0.5 ppm to 5 000 ppm and preferably 1 ppm to 3 000 ppm of the compounds of formulae I or II. In addition, the compounds of formulae I or II may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointmentlike consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, N-alkylpyrrolidones such as N-Methylpyrrolidone, N-butylpyrrolidone or N-octylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable Hydrophobic Phases (Oils) are:

liquid paraffins, silicone oils, natural vegetable oils such as sesame oil, almond oil, casfor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable Emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such, as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formulae I or II.

Generally, it is favorable to apply the compounds of formulae I or II in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formulae I or II against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formulae I or II are applied dermally/topically.

In a further preferred embodiment, the topical application is conducted in the form of compound-containing shaped articles such as collars, medallions, ear tags, bands for fixing at body parts, and adhesive strips and foils.

Generally, it is favorable to apply solid formulations which release compounds of formulae I or II in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formulae I or II. A detailed list of plastics and elastomers as well as preparation procedures for the shaped articles is given e.g. in WO 03/086075.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formulae I or II or the compositions comprising them in the use form as pesticides with other pesticides frequently results in a broader pesticidal spectrum of action.

The following list M of pesticides together with which the compounds of formulae I or II the invention can be used and with which potential synergistic effects might be produced, is intended to illustrate the possible combinations, but not to impose any limitation:

M.1. Organo(thio)phosphates: acephate, azamethiphos, azinphos-ethyl, azinphosmethyl, chlorethoxyfos, chlorfenvinphos, chlormephos, chlorpyrifos, chlorpyrifosmethyl, coumaphos, cyanophos, demeton-5-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, betacyfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, RU 15525, silafluofen, tefluthrin, tetramethrin, tralomethrin, transfluthrin, ZXI 8901;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); acetoprole, ethiprole, fipronil, pyrafluprole, pyriprole, vaniliprole, the phenylpyrazole compound of formula M6.1

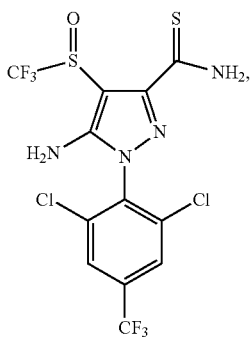

(M6.1)

M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonists: amitraz;

M.21. Ryanodine receptor modulators: flubendiamide; (R)-, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1);

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, 4-But-2-ynyloxy-6-(3,5-dimethyl-piperidin-1-yl)-2-fluoro-pyrimidine (M22.1), 3-Benzoylamino-N-[2,6-dimethyl-4-(1, 2,2,2-tetrafluoro-1-trifluoromethyl-ethyl)phenyl]-2-fluoro-benzamide (M22.2), 4-[5-(3,5-Dichloro-phenyl)-5-trifluoromethyl-4,5-dihydro-isoxazol-3-yl]-2-methyl-N-pyridin-2-ylmethyl-benzamide (M22.3), 4-[5-(3,5-Dichlorophenyl)-5-trifluoromethyl-4,5-dihydro-isoxazol-3-yl]-2-methyl-N-(2,2,2-trifluoro-ethyl)-benzamide (M22.4), 4-[5-(3,5-Dichlorophenyl)-5-trifluoromethyl-4,5-dihydro-isoxazol-3-yl]-2-methyl-N-thiazol-2-ylmethyl-benzamide (M22.5), 4-[5-(3,5-Dichloro-phenyl)-5-trifluoromethyl-4,5-dihydro-isoxazol-3-yl]-2-methyl-N-(tetrahydro-furan-2-yl-methyl)-benzamide (M22.6), 4-{[(6-Bromopyrid-3-yl)methyl](2-fluoroethyl)amino}furan-2(5H)-on (M22.7), 4-{[(6-Fluoropyrid-3-yl)methyl](2,2-difluoroethyl)amino}furan-2(5H)-on (M22.8), 4-{[(2-Chloro1,3-thiazolo-5-yl)methyl](2-fluoroethyl)amino}furan-2(5H)-on (M22.9), 4-{[(6-Chloropyrid-3-ylmethyl](2-fluoroethyl)amino}furan-2(5H)-on (M22.10), 4-{[(6-Chloropyrid-3-yl)methyl](2,2-difluoroethyl)amino}furan-2(5H)-on (M22.11), 4-{[(6-Chloro-5-fluoropyrid-3-yl)methyl](methyl)amino}furan-2(5H)-on (M22.12), 4-{[(5,6-Dichloropyrid-3-yl)methyl](2-fluoroethyhamino}furan-2(5H)-on (M22.13), 4-{[(6-Chloro-5-fluoropyrid-3-yl)methyl](cyclopropyl)amino}furan-2(5H)-on (M22.14), 4-{[(6-Chloropyrid-3-yl)methyl](cyclopropyl)amino}furan-2(5H)-on (M22.15), 4-{[(6-Chloropyrid-3-yl)methyl](methyl)amino}furan-2(5H)-on (M22.16), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho [2,1-b]pyrano[3,4-e]pyran-3,6-diyl]ester (M22.17), 8-(2-Cyclopropylmethoxy-4-methyl-phenoxy)-3-(6-methyl-pyridazin-3-yl)-3-azabicyclo[3.2.1]octane (M22.18);

M.23. N—R"-2,2-dihalo-1-R"cyclo-propanecarboxamide-2-(2,6-dichloro-α,α,α-tri-fluoro-ptolyl)hydrazone or N—R-2,2-di(R"')propionamide-2-(2,6-dichloro-α,α,α-trifluoro-p-tolyl)hydrazone, wherein R' is methyl or ethyl, halo is chloro or bromo, R" is hydrogen or methyl and R"' is methyl or ethyl;

M.24. Anthranilamides: chloranthraniliprole, cyantraniliprole,
5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M24.1),
5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M24.2),
5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M24.3),
5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M24.4),
5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M24.5),
5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M24.6);

M.25. Malononitrile compounds: $CF_2HCF_2CF_2CF_2CH_2C(CN)_2CH_2CH_2CF_3$, (2-(2,2,3,3,4,4,5,5-octafluoropentyl)-2-(3,3,3-trifluoro-propyl)malononitrile), $CF_3(CH_2)_2C(CN)_2CH_2(CF_2)_5CF_2H$, (2-(2,2,3,3,4,4,5,5,6,6,7,7-Dodecafluoroheptyl)-2-(3,3,3-trifluoro-propyl)-malononitrile), $CF_3(CH_2)_2$ $C(CN)_2(CH_2)_2C(CF_3)_2F$ (2-(3,4,4,4-Tetrafluoro-3-trifluoromethyl-butyl)-2-(3,3,3-trifluoro-propyl)-malononitrile), $CF_3(CH_2)_2C(CN)_2(CH_2)_2(CF_2)_3CF_3$ (2-(3,3,4,4,5,5,6,6,6-Nonafluoro-hexyl)-2-(3,3,3-trifluoro-propyl)-malononitrile), $CF_2H(CF_2)_3CH_2C(CN)_2CH_2(CF_2)_3CF_2H$ (2,2-Bis-(2,2,3,3,4,4,5,5-octafluoro-pentyl)-malononitrile), CF$_3$(CH$_2$)$_2$C(CN)$_2$CH$_2$(CF$_2$)$_3$CF$_3$ (2-(2,2,3,3,4,4,5,5,5-Nonafluoro-pentyl)-2-(3,3,3-trifluoro-propyl)-malononitrile), CF$_3$(CF$_2$)$_2$CH$_2$C(CN)$_2$CH$_2$(CF$_2$)$_3$CF$_2$H (2-(2,2,3,3,4,4,4-Heptafluoro-butyl)-2-(2,2,3,3,4,4,5,5-octafluoro-pentyl)-malononitrile), CF$_3$CF$_2$CH$_2$C(CN)$_2$CH$_2$(CF$_2$)$_3$CF$_2$H (2-(2,2,3,3,4,4,5,5-Octafluoro-pentyl)-2-(2,2,3,3,3-pentafluoro-propyl)-malononitrile), CF$_2$HCF$_2$CF$_2$CF$_2$CH$_2$C(CN)$_2$CH$_2$CH$_2$CF$_2$CF$_3$ (2-(2,2,3,3,4,4,5,5-octafluoropentyl)-2-(3,3,4,4,4-pentafluorobutyl)-malonodinitrile), CF$_3$(CH$_2$)$_2$C(CN)$_2$CH$_2$(CF$_2$)$_3$CF$_2$H (2-(2,2,3,3,4,4,5,5-octafluoropentyl)-2-(3,3,3-trifluoro-butyl)-malononitrile);

M.26. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

The commercially available compounds of the group M may be found in The Pesticide Manual, 14th Edition, British Crop Protection Council (2006) among other publications.

Thioamides of formula M6.1 and their preparation have been described in WO 98/28279. Lepimectin is known from Agro Project, PJB Publications Ltd, November 2004. Benclothiaz and its preparation have been described in EP-A1454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chlorantraniliprole has been described in WO 01/70671, WO 03/015519 and WO 05/118552. Cyantraniliprole has been described in WO 01/70671, WO 04/067528 and WO 05/118552. The anthranilamides M 24.1 to M 24.6 have been described in WO 2008/72743 and WO 200872783. The phthalamide M 21.1 is known from WO 2007/101540. Cyflumetofen and its preparation have been described in WO 04/080180. The aminoquinazolinone compound pyrifluquinazon has been described in EP A 109 7932. Sulfoximine sulfoxaflor has been described in WO 2006/060029 and WO 2007/149134. The alkynylether compound M22.1 is described e.g. in JP 2006131529. Organic sulfur compounds have been described in WO 2007060839. The carboxamide compound M 22.2 is known from WO 2007/83394. The oxazoline compounds M 22.3 to M 22.6 have been described in WO 2007/074789. The furanon compounds M 22.7 to M 22.16 have been described eg. in WO 2007/115644. The pyripyropene derivative M-22.17 has been described in WO 2008/66153 and WO 2008/108491. The pyridazin compound M 22.18 has been described in JP 2008/115155. The malononitrile compounds have been described in WO 02/089579 WO 02/090320, WO 02/090321, WO 04/006677, WO 05/068423, WO 05/068432 and WO 05/063694.

Fungicidal mixing partners are in particular those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-5-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, enestroburin, fluoxastrobin, kresoximmethyl, me-tominostrobin, orysastrobin, picoxystrobin, pyraclostrobin, pyribencarb or trifloxystrobin, sulfenic acid derivatives such as captafol, captan, dichlofluanid, folpet, tolylfluanid, cinnemamides and analogs such as dimethomorph, flumetover or flumorph.

The invertebrate pest, i.e. arthropodes and nematodes, the plant, soil or water in which the plant is growing can be contacted with the compound(s) of formulae I or II or composition(s) containing them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

Moreover, invertebrate pests may be controlled by contacting the target pest, its food supply, habitat, breeding ground or its locus with a pesticidally effective amount of compounds of formulae I or II. As such, the application may be carried out before or after the infection of the locus, growing crops, or harvested crops by the pest.

"Locus" in general means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formulae I or II and the compositions comprising said compounds can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formulae I and II can also be applied preventively to places at which occurrence of the pests is expected.

The compounds of formulae I or II may also be used to protect growing plants from attack or infestation by pests by contacting the plant with a pesticidally effective amount of compounds of formula I or II. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by, weight.

For use in treating crop plants, the rate of application of the active ingredients of, this invention may be in the range of 0.1 g to 4000 g per hectare, desirably from 25 g to 600 g per hectare, more desirably from 50 g to 500 g per hectare.

In the treatment of seed, the application rates of the active ingredients are generally from 0.1 g to 10 kg, per 100 kg of seed, preferably from 1 g to 5 kg per 100 kg of seed, in particular from −1 g to 200 g per 100 kg of seed.

The present invention is now illustrated in further detail by the following, examples.

I. PREPARATION EXAMPLES

The procedures described in the following preparation examples were used to prepare further compounds of formulae I and II by appropriate modification of the starting material. The resulting compounds, together with physical data, are listed in the table C below.

Products were characterized by HPLC (High Performance liquid Chromatography Mass Spectrometry). HPLC was carried out using an analytic RP-18 column (Chromolith Speed ROD from Merck KgaA, Germany) which was operated at 40° C. Acetonitrile with 0.1% by volume of a trifluoroacetic acid/water mixture and 0.1% by volume of trifluoroacetic acid served as mobile phase; flow rate: 1.8 ml/min and injection volume: 2 µl.

Example 1

2-Chloro-thiazole-4-carboxylic acid methyl-pyridazin-4-yl-amide

2-Chlorothiazole-4-carboxylic acid 14.0 g (73.1 mmol) of 2-chlorothiazole-4-carboxylic acid ethyl ester were slowly added to a solution of 11.0 g (0.17 mol, 85% purity) of potassium hydroxide in ethanol/water (1:3, 200 ml) at 0° C. The reaction mixture was stirred at room temperature for 16 h, diluted with water and washed twice with diethyl ether. The aqueous layer was acidified (pH=5.5) with conc. HCl and stirred at room temperature for three days. The formed precipitate was collected by filtration and dried at 40° C. under vacuum to yield 7.0 g (56%, 95% purity) of the title compound as a brown solid.

2-Chloro-thiazole-4-carboxylic acid methyl-pyridazin-4-yl-amide 200 mg (1.2 mmol) of 2-chlorothiazole-4-carboxylic acid and 96.1 mg (0.9 mmol) of pyridazin-4-yl-amine were dissolved in 6 ml dimethyl formamide. 0.15 mL (1.1 mmol) of triethyl amine followed by 382 mg (0.73 mmol) of 1H-Benzotriazol-1-yloxytri-pyrrolidinophosphonium hexafluorophosphate (PyBOP) were added and the reaction mixture was stirred at room temperature for 16 h. Brine was added and the reaction mixture was extracted three times with dichloromethane. The combined organic layers were dried over sodium sulfate, filtered and the solvent was removed under reduced pressure. The obtained residue was purified by flash column chromatography (silica, gradient elution cyclohexane, ethyl acetate, methanol) to give 200 mg (61%, 95% purity) of the title compound.

Example 2

2-Methyl-thiazole-4-carboxylic acid methyl-pyridazin-4-yl-amide 250 mg (1.8 mmol) of 2-Methyl-thiazole-4-carboxylic acid were suspended in 20 mL of toluene and two drops of dimethylformamide were added to the mixture. 0.16 mL of thionylchloride (2.2 mmol) were added at room temperature and the reaction mixture was stirred at 65° C. for two hours.

After removal of the solvent, toluene was added and the evaporation was repeated. The obtained residue was then dissolved in 10 mL of dichloromethane and the solution was added dropwise to a solution containing 166 mg pyridazin-4-yl-amine (1.8 mmol) and 0.27 ml triethyl amine (1.9 mmol) in 40 ml dichloromethane. The mixture was stirred at room temperature for 16 h and the solvent was removed under vacuum. The obtained residue was purified by flash column chromatography (silica, gradient elution cyclohexane, ethyl acetate, methanol) to give 50 mg (13%, 99% purity) of the title compound.

Compounds of the formula I and the salts or N-oxides thereof, wherein $R^r$, $R^u$ and W are CH, V is N and $X^1$ is O are hereinafter referred to as compounds I'.Aa.

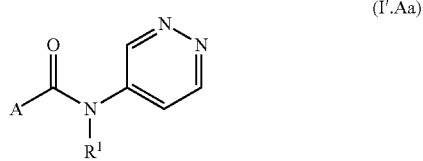

(I'.Aa)

Compounds of formula I'.Aa prepared according to the above mentioned method together with their physico-chemical data are compiled in table C below. $R^1$ and A in each case have the meanings given in the corresponding line of table C.

TABLE C

Compounds of formula I'.Aa prepared according to the above-mentioned method

| Example | $R^1$ | A | physico-chemical data: r.t. [min] |
|---|---|---|---|
| 1 | H | 2-methyl-5-trifluoromethyloxazol-4-yl | 1.883 |
| 2 | H | 2,4-dimethyloxazol-5-yl | 1.264 |
| 3 | H | 2,5-dimethyloxazol-4-yl | 1.468 |
| 4 | H | 2,4-dimethylthiazol-5-yl | 1.465 |
| 5 | methyl | 2-methylthiazol-4-yl | 1.288 |
| 6 | H | 2-methylthiazol-4-yl | 1.090 |
| 7 | H | 5-bromothiazol-4-yl | 1.560 |
| 8 | methyl | 5-bromothiazol-4-yl | 1.430 |
| 9 | H | 2-phenylthiazol-4-yl | 2.406 |
| 10 | methyl | 2-phenylthiazol-4-yl | 2.315 |
| 11 | H | 4-methylthiazol-5-yl | 1.263 |
| 12 | H | 2-(4-chlorophenyl)oxazol-4-yl | 2.537 |
| 13 | methyl | 2-(4-chlorophenyl)oxazol-4-yl | 2.524 |
| 14 | methyl | 2-chlorothiazol-4-yl | 1.606 |
| 15 | H | 5-methyl-3-(2,2,2-trifluoro-ethyl)-3H-imidazol-4-yl | 1.278 | r.t. = HPLC retention time

II. EVALUATION OF PESTICIDAL ACTIVITY

II.1 Activity Against Cotton Aphid (*Aphis gossypii*, Mixed Life Stages)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 2, 4, 6, and 11 respectively, at 300 ppm showed a mortality of at least 75% in comparison with untreated controls.

II.2 Activity Against Green Peach Aphid (*Myzus persicae*, Mixed Life Stages)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at 25° C. and 20-40% relative humidity. Aphid mortality on the treated plants, relative to mortality on untreated controt plants, was determined after 5 days.

In this test, the compounds 2, 4, and 11 respectively, at 300 ppm showed a mortality of at least 75% in comparison with untreated controls.

II.3 Activity Against Cowpea Aphid (*Aphis craccivora*)

The active compounds were formulated in 50:50 (vol:vol) acetone:water. The test solution was prepared at the day of use.

Potted cowpea plants colonized with 100-150 aphids of various stages were sprayed after the pest population had been recorded. Population reduction was assesed after 24, 72, and 120 hours.

In this test, the compounds 2, 3, 5, 6 and 7, respectively, at 300 ppm showed a mortality of at least 90% in comparison with untreated controls.

II.4 Activity Against Vetch Aphid (*Megoura viciae*)

The active compounds were formulated in 1:3 (vol:vol) DMSO:water with different concentrations of formulated compounds.

Bean leaf disks were placed into, microtiterplates filled with 0.8% agar-agar and 2.5 ppm OPUS™. The leaf disks were sprayed with 2.5 µl of the test solution and 5 to 8 adult aphids were placed into the microtiterplates which were then closed and kept at 23±1° C. and 50±5% relative humidity under fluorescent light for 6 days. Mortality was assessed on the basis of vital, reproduced, aphids. Aphid mortality and fecundity was then visually assessed.

In this test, the compounds 4, 6 and 7, respectively at a concentration of the test solution of 2500 mg/L showed a mortality of at least 90%.

II.5 Activity Against Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications. After application, 5 to 8 adult aphids were placed on the artificial membrane inside the microtiter plate wells. The aphids were then allowed to suck on the treated aphid diet and incubated at about 23+1° C. and about 50+5% relative humidity for 3 days. Aphid mortality and fecundity was then visually assessed.

In this test, compounds 2, 4, 6 and 7, respectively, at 2500 ppm showed 100% mortality in comparison with untreated controls.

The invention claimed is:

1. A compound of formula (I)

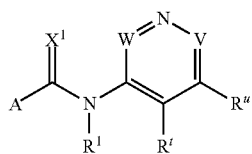

(I)

wherein

A is an oxazole or thiazole or imidazole radical of formulae A1, A2 or A3,

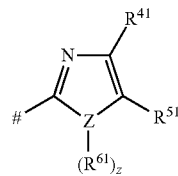

A1

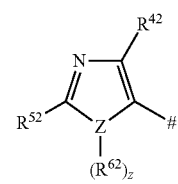

A2

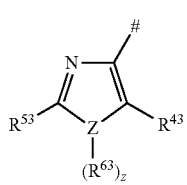

A3 wherein # denotes the binding site to the remainder of formula I;

Z is O or S for z=0 or

Z is N for z=1;

$R^{41}$, $R^{42}$, $R^{43}$ and $R^{51}$ are independently of each other selected from the group consisting of hydrogen, halogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^{41}$, $R^{42}$, $R^{43}$ and $R^{51}$ are selected from the group consisting of $OR^a$, $SR^a$, $C(Y)R^b$, $C(Y)OR^c$, $S(O)_2R^d$, $NR^eR^f$, heterocyclyl, $C_3$-$C_{10}$-cycloalkyl, $C_5$-$C_{10}$-cycloalkenyl and phenyl, wherein the four last mentioned radicals may be unsubstituted or may carry 1, 2, 3, 4 or 5 identical or different substituents $R^x$;

$R^{52}$ and $R^{53}$ are selected from the group consisting of hydrogen, halogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^{52}$ and $R^{53}$ are selected from the group consisting of $OR^a$; $SR^a$, $C(Y)R^b$, $C(Y)Or$, $S(O)_2R^d$, $NR^eR^f$, heterocyclyl, $C_3$-$C_{10}$-cycloalkyl, $C_5$-$C_{10}$-cycloalkenyl and phenyl, wherein the four last mentioned radicals may be unsubstituted or may carry 1, 2, 3, 4 or 5 identical or different substituents $R^x$, and wherein $R^{61}$, $R^{62}$, and $R^{63}$ are selected from the group consisting of hydrogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^{61}$, $R^{62}$, $R^{63}$ are selected from the group consisting of $OR^a$, $SR^a$, $C(Y)R^b$, $C(Y)OR^c$, $S(O)_2R^d$, $NR^eR^f$, $C(Y)NR^gR^h$, $S(O)_mNR^eR^f$, $C(Y)NR^iNR^eR^f$, heterocyclyl, $C_3$-$C_{10}$-cycloalkyl, $C_5$-$C_{10}$-cycloalkenyl and phenyl, wherein the four last mentioned radicals may be unsubstituted or may carry 1, 2, 3, 4 or 5 identical or different substituents $R^y$;

V is N;

W is $C(R^w)$; with $R^w$ being hydrogen;

$R^v$ is selected from the group consisting of hydrogen, halogen, $C_1$-$C_4$-alkyl, $C_1$-$C_3$-haloalkyl, $C_1$-$C_4$-alkoxy, $C_1$-$C_3$-haloalkoxy, $C_1$-$C_4$-alkylthio, $C_1$-$C_3$-haloalkylthio, $C_1$-$C_4$-alkylsulfinyl, $C_1$-$C_3$-haloalkylsulfinyl, $C_1$-$C_4$-alkylsulfonyl, $C_1$-$C_3$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl;

$R^t$ and $R^u$ are selected independently of each other from the group consisting of hydrogen, methyl, difluoromethyl, trifluoromethyl, methoxy, difluoromethoxy and trifluoromethoxy;

$X^1$ is O;

$R^1$ is hydrogen, $C_1$-$C_{10}$-alkyl, $C_1$-$C_{10}$-haloalkyl, $C_1$-$C_4$-alkylene-CN, heterocyclyl-$C_1$-$C_5$-alkyl, hetaryl-$C_1C_5$-alkyl, $C_1$-$C_5$-alkylen-$OR^a$ or $C_3$-$C_{10}$-cycloalkyl-$C_1$-$C_5$-alkyl;

m is 0, 1, or 2;

Y is O or S;

$R^a$, $R^b$ and $R^c$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-cycloalkyl-methyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from the group consisting of $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which are independently of each other selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$ and $R^f$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, phenyl-$C_1$-$C_4$-alkyl and hetaryl-$C_1$-$C_4$-alkyl, wherein the aromatic ring in the eight last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from the group consisting of O, S and N as a ring member atom and wherein the heterocycle may be unsubstituted or may carry 1, 2, 3, 4 or 5 substituents which are independently of each other selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$ and $R^h$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or substituents which are independently of each other selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^i$ is selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^x$ are independently of each other selected from the group consisting of cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_{10}$-alkylcarbonyl, $C_3$-$C_6$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicals $R^y$; and wherein $R^y$ is selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl;

wherein said heterocyclyl is a saturated, partially unsaturated or unsaturated 5-, 6-, 7- or 8-membered monocyclic heterocyclic radical or a saturated, partially unsaturated or unsaturated 8 to 10 membered bicyclic heterocyclic radical; wherein the monocyclic and bicyclic heterocyclic radicals comprise, as ring members, 1, 2, 3 or 4 heteroatoms selected from the group consisting of N, O and S;

and wherein said hetaryl is a monocyclic 5- or 6-membered heteroaromatic radical or a bicyclic 8- to 10-membered heteroaromatic; and wherein the monocyclic and bicyclic heteroaromatic radicals comprise, as ring members, 1, 2, 3 or 4 heteroatoms selected from the group consisting of N, O and S;

or an agriculturally or veterinally acceptable salt, N-oxide, enantiomer or diastereomer thereof.

2. The compound as claimed in claim 1, wherein $R^1$ is hydrogen or $C_1$-$C_3$-alkyl.

3. The compound as claimed in claim 1, wherein $R^t$ and $R^u$ are hydrogen.

4. The compound as claimed in claim 1, wherein Z is O.

5. The compound as claimed in claim 1, wherein Z is S.

6. The compound as claimed in claim 1, wherein Z is N.

7. The compound as claimed in claim 1, wherein A is a radical A1.

8. The compound as claimed in claim 7, wherein $R^{41}$ is selected from the group consisting of hydrogen, halogen, $C_1$-$C_4$-alkyl, $C_1$-$C_4$-haloalkyl, $C_3$-$C_6$-cycloalkyl and $C_3$-$C_6$-halocycloalkyl.

9. The compound as claimed in claim 7, wherein $R^{51}$ is selected from the group consisting of hydrogen, halogen, $C_1$-$C_4$-alkyl, $C_1$-$C_4$-haloalkyl, $C_3$-$C_6$-cycloalkyl and $C_3$-$C_6$-halocycloalkyl.

10. The compound as claimed in claim 7, wherein $R^{61}$ is selected from the group consisting of hydrogen, $C_1$-$C_4$-alkyl, $C_1$-$C_4$-haloalkyl, $C_3$-$C_6$-cycloalkyl-$C_1$-$C_4$-alkyl, heterocyclyl-$C_1$-$C_4$-alkyl, $C_1$-$C_4$-alkoxy-$C_1$-$C_4$-alkyl and $C_1$-$C_4$-alkyl-CN.

11. The compound as claimed in claim 1, wherein A is a radical A2.

12. The compound as claimed in claim 11, wherein $R^{42}$ is selected from the group consisting of hydrogen, halogen, $C_1$-$C_4$-alkyl, $C_1$-$C_4$-haloalkyl, $C_3$-$C_6$-cycloalkyl and $C_3$-$C_6$-halocycloalkyl.

13. The compound as claimed in claim 11, wherein $R^{52}$ is selected from the group consisting of hydrogen, halogen, $C_1$-$C_4$-alkyl, $C_1$-$C_4$-haloalkyl, $C_3$-$C_6$-cycloalkyl and $C_3$-$C_6$-halocycloalkyl.

14. The compound as claimed in claim 11, wherein $R^{62}$ is selected from the group consisting of hydrogen, $C_1$-$C_4$-alkyl, $C_1$-$C_4$-haloalkyl, $C_3$-$C_6$-cycloalkyl-$C_1$-$C_4$-alkyl, heterocyclyl-$C_1$-$C_4$-alkyl, $C_1$-$C_4$-alkoxy-$C_1$-$C_4$-alkyl and $C_1$-$C_4$-alkyl-CN.

15. The compound as claimed in claim 1, wherein A is a radical A3.

16. The compound as claimed in claim 15, wherein $R^{43}$ is selected from the group consisting of hydrogen, halogen, $C_1$-$C_4$-haloalkyl, $C_3$-$C_6$-cycloalkyl and $C_3$-$C_6$-halocycloalkyl.

17. The compound as claimed in claim 15, wherein $R^{53}$ is selected from the group consisting of hydrogen, halogen, $C_1$-$C_4$-alkyl, $C_1$-$C_4$-haloalkyl, $C_3$-$C_6$-cycloalkyl and $C_3$-$C_6$-halocycloalkyl.

18. The compound as claimed in claim 15, wherein $R^{63}$ is selected from the group consisting of hydrogen, $C_1$-$C_4$-alkyl, $C_1$-$C_4$-haloalkyl, $C_3$-$C_6$-cycloalkyl-$C_1$-$C_4$-alkyl, heterocyclyl-$C_1$-$C_4$-alkyl, $C_1$-$C_4$-alkoxy-$C_1$-$C_4$-alkyl and $C_1$-$C_4$-alkyl-CN.

19. A method for controlling invertebrate pests, wherein, the invertebrate pests are arthropod pests, which method comprises treating the pests, their food supply, their habitat or their breeding ground or a plant, seed, soil, area, material or environment in which the pests are growing or may grow, or the materials, plants, seeds, soils, surfaces or spaces to be protected from pest attack or infestation with a pesticidally effective amount of a compound of claim 1 or a salt or an N-oxide thereof.

20. The method as claimed in claim 19, wherein the invertebrate pests are insects.

21. The method as claimed in claim 20, wherein the invertebrate pests are insects of the order Homoptera.

22. A method for protecting plant propagation material and/or the plants which grow therefrom, which method comprises treating the plant propagation material with a pesticidally effective amount of a compound of claim 1 or an agriculturally acceptable salt or an N-oxide thereof.

23. Plant propagation material, treated with at least one compound of claim 1 and/or an agriculturally acceptable salt or an N-oxide thereof.

* * * * *